(12) United States Patent
Kadi et al.

(10) Patent No.: US 10,519,433 B2
(45) Date of Patent: *Dec. 31, 2019

(54) MUTANT POLYPEPTIDES AND USES THEREOF

(71) Applicant: INVISTA North America S.a.r.l., Wilmington, DE (US)

(72) Inventors: Nadia Kadi, Marton (GB); Adriana L. Botes, Rosedale East (GB); Mihai Luchian Azoitei, Chapel Hill, NC (US); Yih-En A. Ban, Seattle, WA (US); Daniela Grabs-Röthlisberger, Seattle, WA (US); Alexander Pisarchik, Bothell, WA (US); Alexandre Zanghellini, Seattle, WA (US); Eric Althoff, Seattle, WA (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 469 days.

This patent is subject to a terminal disclaimer.

(21) Appl. No.: 15/056,026

(22) Filed: Feb. 29, 2016

(65) Prior Publication Data

US 2016/0251645 A1 Sep. 1, 2016

Related U.S. Application Data

(60) Provisional application No. 62/126,279, filed on Feb. 27, 2015.

(51) Int. Cl.

| C12N 9/88 | (2006.01) |
|---|---|
| C08F 136/08 | (2006.01) |
| C08F 136/06 | (2006.01) |
| C08F 36/22 | (2006.01) |
| C07C 11/21 | (2006.01) |
| C07C 11/18 | (2006.01) |
| C07C 11/167 | (2006.01) |
| G01N 33/573 | (2006.01) |
| C08F 36/06 | (2006.01) |
| C07K 16/40 | (2006.01) |
| C08F 36/08 | (2006.01) |
| C12P 5/02 | (2006.01) |
| C12P 5/00 | (2006.01) |
| A61K 38/00 | (2006.01) |

(52) U.S. Cl.
CPC .............. *C12N 9/88* (2013.01); *A61K 38/00* (2013.01); *C07C 11/167* (2013.01); *C07C 11/18* (2013.01); *C07C 11/21* (2013.01); *C07K 16/40* (2013.01); *C08F 36/06* (2013.01); *C08F 36/08* (2013.01); *C08F 36/22* (2013.01); *C08F 136/06* (2013.01); *C08F 136/08* (2013.01); *C12P 5/007* (2013.01); *C12P 5/026* (2013.01); *G01N 33/573* (2013.01); *C07K 2299/00* (2013.01); *C12Y 402/01053* (2013.01); *C12Y 402/01095* (2013.01); *C12Y 402/01131* (2013.01)

(58) Field of Classification Search
None
See application file for complete search history.

(56) References Cited

U.S. PATENT DOCUMENTS

| 4,554,101 | A | 11/1985 | Hopp |
|---|---|---|---|
| 8,340,951 | B2 | 12/2012 | Baker et al. |
| 8,703,455 | B2 | 4/2014 | Marliere |
| 8,895,278 | B2 | 11/2014 | Marliere |
| 9,220,742 | B1 | 12/2015 | Botes et al. |
| 9,683,227 | B2 | 6/2017 | Althoff et al. |
| 2013/0217081 | A1 | 8/2013 | Pearlman et al. |
| 2015/0037860 | A1 | 2/2015 | Botes et al. |
| 2016/0186161 | A1* | 6/2016 | Marliere .......... C12N 9/88 435/166 |
| 2018/0030431 | A1 | 2/2018 | Althoff et al. |

FOREIGN PATENT DOCUMENTS

| WO | 2013/188546 A2 | 12/2013 |
|---|---|---|
| WO | 2014/100726 A2 | 6/2014 |
| WO | 2014/184345 A1 | 11/2014 |
| WO | 2015/000981 A2 | 1/2015 |

OTHER PUBLICATIONS

Altschul et al., "Gapped BLAST and PSI-BLAST: A New Generation of Protein Database Search Programs", Nucleic Acids Research, vol. 25, No. 17, 1997, pp. 3389-3402.

Whited et al., "Technology Update: Development of a Gas-Phase Bioprocess for Isoprene-Monomer Production Using Metabolic Pathway Engineering", Industrial Biotechnology, vol. 6, No. 3, Jun. 2010, pp. 152-163.

White, WM Claude, "Butadiene Production Process Overview", Chemico-Biological Interactions, vol. 166, 2007, pp. 10-14.

Brodkorb et al., "Linalool Dehydratase-Isomerase, a Bifunctional Enzyme in the Anaerobic Degradation of Monoterpenes", Journal of Biological Chemistry, vol. 285, No. 40, Oct. 1, 2010, pp. 30436-30442.

Devereaux et al., "A Comprehensive Set of Sequence Analysis Programs for the VAX", Nucleic Acids Research, vol. 12, No. 1, 1984, pp. 387-395.

Goodford, P.J., "A Computational Procedure for Determining Energetically Favorable Binding Sites on Biologically Important Macromolecules", Journal of Medicinal Chemistry, vol. 28, No. 7, 1985, pp. 849-857.

(Continued)

*Primary Examiner* — Suzanne M Noakes
*Assistant Examiner* — Jae W Lee
(74) *Attorney, Agent, or Firm* — Finnegan, Henderson, Farabow, Garrett & Dunner LLP

(57) ABSTRACT

The present disclosure provides novel polypeptides with 3-buten-2-ol dehydratase activity, polypeptides with catalytic activity in the conversion of 3-methyl-3-buten-2-ol to isoprene, and crystal structure data for one of such polypeptides. Methods of making and using the polypeptides and their related crystal structure data are also provided.

22 Claims, 17 Drawing Sheets
(6 of 17 Drawing Sheet(s) Filed in Color)

Specification includes a Sequence Listing.

(56) References Cited

OTHER PUBLICATIONS

Goodsell et al., "Automated Docking of Substrates to Proteins by Simulated Annealing", Proteins: Structure, Function, and Genetics, vol. 8, 1990, pp. 195-202.

Harlow et al., "Antibodies: A Laboratory Manual", Cold Spring Harbor Laboratory, 1988, 89 pages.

Ishizuka et al., "Putrescine Oxidase of Micrococcus Rubens : Primary Structure and *Escherichia Coli*", Journal of General Microbiology, vol. 139, 1993, pp. 425-432.

Jang et al., "Bio-based Production of C2-C6 Platform Chemicals", Biotechnology & Bioengineering, vol. 109, No. 10, Oct. 2012, pp. 2437-2459.

Kuntz et al., "A Geometric Approach to Macromolecule-Ligand Interactions", Journal of Molecular Biology, vol. 161, 1982, pp. 269-288.

Kyte et al., "A Simple Method for Displaying the Hydropathic Character of a Protein", Journal of Molecular Biology, vol. 157, No. 1, 1982, pp. 105-132.

Lattman, Eaton, "Use of the Rotation and Translation Functions", Methods in Enzymology, vol. 115, 1985, pp. 55-77.

Miranker et al., "Functionality. Maps of Binding Sites: A Multiple Copy Simultaneous Search Method", Proteins: Structure, Function and Genetics, vol. 11, 1991, pp. 29-34.

Myers et al., "Optimal Alignments in Linear Space", Bioinformatics, Computer Applications in the Biosciences , vol. 4, No. 1, 1988, pp. 11-17.

Pearson et al., "Improved Tools for Biological Sequence Comparison", Proceedings of the National Academy of Sciences, Biochemistry, vol. 85, Apr. 1988, pp. 2444-2448.

Sambrook et al., "Molecular Cloning: A Laboratory Manual, Cold Spring Harbor Laboratory", 4th Edition, vol. 1, 2012, 34 pages.

Notice of Allowance, U.S. Appl. No. 15/593,395, dated Oct. 3, 2018, 7 pages.

\* cited by examiner

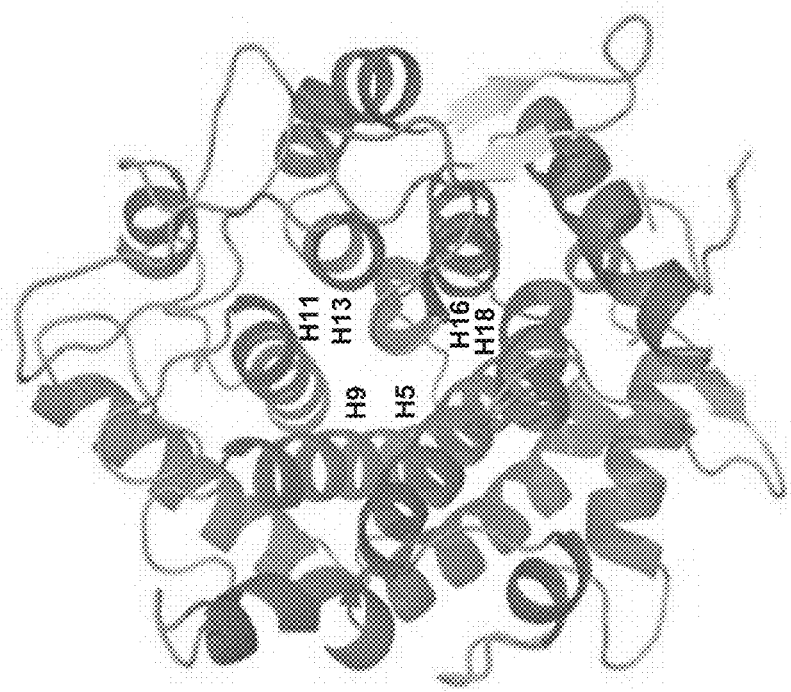
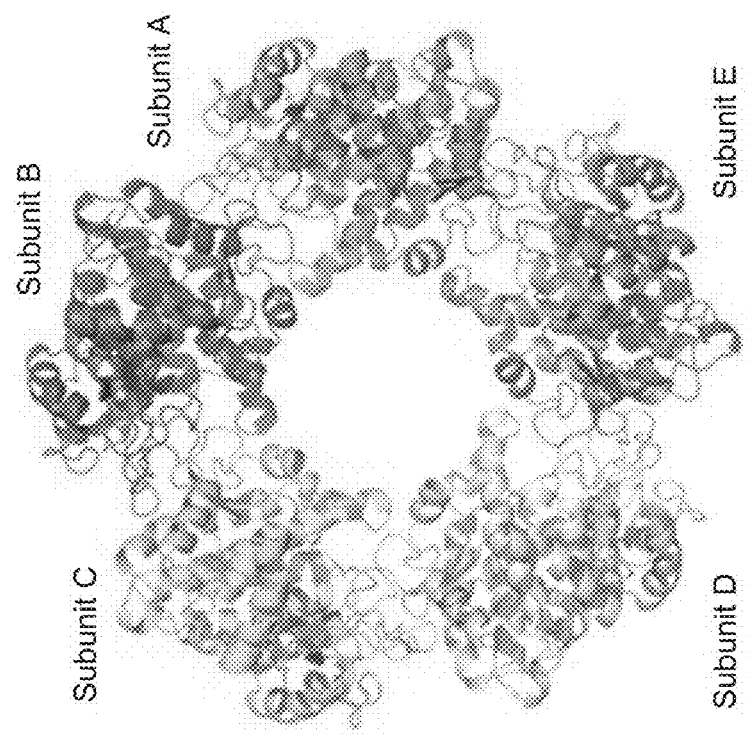
FIGURE 1

```
29                                                           78
LPPGRLATTEDYFAQQAKQAVTPDVMAQLAYMNYIDFISPFYSRGCSFEA 79                                                          128
WELKHTPQRVIKYSIAFYAYGLASVALIDPKLRALAGHDLDIAVSKMKCK 129                                                         178
RVWGDWEEDGFGTDPIEKENIMYKGHLNLMYGLYQLVTGSRRYEAEHAHL 179                                                         228
TRIIHDEIAANPFAGIVCEPDNYFVQCNSVAYLSLWVYDRLHGTDYRAAT 229                                                         278
RAWLDFIQKDLIDPERGAFYLSYHPESGAVKPWISAYTTAWTLAMVHGMD 279                                                         328
PAFSERYYPRFKQTFVEVYDEGRKARVRETAGTDDADGGVGLASAFTLLL 329                                                         378
AREMGDQQLFDQLLNHLEPPAKPSIVSASLRYEHPGSLLFDELLFLAKVH 379          390
AGFGALLRMPPP
```

*Generated with Polyview 2D*

FIG. 3

FIGURE 12
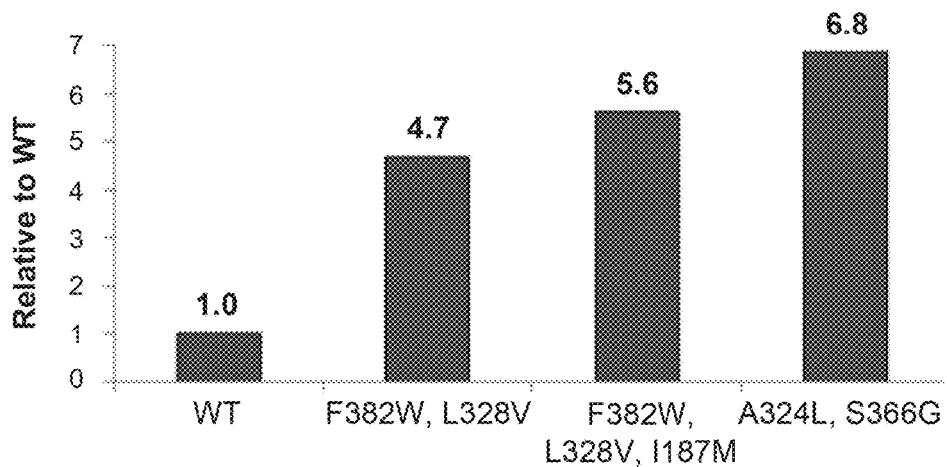
Fig. 12A
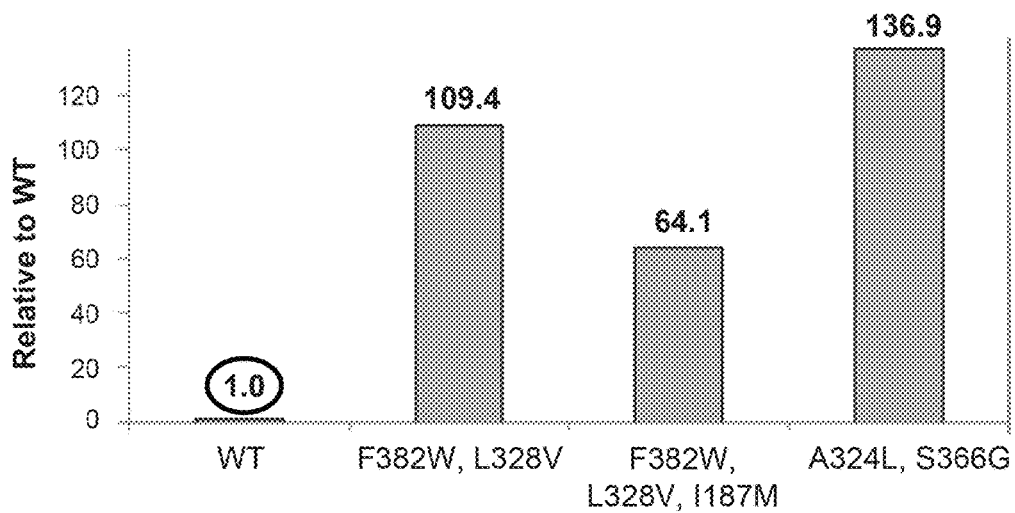
Fig. 12B

FIGURE 17
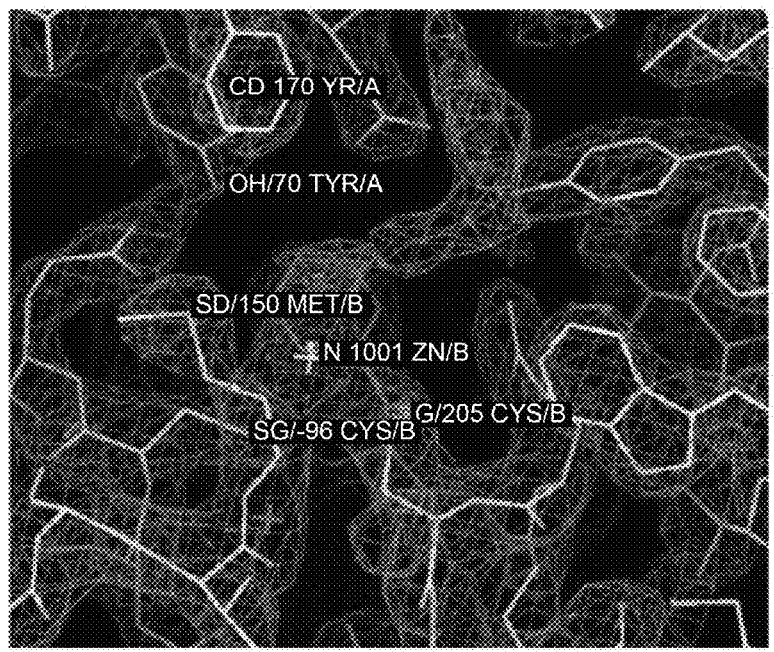
FIG. 17A
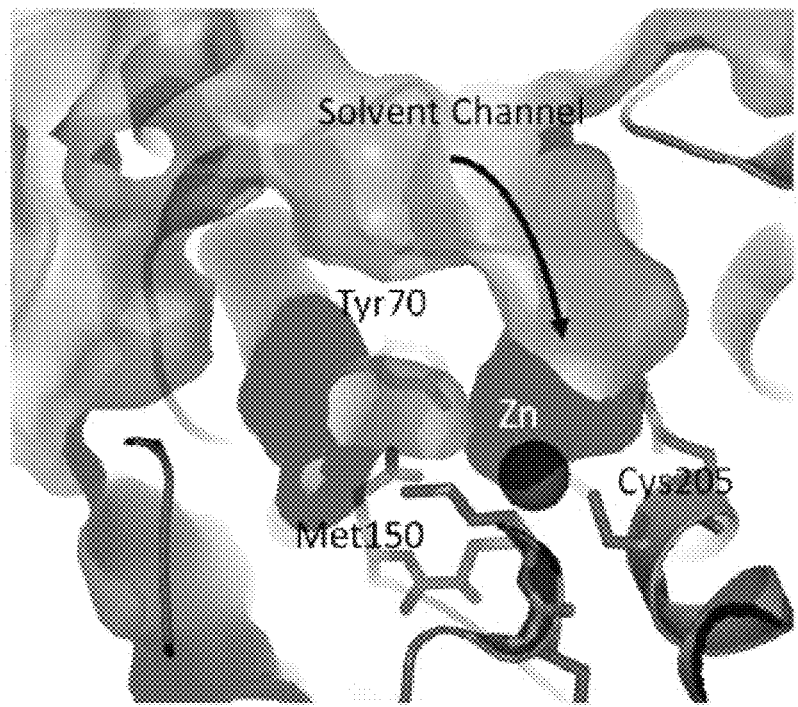
FIG. 17B

US 10,519,433 B2

MUTANT POLYPEPTIDES AND USES THEREOF

CROSS-REFERENCE TO RELATED APPLICATIONS

This application claims the benefit of U.S. Provisional Application No. 62/126,279, filed on Feb. 27, 2015, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 29, 2016, is named SEQUENCELISTING.txt and is 1,406,000 bytes in size.

LARGE FILES

The instant application contains three large tables all of which are ASCII text files and are as follows: Appendix 1, created Feb. 29, 2016 and 2,372,000 bytes in size; Appendix 2, created Feb. 29, 2016 and 1,244,000 bytes in size; and Appendix 3, created Feb. 29, 2016 and 135,000 bytes in size. All of these three tables are incorporated by reference in their entireties.

LENGTHY TABLES

The patent contains a lengthy table section. A copy of the table is available in electronic form from the USPTO web site (http://seqdata.uspto.gov/?pageRequest=docDetail&DocID=US10519433B2). An electronic copy of the table will also be available from the USPTO upon request and payment of the fee set forth in 37 CFR 1.19(b)(3).

FIELD

The present disclosure provides novel polypeptides with catalytic activity in the conversion of 3-buten-2-ol to butadiene, polypeptides with catalytic activity in the conversion of 3-methyl-3-buten-2-ol to isoprene, and crystal structure data for one of such polypeptides. Methods of making and using the polypeptides and their related crystal structure data are also provided.

BACKGROUND 1,3-Butadiene (hereinafter butadiene) is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile, which is used in the manufacture of Nylon-66 (White, Chemico-Biological Interactions, 2007, 166, 10-14). Butadiene is typically produced as a co-product from the steam cracking process, distilled to a crude butadiene stream, and purified via extractive distillation (White, Chemico-Biological Interactions, 2007, 166, 10-14). Industrially, 95% of global butadiene production is undertaken via the steam cracking process using petrochemical-based feedstocks such as naphtha. Butadiene has also been prepared, among other methods, by dehydrogenation of n-butane and n-butene (Houdry process) and oxidative dehydrogenation of n-butene (Oxo-D or O-X-D process) (White, Chemico-Biological Interactions, 2007, 166, 10-14). These methods are associated with high cost of production and low process yield (White, Chemico-Biological Interactions, 2007, 166, 10-14).

Isoprene is an important monomer for the production of specialty elastomers including motor mounts/fittings, surgical gloves, rubber bands, golf balls and shoes. Styrene-isoprene-styrene block copolymers form a key component of hot-melt pressure-sensitive adhesive formulations and cis-poly-isoprene is utilised in the manufacture of tires (Whited et al., *Industrial Biotechnology*, 2010, 6(3), 152-163). Manufacturers of rubber goods depend on either imported natural rubber from the Brazilian rubber tree or petroleum-based synthetic rubber polymers (Whited et al., 2010, supra).

Given a reliance on petrochemical feedstocks and energy intensive catalytic steps, biotechnology offers an alternative approach to butadiene and isoprene synthesis via biocatalysis. Biocatalysis is the use of biological catalysts, such as enzymes, to perform biochemical transformations of organic compounds. Accordingly, there is a need for sustainable methods for producing butadiene and isoprene, wherein the methods are biocatalyst-based (Jang et al, Biotechnology & Bioengineering, 2012, 109(10), 2437-2459). Both bio-derived feedstocks and petrochemical feedstocks are viable starting materials for the biocatalysis processes.

SUMMARY

This disclosure provides novel, recombinant, polypeptides that can catalyze the dehydration of 3-buten-2-ol to 1,3-butadiene and that of 3-methyl-3-buten-2-ol into isoprene. These novel polypeptides have numerous industrial applications in polymer biosynthesis. To improve on their catalytic activity, one of these polypeptides was crystallized and the respective crystal structure data is disclosed herein. Such crystal structure data can be used for modeling new and improved artificially-created enzymes with desired LDH activity.

Linalool dehydratase (EC 4.2.1.127; LDH) is a unique bi-functional enzyme which naturally catalyzes the dehydration of linalool to myrcene and the isomerization of linalool to geraniol. LDH can also catalyze the conversion of 3-methyl-3-buten-2-ol into isoprene. See PCT/US2013/045430, published as WO/2013/188546 and US Patent Publication No. 20150037860 herein incorporated by reference in their entireties. Isoprene can also be synthesized by other methods. See US Patent Publication Nos. 20150037860 and 20130217081, herein incorporated by reference in their entireties.

It has been discovered that LDH from *Castellaniella defragrans* (cdLD) is also able to convert 3-buten-2-ol to 1,3-butadiene, albeit in low yields. Provided herein are novel polypeptides with advantageous properties in industrial synthesis of 1,3-butadiene, relative to those of wild-type cdLD. These polypeptides exhibit improved 3-buten-2-ol dehydratase activity and also show improved activity in the catalysis of the conversion of 3-methyl-3-buten-2-ol into isoprene.

This disclosure also unveils the crystal structure of apo cdLD, elucidated by X-ray crystallography. Crystals of purified apo cdLD were obtained and the tri-dimensional structure of this enzyme elucidated for the first time, and independently confirmed. The elucidation of this crystal structure data allows for a better understanding of cdLD's enzymatic activity and the intelligent design of numerous improvements of the same, as well as the development of a variety of substrates and inhibitors.

Some embodiments provide a polypeptide comprising an amino acid sequence with at least 90% amino acid sequence homology to SEQ ID NO:1, wherein said amino acid sequence comprises at least one, preferably one to five, mutations at the following X positions of SEQ ID NO:1

$R_{1-95}X_{96}R_{97-98}X_{99}R_{100-122}X_{123}R_{124-186}X_{187}R_{188-203}X_{204}R_{205-211}X_{212}R_{213-272}X_{273}X_{274}X_{275}R_{276-323}X_{324}R_{325-327}X_{328}R_{329-R359}X_{360}R_{361-365}X_{366}R_{367-381}X_{382}R_{383-398}$, wherein:

$X_{96}$ is mutated to a different amino acid selected from L and equivalent amino acids;
$X_{99}$ is mutated to a different amino acid selected from L and equivalent amino acids;
$X_{123}$ is mutated to a different amino acid selected from I and equivalent amino acids;
$X_{187}$ is mutated to a different amino acid selected from M and equivalent amino acids;
$X_{204}$ is mutated to a different amino acid selected from I and equivalent amino acids;
$X_{212}$ is mutated to a different amino acid selected from F, Y, and equivalent amino acids;
$X_{273}$ is mutated to a different amino acid selected from C and equivalent amino acids;
$X_{274}$ is mutated to a different amino acid selected from F and equivalent amino acids;
$X_{275}$ is mutated to a different amino acid selected from I and equivalent amino acids;
$X_{324}$ is mutated to a different amino acid selected from L, E, and equivalent amino acids;
$X_{328}$ is mutated to a different amino acid selected from V and equivalent amino acids;
$X_{360}$ is mutated to a different amino acid selected from Y and equivalent amino acids;
$X_{366}$ is mutated to a different amino acid selected from V, C, G, and equivalent amino acids;
$X_{382}$ is mutated to a different amino acid selected from W and equivalent amino acids; and each R is the same as the corresponding amino acid in SEQ ID NO:1. In another embodiment, the homology to SEQ ID NO:1 is at least 91, at least 92, at least 93, at least 94, at least 95, at least 96, at least 97, at least 98, or at least 99%.

In another embodiment, the polypeptide of the previous paragraph is such that said amino acid sequence has at least 91% amino acid sequence homology to SEQ ID NO:1, preferably at least 92% amino acid sequence homology to SEQ ID NO:1, preferably at least 93% amino acid sequence homology to SEQ ID NO:1, preferably at least 94% amino acid sequence homology to SEQ ID NO:1, preferably at least 95% amino acid sequence homology to SEQ ID NO:, preferably at least 96% amino acid sequence homology to SEQ ID NO:1, preferably at least 97% amino acid sequence homology to SEQ ID NO:1, preferably at least 98% amino acid sequence homology to SEQ ID NO:1, or preferably at least 99% amino acid sequence homology to SEQ ID NO:1.

Another embodiment provides for the polypeptide according to the two previous paragraphs, wherein said amino acid sequence comprises one of the specified mutations at one of the following specified positions of SEQ ID NO:1

$R_{1-95}X_{96}R_{97-98}X_{99}R_{100-122}X_{123}R_{124-186}X_{187}R_{188-203}X_{204}R_{205-211}X_{212}R_{213-272}X_{273}X_{274}X_{275}R_{276-323}X_{324}R_{325-327}X_{328}R_{329-R359}X_{360}R_{361-365}X_{366}R_{367-381}X_{382}R_{383-398}$, wherein:

$X_{96}$ is mutated to a different amino acid selected from L and equivalent amino acids;
$X_{99}$ is mutated to a different amino acid selected from L and equivalent amino acids;
$X_{123}$ is mutated to a different amino acid selected from I and equivalent amino acids;
$X_{187}$ is mutated to a different amino acid selected from M and equivalent amino acids;
$X_{204}$ is mutated to a different amino acid selected from I and equivalent amino acids;
$X_{212}$ is mutated to a different amino acid selected from F, Y, and equivalent amino acids;
$X_{273}$ is mutated to a different amino acid selected from C and equivalent amino acids;
$X_{274}$ is mutated to a different amino acid selected from F and equivalent amino acids;
$X_{275}$ is mutated to a different amino acid selected from I and equivalent amino acids;
$X_{324}$ is mutated to a different amino acid selected from L, E, and equivalent amino acids;
$X_{328}$ is mutated to a different amino acid selected from V and equivalent amino acids;
$X_{360}$ is mutated to a different amino acid selected from Y and equivalent amino acids;
$X_{366}$ is mutated to a different amino acid selected from V, C, G, and equivalent amino acids;
$X_{382}$ is mutated to a different amino acid selected from W and equivalent amino acids; and each R is the same as the corresponding amino acid in SEQ ID NO:1

These listed positions are hereafter referred to as the specified positions and these listed mutations are hereafter referred to as the specified mutations.

In another embodiment, the polypeptide according to the previous paragraphs of this SUMMARY is such that said amino acid sequence comprises two of the specified mutations at two of the specified positions.

In another embodiment, the polypeptide according to the previous paragraphs of this SUMMARY is such that said amino acid sequence comprises three of the specified mutations at three of the specified positions.

In another embodiment, the polypeptide according to the previous paragraphs of this SUMMARY is such that said amino acid sequence comprises four of the specified mutations at four of the specified positions.

In another embodiment, the polypeptide according to the previous paragraphs of this SUMMARY is such that said amino acid sequence comprises five of the specified mutations at five of the specified positions.

In another embodiment, the polypeptide according to the previous paragraphs of this SUMMARY is such that X96 is mutated to a different amino acid selected from L and equivalent amino acids.

In another embodiment, the polypeptide according to the previous paragraphs of this SUMMARY is such that X99 is mutated to a different amino acid selected from L and equivalent amino acids.

In another embodiment, the polypeptide according to the previous paragraphs of this SUMMARY is such that X123 is mutated to a different amino acid selected from I and equivalent amino acids.

In another embodiment, the polypeptide according to the previous paragraphs of this SUMMARY is such that X187 is mutated to a different amino acid selected from M and equivalent amino acids.

In another embodiment, the polypeptide according to the previous paragraphs of this SUMMARY is such that X204 is mutated to a different amino acid selected from I and equivalent amino acids.

In another embodiment, the polypeptide according to the previous paragraphs of this SUMMARY is such that X212 is mutated to a different amino acid selected from F, Y, and equivalent amino acids.

In another embodiment, the polypeptide according to the previous paragraphs of this SUMMARY is such that X273 is mutated to a different amino acid selected from C and equivalent amino acids.

In another embodiment, the polypeptide according to the previous paragraphs of this SUMMARY is such that X274 is mutated to a different amino acid selected from F and equivalent amino acids.

In another embodiment, the polypeptide according to the previous paragraphs of this SUMMARY is such that X275 is mutated to a different amino acid selected from I and equivalent amino acids.

In another embodiment, the polypeptide according to the previous paragraphs of this SUMMARY is such that X324 is mutated to a different amino acid selected from L, E, and equivalent amino acids.

In another embodiment, the polypeptide according to the previous paragraphs of this SUMMARY is such that X328 is mutated to a different amino acid selected from V and equivalent amino acids.

In another embodiment, the polypeptide according to the previous paragraphs of this SUMMARY is such that X360 is mutated to a different amino acid selected from Y and equivalent amino acids.

In another embodiment, the polypeptide according to the previous paragraphs of this SUMMARY is such that X366 is mutated to a different amino acid selected from V, C, G, and equivalent amino acids.

In another embodiment, the polypeptide according to the previous paragraphs of this SUMMARY is such that X382 is mutated to a different amino acid selected from W and equivalent amino acids.

In another embodiment, the polypeptide according to the previous paragraphs of this SUMMARY is such that it comprises the following four mutations: V123I, V204I, M274F, and V275I; preferably comprising only those four mutations.

In another embodiment, the polypeptide according to the previous paragraphs of this SUMMARY is such that it comprises the following five mutations: V123I, V204I, M274F, V275I, and F382W; preferably comprising only those five mutations.

In another embodiment, the polypeptide according to the previous paragraphs of this SUMMARY is such that it comprises the following two mutations: V275I and F382W; preferably comprising only those two mutations.

In another embodiment, the polypeptide according to the previous paragraphs of this SUMMARY is such that it comprises the following four mutations: A324L, V275I, V123I, and V204I; preferably comprising only those four mutations.

In another embodiment, the polypeptide according to the previous paragraphs of this SUMMARY is such that it comprises the following two mutations: A324L and S366G; preferably comprising only those two mutations.

In another embodiment, the polypeptide according to the previous paragraphs of this SUMMARY is such that it comprises the following two mutations: M274F and F96L; preferably comprising only those two mutations.

In another embodiment, the polypeptide according to the previous paragraphs of this SUMMARY is such that it comprises the following two mutations: M274F and Y99L; preferably comprising only those two mutations.

In another embodiment, the polypeptide according to the previous paragraphs of this SUMMARY is such that it comprises the following two mutations: F382W and L212Y; preferably comprising only those two mutations.

In another embodiment, the polypeptide according to the previous paragraphs of this SUMMARY is such that it comprises the following two mutations: F382W and A273C.

In another embodiment, the polypeptide according to the previous paragraphs of this SUMMARY is such that it comprises the following two mutations: F382W and L328V; preferably comprising only those two mutations.

In another embodiment, the polypeptide according to the previous paragraphs of this SUMMARY is such that it comprises the following two mutations: F382W, L328V, and I187M; preferably comprising only those three mutations.

In another embodiment, the polypeptide according to the previous paragraphs of this SUMMARY is such that it comprises the following three mutations: V204I, M274F, and V275I; preferably comprising only those three mutations.

In another embodiment, the polypeptide according to the previous paragraphs of this SUMMARY is such that it comprises the following three mutations: V123I, M274F, and V275I; preferably comprising only those three mutations.

In another embodiment, the polypeptide according to the previous paragraphs of this SUMMARY is such that it comprises the following three mutations: V123I, V204I, and V275I; preferably comprising only those three mutations.

In another embodiment, the polypeptide according to the previous paragraphs of this SUMMARY is such that it comprises the following three mutations: V123I, V204I, and M274F; preferably comprising only those three mutations.

In another embodiment, the polypeptide according to the previous paragraphs of this SUMMARY is such that it comprises the following three mutations: M274F, V275I, and A324L; preferably comprising only those three mutations.

In another embodiment, the polypeptide according to the previous paragraphs of this SUMMARY is such that it comprises the following three mutations: M274F, V275I, and F382W; preferably comprising only those three mutations.

In another embodiment, the polypeptide according to the previous paragraphs of this SUMMARY is such that it comprises the following four mutations: M274F, V275I, R360Y, and F382W.

In another embodiment, the polypeptide according to the previous paragraphs of this SUMMARY is such that it comprises the following two mutations: V275I and A324L; preferably comprising only those two mutations.

In another embodiment, the polypeptide according to the previous paragraphs of this SUMMARY is such that it comprises the following two mutations: R360Y and F382W; preferably comprising only those two mutations.

In another embodiment, the polypeptide according to the previous paragraphs of this SUMMARY is such that it comprises a C-terminal His-tag.

In another embodiment, the polypeptide according to the previous paragraphs of this SUMMARY is such that it lacks a periplasmic tag.

In another embodiment, the polypeptide according to the previous paragraphs of this SUMMARY is such that the polypeptide has an activity in the catalysis of the dehydration of 3-buten-2-ol to 1,3-butadiene and/or in the catalysis of the dehydration of 3-methyl-3-buten-2-ol to isoprene that is at least 80% of that of a polypeptide consisting of SEQ ID NO:1, 4, 5, 7, or 8, increased about 1.5 fold or greater when compared to that of a polypeptide consisting of SEQ ID NO: 1, 4, 5, 7, or 8, preferably about 2 fold or greater when compared to that of a polypeptide consisting of SEQ ID NO: 1, 4, 5, 7, or 8, preferably about 2.5 fold or greater when compared to that of a polypeptide consisting of SEQ ID NO: 1, 4, 5, 7, or 8, preferably about 3 fold or greater when compared to that of a polypeptide consisting of SEQ ID NO:1, 4, 5, 7, or 8, preferably about 3.5 fold or greater when compared to that of a polypeptide consisting of SEQ ID NO: 1, 4, 5, 7, or 8, preferably about 4 fold or greater when compared to that of a polypeptide consisting of SEQ ID NO: 1, 4, 5, 7, or 8, preferably about 4.5 fold or greater when compared to that of a polypeptide consisting of SEQ ID NO: 1, 4, 5, 7, or 8, or preferably about 5 fold or greater when compared to that of a polypeptide consisting of SEQ ID NO: 1, 4, 5, 7, or 8, and wherein said activity is observed in at least one activity assay. In a further embodiment, said specific activity is measured with purified protein and is observed in at least one specific activity assay. In a further embodiment, said activity in the catalysis of the dehydration of 3-buten-2-ol to 1,3-butadiene and/or in the catalysis of the dehydration of 3-methyl-3-buten-2-ol to isoprene is observed in at least one type of non-bacterial cells. In a further embodiment, said activity in the catalysis of the dehydration of 3-buten-2-ol to 1,3-butadiene and/or in the catalysis of the dehydration of 3-methyl-3-buten-2-ol to isoprene is observed in at least one type of bacteria. In a further embodiment, said activity in the catalysis of the dehydration of 3-buten-2-ol to 1,3-butadiene and/or in the catalysis of the dehydration of 3-methyl-3-buten-2-ol to isoprene is observed in more than one type of bacteria. In a further embodiment, the bacteria are a strain of *E. Coli*. In a further embodiment, the bacteria are Origami2(DE3) or BL21(DE3).

Also provided are embodiments for a derivative of any one of the polypeptides according to the previous paragraphs of this SUMMARY.

Also provided are embodiments for a polynucleotide comprising, consisting of, or consisting essentially of a nucleic acid encoding any one of the polypeptides or derivatives according the previous paragraphs of this SUMMARY, preferably codon-optimized. In a further embodiment, the polynucleotide is either a DNA molecule or an RNA molecule. In a further embodiment, the polynucleotide further comprises a promoter operably linked to the nucleic acid sequence encoding the polypeptide or derivative.

Also provided are embodiments for a recombinant expression vector comprising a DNA molecule as described in any of the previous nucleotide-related paragraphs.

Also provided are embodiments for a host cell which is transformed or transduced with a DNA molecule as described in any of the previous nucleotide-related paragraphs or with a recombinant expression vector according the previous paragraph. In one further embodiment, the cell is such that the DNA molecule or the recombinant expression vector is integrated into a chromosome of the cell.

Also provided are embodiments for an organism, preferably a microorganism, comprising a heterologous DNA molecule encoding a polypeptide according to any one of the previous polypeptide-related paragraphs of this SUMMARY. In a further embodiment, the microorganism is a bacterium or a fungus. In a further embodiment, the microorganism is an *E. Coli* bacterium or a *Castellaniella defragrans* bacterium Also provided are embodiments for a transgenic animal or plant comprising a heterologous DNA molecule encoding a polypeptide according to any one of the previous polypeptide-related paragraphs of this SUMMARY.

Also provided are embodiments for a vector comprising a DNA molecule according to any one of the previous DNA molecule-related paragraphs of this SUMMARY.

Certain embodiments provide for a method of producing a polypeptide according to any one of the polypeptide-related paragraphs of this SUMMARY, the method comprising:

(i) preparing an expression construct which comprises a polynucleotide according to any one of the polynucleotide-related paragraphs of this SUMMARY, with a sequence encoding the polypeptide according to any one of the polypeptide-related paragraphs of this SUMMARY operably linked to one or more regulatory nucleotide sequences; (ii) transfecting or transforming a suitable host cell with the expression construct; (iii) expressing the recombinant polypeptide in said host cell; and (iv) isolating or purifying the recombinant polypeptide from said host cell or using the resultant host cell as is or as a cell extract.

Another embodiment provides a method of making a polypeptide with at least 80% activity, or improved activity, in the catalysis of the dehydration of 3-buten-2-ol to 1,3-butadiene and/or in the catalysis of the dehydration of 3-methyl-3-buten-2-ol to isoprene relative to that of a polypeptide consisting of SEQ ID NO: 1, 4, 5, 7, or 8, the method comprising preparing a polypeptide according to any one of the polypeptide-related paragraphs of this SUMMARY.

Also provided as embodiments are compositions comprising one or more polypeptides according to any one of the previous paragraphs of this SUMMARY. In a further embodiment, the composition in addition comprises the polypeptide of SEQ ID NO: 1, 4, 5, 7, or 8. In a further embodiment any of these compositions comprises one or more, preferably more than one in some embodiments, polypeptides according to any one of the polypeptide-related paragraphs of this SUMMARY with at least 80% activity, or improved activity, in the catalysis of the dehydration of 3-buten-2-ol to 1,3-butadiene and/or in the catalysis of the dehydration of 3-methyl-3-buten-2-ol to isoprene, relative to that of a polypeptide consisting of SEQ ID NO: 1, 4, 5, 7, or 8. In some of these embodiments, the reference polypeptide lacks a periplasmic tag. In some of these embodiments, the reference polypeptide has a His-tag. In some of these embodiments, the reference polypeptide lacks a periplasmic tag and has a His-tag. Also provided are embodiments for these compositions further comprising 3-buten-2-ol and/or 3-methyl-3-buten-2-ol. In other embodiments, these compositions further comprise 1,3-butadiene and/or isoprene.

Also provided, in another embodiment, is a composition that comprises a rubber product polymerized from 1,3-butadiene produced in the presence of a polypeptide according to any one of the polypeptide-related paragraphs of this SUMMARY. Also provided, in related embodiment, is a composition that (further) comprises a rubber product polymerized from isoprene produced in the presence of a polypeptide according to any one of the polypeptide-related paragraphs of this SUMMARY.

Also provided, in another embodiment, is a composition comprising a copolymer polymerized from 1,3-butadiene produced in the presence of a polypeptide according to any one of the polypeptide-related paragraphs of this SUMMARY. Also provided, in related embodiment, is a composition that (further) comprises a copolymer product polymerized from isoprene produced in the presence of a polypeptide according to any one of the polypeptide-related paragraphs of this SUMMARY Also provided, in another embodiment, is a composition comprising a plastic product polymerized from 1,3-butadiene produced in the presence of a polypeptide according to any one of the polypeptide-related paragraphs of this SUMMARY. Also provided, in related embodiment, is a composition that (further) comprises a plastic product polymerized from isoprene produced in the presence of a polypeptide according to any one of the polypeptide-related paragraphs of this SUMMARY.

Also provided, in another embodiment, is an antibody capable of binding to a polypeptide according to any one of the polypeptide-related paragraphs of this SUMMARY. Another embodiment provides for a fusion protein comprising a polypeptide according to any one of the polypeptide-related paragraphs of this SUMMARY.

Another embodiment provides for a complex comprising a polypeptide according to any one of the polypeptide-related paragraphs of this SUMMARY, said complex optionally further comprising 3-buten-2-ol. Another embodiment provides for a complex comprising a polypeptide according to any one of the polypeptide-related paragraphs of this SUMMARY, said complex optionally further comprising 3-methyl-3-buten-2-ol.

Another embodiment provides for a composition comprising 3-buten-2-ol and a means for producing 1,3-butadiene. Another embodiment provides for composition comprising a substrate and a means for enzymatically producing 1,3-butadiene from said substrate.

Another embodiment provides for method of producing 1,3-butadiene comprising: a step for enzymatically converting 3-buten-2-ol to 1,3-butadiene; and measuring and/or harvesting the 1,3-butadiene thereby produced.

Another embodiment provides for a container and a means for producing 1,3-butadiene.

Another embodiment provides for method of designing a polypeptide with at least 80% activity, or improved activity, in the catalysis of the dehydration of 3-buten-2-ol to 1,3-butadiene relative to that of a polypeptide consisting of SEQ ID NO: 1, 4, 5, 7, or 8, the method comprising mutating a means for enzymatically converting 3-buten-2-ol to 1,3-butadiene.

Another embodiment provides for a composition comprising 3-methyl-3-buten-2-ol and a means for producing isoprene.

Another embodiment provides for composition comprising a substrate and a means for enzymatically producing isoprene from said substrate.

Another embodiment provides for method of producing isoprene comprising: a step for enzymatically converting 3-methyl-3-buten-2-ol to isoprene; and measuring and/or harvesting the isoprene thereby produced.

Another embodiment provides for a container and a means for producing isoprene.

Another embodiment provides for method of designing a polypeptide with at least 80% activity, or improved activity, in the catalysis of the dehydration of 3-methyl-3-buten-2-ol to isoprene relative to that of a polypeptide consisting of SEQ ID NO:1, 4, 5, 7, or 8, the method comprising mutating a means for enzymatically converting 3-methyl-3-buten-2-ol to isoprene.

Another embodiment provides for a crystal having the coordinates set forth in Appendix I in space group P2(1) with cell parameters a=133.18 Å, b=110.83 Å, c=162.20 Å, which is produced from a polypeptide consisting of the amino acid sequence of SEQ ID NO:5 with up to 2% variation in any cell dimension. In another embodiment, the same crystal is expected to be produced from a polypeptide consisting of the amino acid sequence of SEQ ID NO:8 (SEQ ID NO:5 without the His-Tag).

Another embodiment provides for a crystal having the coordinates set forth in Appendix I in space group P2(1) with cell parameters a=133.18 Å, b=110.83 Å, c=162.20 Å, which is produced from a polypeptide consisting of the amino acid sequence of SEQ ID NO:5. In another embodiment, the same crystal is expected to be produced from a polypeptide consisting of the amino acid sequence of SEQ ID NO:8 (SEQ ID NO:5 without the His-Tag).

Another embodiment provides for a crystal according to the crystals described in the previous paragraphs, which diffracts x-rays for determination of atomic co-ordinates of the crystal to a resolution of between 48.16 Å and 2.54 Å.

Another embodiment provides for a crystal according to the crystals described in the previous paragraph, which comprises an active site comprising one or more residues selected from those of the following table, labeled according to SEQ ID NO:1 according to the coordinates of Appendix 1:

| Position | Residue Type | Chain |
| --- | --- | --- |
| 65 | ASP | C |
| 66 | PHE | C |
| 71 | TYR | C |
| 89 | VAL | A |
| 91 | LYS | A |
| 92 | TYR | A |
| 96 | PHE | A |
| 151 | MET | A |
| 155 | HIS | A |
| 197 | CYS | A |
| 198 | GLU | A |
| 203 | PHE | A |
| 205 | GLN | A |
| 206 | CYS | A |
| 209 | VAL | A |
| 266 | TYR | A |
| 267 | THR | A |
| 270 | TRP | A |
| 319 | VAL | A |
| 321 | LEU | A |
| 325 | PHE | A |
| 367 | LEU | A |
| 368 | LEU | A |
| 372 | LEU | A |

Another embodiment provides for a crystal according to any one of the crystals described in the previous paragraphs, which comprises a disulfide bridge between residues Cys74 and Cys127 of a polypeptide of SEQ ID NO:5. Another embodiment provides for a crystal according to any one of the crystals described in the previous paragraphs, which comprises a disulfide bridge between residues Cys74 and Cys127 of a polypeptide of SEQ ID NO:8, wherein the residue numbers are with relation to SEQ ID NO:1.

Another embodiment provides for a co-crystal comprising the crystal as according to any one of the crystals described in the previous paragraphs bound to a substrate, such as linalool, 3-buten-2-ol, or 3-methyl-3-buten-2-ol.

Another embodiment provides for a method of identifying a substrate or an inhibitor of a LDH, comprising any one or more of the steps of: (a) obtaining a crystal, or the coordinates of a crystal, of a polypeptide comprising SEQ ID NO:5 or 8, wherein the crystal is in space group P2(1), with unit cell dimensions of about a=133.18 Å, about b=110.83 Å, about c=162.20 Å; (b) obtaining or determining the three-dimensional structure of said polypeptide using the crystal of (a) by an X-ray diffraction method; (c) displaying the three dimensional structure of said complex on a performing computer by inputting said crystal structure data of said polypeptide, wherein the performing computer comprises a computer program to generate said three dimensional structure and to identify a substrate or an inhibitor; and (d) selecting a substrate or an inhibitor of the active site of the polypeptide. In some related embodiments, the substrate is chosen from linalool, 3-buten-2-ol, and 3-methyl-3-buten-2-ol.

Another embodiment provides for a method for designing a LDH substrate or an inhibitor, the method comprising any one or more of the steps of: (a) obtaining a crystal, or the coordinates of a crystal, in space group P2(1) with cell parameters a=133.18 Å, b=110.83 Å, c=162.20 Å, of a complex consisting of a polypeptide of SEQ ID NO:5 or 8 bound to a substrate or an inhibitor at its binding location; (b) obtaining or determining the three dimensional structure of the complex using the crystal obtained in (a) by an X-ray diffraction method to obtain the atomic coordinates of the structure; (c) providing on a computer the atomic coordinates of the three dimensional structure of the complex; and (d) utilizing a program operated by the computer to design a chemical compound predicted to bind to the polypeptide of SEQ ID NO:5 or 8 at the substrate or inhibitor's binding location and either act as a substrate or inhibit LDH, based on said three dimensional structure. In a related embodiment, the designing involves de novo rational drug design and/or computational protein design. In a related embodiment, the designing involves utilizing docking software and screening one or more databases for molecules that fit the substrate binding location on the polypeptide of SEQ ID NO:5 or 8. In some related embodiments, the substrate is chosen from linalool, 3-buten-2-ol, and 3-methyl-3-buten-2-ol. In some related embodiments, the rational drug design and/or computational protein design is based on the interactions between one or more of residues of the predictive active site of the polypeptide of SEQ ID NO:5 or 8 and linalool, 3-buten-2-ol, or 3-methyl-3-buten-2-ol. In some embodiments, one or more of the following residues (numbered with relation to SEQ ID NO:1) is part of the active site:

| Position | Residue Type | Chain |
| --- | --- | --- |
| 65 | ASP | C |
| 66 | PHE | C |
| 71 | TYR | C |
| 89 | VAL | A |
| 91 | LYS | A |
| 92 | TYR | A |
| 96 | PHE | A |
| 151 | MET | A |
| 155 | HIS | A |
| 197 | CYS | A |
| 198 | GLU | A |
| 203 | PHE | A |
| 205 | GLN | A |
| 206 | CYS | A |
| 209 | VAL | A |
| 266 | TYR | A |
| 267 | THR | A |
| 270 | TRP | A |
| 319 | VAL | A |
| 321 | LEU | A |
| 325 | PHE | A |
| 367 | LEU | A |
| 368 | LEU | A |
| 372 | LEU | A |

Another embodiment provides for a method according to any one of the methods described in the previous crystal-related methods, further comprising any one or more of: (e) synthesizing or obtaining the compound; and (f) evaluating the compound for its ability to perform one or more of (1) binding the polypeptide of SEQ ID NO:5 or 8, (2) competing with linalool, 3-buten-2-ol, or 3-methyl-3-buten-2-ol for binding the polypeptide of SEQ ID NO:5 or 8, (3) inhibiting LDH, or (4) being dehydrated by the polypeptide of SEQ ID NO:5 or 8.

Another embodiment provides for a method of preparing the crystal of the polypeptide of SEQ ID NO:5 or 8 according to any one of the previous paragraphs, which comprises: (a) providing a solution having said polypeptide, in a suitable buffer such as Tris about pH8 about 20 mM, NaCl about 150 mM, Glycerol about 5%; (b) mixing the solution with a crystallization solution comprising P8000 about 10%, Ethylene Glycol about 20%, Na-I-glutamate about 0.02M, dl-alanine about 0.02M, glycine about 0.02M, dl-lysine HCl about 0.02M, dl-serine about 0.02M; and (c) incubating the mixture under conditions to promote and for a time sufficient to produce the crystal of the polypeptide of SEQ ID NO:5 or 8.

Another embodiment provides for a method of preparing the co-crystal according to the previous co-crystal-related paragraphs of this SUMMARY, which comprises the steps of: (a) providing a solution having said polypeptide, in a suitable buffer such as Tris about pH8 about 20 mM, NaCl about 150 mM, Glycerol about 5%; (b) mixing the solution with a crystallization solution comprising P8000 about 10%, Ethylene Glycol about 20%, Na-I-glutamate about 0.02M, dl-alanine about 0.02M, glycine about 0.02M, dl-lysine HCl about 0.02M, dl-serine about 0.02M; and (c) incubating the mixture under conditions to promote and for a time sufficient to produce the co-crystal of said polypeptide bound to said substrate, such as linalool, 3-buten-2-ol, or 3-methyl-3-buten-2-ol.

Another embodiment provides for a method of identifying a compound that binds the polypeptide of SEQ ID NO:5 or 8, comprising: (a) obtaining a crystal comprising a protein consisting of SEQ ID NO:5 or 8, in space group P2(1) with cell parameters a=133.18 Å, b=110.83 Å, c=162.20 Å; (b) determining the three-dimensional structure of said polypeptide by X-ray diffraction to obtain the atomic coordinates of Appendix I; (c) contacting the polypeptide structure defined by the atomic coordinates of Appendix I, or a subset thereof with a test compound; and (d) detecting an interaction between the compound and the atomic coordinates, wherein an energetically favored interaction between the test compound and the atomic coordinates is indicative of a compound that binds said polypeptide.

Another embodiment provides for a crystal as defined in any one of the previous crystal-related paragraphs, wherein the atomic coordinates define one or more regions as set forth in Table 3.

Another embodiment provides for a polypeptide according to any one of the previous polypeptide-related paragraphs of this SUMMARY, wherein the polypeptide has an activity in the catalysis of the dehydration of 3-methyl-3-buten-2-ol to isoprene that is at least 80% of that of a polypeptide consisting of SEQ ID NO:1, 4, 5, 7, or 8, increased about 1.5 fold or greater when compared to that of a polypeptide consisting of SEQ ID NO: SEQ ID NO:1, 4, 5, 7, or 8, preferably about 2 fold or greater when compared to that of a polypeptide consisting of SEQ ID NO: SEQ ID NO:1, 4, 5, 7, or 8, preferably about 2.5 fold or greater when compared to that of a polypeptide consisting of SEQ ID NO: SEQ ID NO:1, 4, 5, 7, or 8, preferably about 3 fold or greater when compared to that of a polypeptide consisting of SEQ ID NO: SEQ ID NO:1, 4, 5, 7, or 8, preferably about 3.5 fold or greater when compared to that of a polypeptide consisting of SEQ ID NO: SEQ ID NO:1, 4, 5, 7, or 8, preferably about 4 fold or greater when compared to that of a polypeptide consisting of SEQ ID NO: SEQ ID NO:1, 4, 5, 7, or 8, preferably about 4.5 fold or greater when compared to that of a polypeptide consisting of SEQ ID NO: SEQ ID NO:1, 4, 5, 7, or 8, or preferably about 5 fold or greater when compared to that of a polypeptide consisting of SEQ ID NO: SEQ ID NO:1, 4, 5, 7, or 8, or preferably about 15 fold or greater when compared to that of a polypeptide consisting of SEQ ID NO: 1, 4, 5, 7, or 8, and wherein said activity is observed in at least one activity assay or preferably about 55 fold or greater when compared to that of a polypeptide consisting of 1, 4, 5, 7, or 8, preferably about 30 fold or greater when compared to that of a polypeptide consisting of 1, 4, 5, 7, or 8, and wherein said activity is observed in at least one activity assay. In some related embodiments, said activity in the catalysis of the dehydration of 3-methyl-3-buten-2-ol to isoprene is observed in at least one type of non-bacterial cells. In some other related embodiments, said activity in the catalysis of the dehydration of 3-methyl-3-buten-2-ol to isoprene is observed in at least one type of bacteria. In some other related embodiments, said activity in the catalysis of the dehydration of 3-methyl-3-buten-2-ol to isoprene is observed in more than one type of bacteria. In some related embodiments, the bacteria are a strain of E. Coli. In some related embodiments, the bacteria are Origami2(DE3) or BL21(DE3).

Another embodiment provides for composition comprising 3-methyl-3-buten-2-ol and a means for producing isoprene. Another embodiment provides for a composition comprising a substrate and a means for enzymatically producing isoprene from said substrate.

Another embodiment provides for a method of producing isoprene comprising:
a step for enzymatically converting 3-methyl-3-buten-2-ol to isoprene; and
measuring and/or harvesting the isoprene thereby produced.

Another embodiment provides for an apparatus comprising a container and a means for producing isoprene.

Another embodiment provides for a method of designing a polypeptide with at least 80% activity, or improved activity, in the catalysis of the dehydration of 3-methyl-3-buten-2-ol to isoprene relative to that of a polypeptide consisting of SEQ ID NO:1, 4, 5, 7, or 8, the method comprising mutating a means for enzymatically converting 3-methyl-3-buten-2-ol to isoprene.

Another embodiment provides for a polypeptide comprising any one or more of the sequences for each of the mutants identified in Appendix 3. Another embodiment provides for a polypeptide comprising any one or more of the sequences for each of the mutants identified in Table 9.

Another embodiment provides for a method for making an enzyme that has improved activity in the catalysis of the dehydration of 3-buten-2-ol to 1,3-butadiene and/or in the catalysis of the conversion of 3-methyl-3-buten-2-ol into isoprene comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative enzyme; producing the putative enzyme and confirming activity in the catalysis of the dehydration of 3-buten-2-ol to 1,3-butadiene and/or in the catalysis of the conversion of 3-methyl-3-buten-2-ol into isoprene. In one embodiment, this method is executed according to one or more of the techniques for computational design of enzymes disclosed in U.S. Pat. No. 8,340,951.

With respect to all of the above embodiments, and the claims, it is also within the scope of this disclosure all the embodiments that provide for "at least X % amino acid sequence identity to SEQ ID NO:1" instead of "at least X % amino acid sequence homology to SEQ ID NO:1," X being any of the % used in this disclosure and claims in the context of sequence homology.

The following example is provided in this regard, but many other embodiments exist for the embodiments where "homology" is replaced with "identity" wherein some embodiments provide a polypeptide comprising an amino acid sequence with at least 90% amino acid sequence identiy to SEQ ID NO:1, wherein said amino acid sequence comprises at least one, preferably one to five, mutations at the following X positions of SEQ ID NO:1

$R_{1-95}X_{96}R_{97-98}X_{99}R_{100-122}X_{123}R_{124-186}X_{187}R_{188-203}X_{204}R_{205-211}X_{212}R_{213-272}X_{273}X_{274}X_{275}R_{276-323}X_{324}R_{325-327}X_{328}R_{329\text{-}R359}X_{360}R_{361-365}X_{366}R_{367-381}X_{382}R_{383-398}$, wherein:

$X_{96}$ is mutated to a different amino acid selected from L and equivalent amino acids;

$X_{99}$ is mutated to a different amino acid selected from L and equivalent amino acids;

$X_{123}$ is mutated to a different amino acid selected from I and equivalent amino acids;

$X_{187}$ is mutated to a different amino acid selected from M and equivalent amino acids;

$X_{204}$ is mutated to a different amino acid selected from I and equivalent amino acids;

$X_{212}$ is mutated to a different amino acid selected from F, Y, and equivalent amino acids;

$X_{273}$ is mutated to a different amino acid selected from C and equivalent amino acids;

$X_{274}$ is mutated to a different amino acid selected from F and equivalent amino acids;
$X_{275}$ is mutated to a different amino acid selected from I and equivalent amino acids;
$X_{324}$ is mutated to a different amino acid selected from L, E, and equivalent amino acids;
$X_{328}$ is mutated to a different amino acid selected from V and equivalent amino acids;
$X_{360}$ is mutated to a different amino acid selected from Y and equivalent amino acids;
$X_{366}$ is mutated to a different amino acid selected from V, C, G, and equivalent amino acids;
$X_{382}$ is mutated to a different amino acid selected from W and equivalent amino acids; and each R is the same as the corresponding amino acid in SEQ ID NO:1. In another embodiment, the identity to SEQ ID NO:1 is at least 91, at least 92, at least 93, at least 94, at least 95, at least 96, at least 97, at least 98, or at least 99%.

Another embodiment provides for method for producing bioderived isoprene, myrcene, and/or 1,3-butadiene, comprising culturing or growing an host cell or an organism according to any one of the previous paragraphs of this SUMMARY under conditions and for a sufficient period of time to produce bioderived isoprene, myrcene, and/or 1,3-butadiene.

Another embodiment provides for culture medium comprising bioderived isoprene, myrcene, and/or 1,3-butadiene, wherein said bioderived isoprene, myrcene, and/or 1,3-butadiene has a carbon-12, carbon-13 and carbon-14 isotope ratio that reflects an atmospheric carbon dioxide uptake source. In some embodiments, said culture medium is separated from a host cell or an organism according to any one of of the previous paragraphs of this SUMMARY.

Another embodiment provides for bioderived isoprene, myrcene, and/or 1,3-butadiene having a carbon-12, carbon-13 and carbon-14 isotope ratio that reflects an atmospheric carbon dioxide uptake source, preferably produced by growing an host cell or an organism according to any one of the previous paragraphs of this summary. In some embodiments, said bioderived isoprene, myrcene, and/or 1,3-butadiene of claim 115, wherein said bioderived isoprene, myrcene, and/or 1,3-butadiene has an Fm value of at least 80%, at least 85%, at least 90%, at least 95% or at least 98%. Some embodiments provide for a composition comprising said bioderived isoprene, myrcene, and/or 1,3-butadiene according to any one of the previous paragraphs of this SUMMARY and a compound other than said bioderived isoprene, myrcene, and/or 1,3-butadiene. In some embodiments of said compositions, said compound other than said bioderived isoprene, myrcene, and/or 1,3-butadiene is a trace amount of a cellular portion of a host cell or an organism according to any one of the previous paragraphs of this summary.

Some embodiments provide for a biobased polymer comprising the bioderived isoprene, myrcene, and/or 1,3-butadiene according to any one of the previous paragraphs of this SUMMARY.

Some embodiments provide for a biobased resin comprising the bioderived isoprene, myrcene, and/or 1,3-butadiene according to any one of the previous paragraphs of this SUMMARY.

Some embodiments provide for a molded product obtained by molding a biobased polymer of any one of the previous paragraphs of this SUMMARY.

Some embodiments provide for a process for producing a biobased polymer of claim 119 comprising chemically reacting the bioderived isoprene, myrcene, and/or 1,3-butadiene of any one of the previous paragraphs of this SUMMARY with itself or another compound in a polymer-producing reaction.

Some embodiments provide for a molded product obtained by molding a biobased resin of any one of the previous paragraphs of this SUMMARY.

Some embodiments provide for a process for producing a biobased resin of any one of the previous paragraphs of this SUMMARY comprising chemically reacting said bioderived isoprene, myrcene, and/or 1,3-butadiene with itself or another compound in a resin producing reaction.

One embodiment provides for a crystal comprising the coordinates set forth in Appendix 2 in space group P2(1) with cell parameters a=88.7 Å, b=111.22 Å, c=120.42 Å, which is produced from a polypeptide consisting of the amino acid sequence of SEQ ID NO:9 with up to 2% variation in any cell dimension. One embodiment provides for a composition comprising said crystal. In some embodiments, said crystal diffracts x-rays for determination of atomic co-ordinates of the crystal to a resolution of between 2.67 Å and 2.60 Å. In some embodiments, said crystal comprises a metal ion, preferably zinc.

Some embodiments provide for a co-crystal comprising the crystal as defined bound to a substrate, such as linalool, 3-buten-2-ol, and 3-methyl-3-buten-2-ol.

Some embodiments provide for a method of identifying a substrate or an inhibitor of a LDH, comprising any one or more of the steps of: (a) obtaining a crystal, or the coordinates of a crystal, of a polypeptide comprising SEQ ID NO:8 or 9, wherein the crystal is in space group space group P2(1) with cell parameters a=88.7 Å, b=111.22 Å, c=120.42 Å; (b) obtaining or determining the three-dimensional structure of said polypeptide using the crystal of (a) by an X-ray diffraction method; (c) displaying the three dimensional structure of said complex on a performing computer by inputting said crystal structure data of said polypeptide, wherein the performing computer comprises a computer program to generate said three dimensional structure and to identify a substrate or an inhibitor; and (d) selecting a substrate or an inhibitor of the active site of the polypeptide.

Some embodiments provide for method for designing a LDH substrate or an inhibitor, the method comprising any one or more of the steps of: (a) obtaining a crystal, or the coordinates of a crystal, in space group P2(1) with cell parameters a=88.7 Å, b=111.22 Å, c=120.42 Å, of a complex consisting of a polypeptide of SEQ ID NO:8 or 9 bound to the substrate or inhibitor at its binding location; (b) obtaining or determining the three dimensional structure of the complex using the crystal obtained in (a) by an X-ray diffraction method to obtain the atomic coordinates of the structure; (c) providing on a computer the atomic coordinates of the three dimensional structure of the complex; and (d) utilizing a program operated by the computer to design a chemical compound predicted to bind to the polypeptide of SEQ ID NO:8 or 9 at the substrate or inhibitor's binding location and either act as a substrate or inhibit the LDH, based on said three dimensional structure. In some embodiments of this method, the designing involves de novo rational drug design and/or computational protein design.

In some other embodiments of said method, the designing involves utilizing docking software and screening one or more databases for molecules that fit the substrate binding location on the polypeptide of SEQ ID NO:8 or 9.

Some embodiments provide for a method, further comprising any one or more of: (e) synthesizing or obtaining the compound; and (f) evaluating the compound for its ability to perform one or more of (1) binding the polypeptide of SEQ ID NO:8 or 9, (2) competing with linalool, 3-buten-2-ol, or 3-methyl-3-buten-2-ol for binding the polypeptide of SEQ ID NO:8 or 9, (3) inhibiting LDH, or (4) being dehydrated by the polypeptide of SEQ ID NO:8 or 9.

In some embodiments, the method of, wherein the rational drug design and/or computational protein design is based on the interactions between one or more of residues (predictive active site) of the polypeptide of SEQ ID NO: 8 or 9 and linalool, 3-buten-2-ol, or 3-methyl-3-buten-2-ol.

Some embodiments provide for a method of preparing the crystal of the polypeptide of SEQ ID NO: 8 or 9, which comprises: (a) providing a solution having said polypeptide, in a suitable buffer such as about 10 mM Tris (about pH 9.0), about 350 mM NaCl, and about 2 mM dithothreitol (b) mixing equal volumes of the solution with a crystallization solution comprising about 61 mM MES+about 39 mM Imidazole (about pH 6.5), about 13.2% (w/v) PEG 8000; about 26.4% (v/v) ethylene glycol; about 20 mM each of L-Na-Glutamate; Alanine (racemic); Glycine; Lysine HCl (racemic); Serine (racemic) and, optionally, about 0.05% (v/v) 3-buten-2-ol; and (c) incubating the mixture under conditions to promote and for a time sufficient to produce the crystal of the polypeptide of SEQ ID NO:8.

Some embodiments provide for a method of preparing the co-crystal, which comprises the steps of: (a) providing a solution having said polypeptide, in a suitable buffer such as about 10 mM Tris (about pH 9.0), about 350 mM NaCl, and about 2 mM dithothreitol (b) mixing equal volumes of the solution with a crystallization solution comprising about 61 mM MES+about 39 mM Imidazole (about pH 6.5), about 13.2% (w/v) PEG 8000; about 26.4% (v/v) ethylene glycol; about 20 mM each of L-Na-Glutamate; Alanine (racemic); Glycine; Lysine HCl (racemic); Serine (racemic) and, optionally, about 0.05% (v/v) 3-buten-2-ol; and (c) incubating the mixture under conditions to promote and for a time sufficient to produce the co-crystal of said polypeptide bound to said substrate, such as linalool, 3-buten-2-ol, or 3-methyl-3-buten-2-ol.

Some embodiments provide for a method of identifying a compound that binds the polypeptide of SEQ ID NO:8 or 9, comprising: (a) obtaining a crystal comprising a protein consisting of SEQ ID NO: 9 wherein the crystal is in space group space group P2(1) with cell parameters a=88.7 Å, b=111.22 Å, c=120.42 Å; (b) determining the three-dimensional structure of said polypeptide by X-ray diffraction to obtain the atomic coordinates of Appendix 2; (c) contacting the polypeptide structure defined by the atomic coordinates of Appendix 2, or a subset thereof with a test compound; and (d) detecting an interaction between the compound and the atomic coordinates, wherein an energetically favored interaction between the test compound and the atomic coordinates is indicative of a compound that binds said polypeptide.

Some embodiments provide for the crystal, wherein the atomic coordinates define one or more regions as set forth in Table 3.

Some embodiments provide for a crystal, wherein the crystal is obtained from a polypeptide comprising SEQ ID NO: 8.

Some embodiments provide for a crystal comprising the coordinates of Appendix 1 or Appendix 2, preferably wherein the crystal is prepared from a polypeptide comprising SEQ ID NO:8.

Some embodiments provide for a crystal having the same tri-dimensional structure as any one of the tri-dimensional structures represented by the coordinates of Appendix 1 or Appendix 2, preferably wherein the crystal is prepared from a polypeptide comprising SEQ ID NO:8.

Some embodiments provide for a co-crystal comprising the crystal bound to a substrate, such as linalool, 3-buten-2-ol, and 3-methyl-3-buten-2-ol.

Some embodiments provide for a method of identifying a substrate or an inhibitor of a LDH, comprising any one or more of the steps of: (a) obtaining a crystal; (b) obtaining or determining the three-dimensional structure of said polypeptide using the crystal of (a) by an X-ray diffraction method; (c) displaying the three dimensional structure of said complex on a performing computer by inputting said crystal structure data of said polypeptide, wherein the performing computer comprises a computer program to generate said three dimensional structure and to identify a substrate or an inhibitor; and (d) selecting a substrate or an inhibitor of the active site of the polypeptide.

Some embodiments provide for a method for designing a LDH substrate or an inhibitor, the method comprising any one or more of the steps of: (a) obtaining a crystal, of a complex consisting of a polypeptide comprising SEQ ID NO:8 bound to the substrate or inhibitor at its binding location; (b) obtaining or determining the three dimensional structure of the complex using the crystal obtained in (a) by an X-ray diffraction method to obtain the atomic coordinates of the structure; (c) providing on a computer the atomic coordinates of the three dimensional structure of the complex; and (d) utilizing a program operated by the computer to design a chemical compound predicted to bind to the polypeptide comprising SEQ ID NO:8 at the substrate or inhibitor's binding location and either act as a substrate or inhibit the LDH, based on said three dimensional structure.

Some embodiments provide for a method, wherein the designing involves de novo rational drug design and/or computational protein design.

Some embodiments provide for a method, wherein the designing involves utilizing docking software and screening one or more databases for molecules that fit the substrate binding location on the polypeptide of comprising SEQ ID NO:8.

Some embodiments provide for a method, further comprising any one or more of: (e) synthesizing or obtaining the compound; and (f) evaluating the compound for its ability to perform one or more of (1) binding the polypeptide comprising SEQ ID NO:8, (2) competing with linalool, 3-buten-2-ol, or 3-methyl-3-buten-2-ol for binding the polypeptide comprising SEQ ID NO:8, (3) inhibiting LDH, or (4) being dehydrated by the polypeptide comprising SEQ ID NO:8.

Some embodiments provide for a method, wherein the rational drug design and/or computational protein design is based on the interactions between one or more of residues (predictive active site) of the polypeptide comprising SEQ ID NO:8 and linalool, 3-buten-2-ol, or 3-methyl-3-buten-2-ol.

Some embodiments provide a method of preparing a crystal, which comprises:
(a) providing a solution having said polypeptide, in a suitable buffer such as Tris about pH8 about 20 mM, NaCl about 150 mM, Glycerol about 5%; (b) mixing the solution with a crystallization solution comprising P8000 about 10%, Ethylene Glycol about 20%, Na-I-glutamate about 0.02M, dl-alanine about 0.02M, glycine about 0.02M, dl-lysine HCl about 0.02M, dl-serine about 0.02M; or
(a) providing a solution having said polypeptide, in a suitable buffer such as about 10 mM Tris (about pH 9.0), about 350 mM NaCl, and about 2 mM dithothreitol (b)

mixing equal volumes of the solution with a crystallization solution comprising about 61 mM MES+about 39 mM Imidazole (about pH 6.5), about 13.2% (w/v) PEG 8000; about 26.4% (v/v) ethylene glycol; about 20 mM each of L-Na-Glutamate; Alanine (racemic); Glycine; Lysine HCl (racemic); Serine (racemic) and, optionally, about 0.05% (v/v) 3-buten-2-ol; and (c) incubating the mixture under conditions to promote and for a time sufficient to produce the crystal.

Some embodiments provide for a method of preparing the co-crystal, which comprises the steps of: (a) providing a solution having said polypeptide, in a suitable buffer such as Tris about pH8 about 20 mM, NaCl about 150 mM, Glycerol about 5%; (b) mixing the solution with a crystallization solution comprising P8000 about 10%, Ethylene Glycol about 20%, Na-I-glutamate about 0.02M, dl-alanine about 0.02M, glycine about 0.02M, dl-lysine HCl about 0.02M, dl-serine about 0.02M; and (c) incubating the mixture under conditions to promote and for a time sufficient to produce the co-crystal of said polypeptide bound to said substrate, such as linalool, 3-buten-2-ol, or 3-methyl-3-buten-2-ol.

Some embodiments provide for a method of identifying a compound that binds a polypeptide comprising SEQ ID NO:8, comprising: (a) obtaining a crystal; (b) determining the three-dimensional structure of said polypeptide by X-ray diffraction to obtain the atomic coordinates of Appendix 1 or 2; (c) contacting the polypeptide structure defined by the atomic coordinates of Appendix 1 or 2, or a subset thereof with a test compound; and (d) detecting an interaction between the compound and the atomic coordinates, wherein an energetically favored interaction between the test compound and the atomic coordinates is indicative of a compound that binds said polypeptide.

Some embodiments provide for a method of improving one or more of the catalytic activities of a LDH, or a fragment thereof, the method comprising one or more of the following steps:
(a) obtaining a crystal as described in any of the previous paragraphs; (b) obtaining or determining the three dimensional structure of the LDH using the crystal obtained in (a) by, optionally, an X-ray diffraction method to obtain the atomic coordinates of the structure; (c) providing on a computer the atomic coordinates of the three dimensional structure of the complex; and (d) utilizing computational design, or a program operated by the computer to design a LDH, or a fragment thereof, with one or more improved catalytic activities, based on said three dimensional structure. In some embodiments, said coordinates comprise coordinates chosen from Appendix 1 and Appendix 2.

Some embodiments provide for a method for making an enzyme that has improved activity in the catalysis of the dehydration of 3-buten-2-ol to 1,3-butadiene and/or in the catalysis of the conversion of 3-methyl-3-buten-2-ol into isoprene comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative enzyme; producing the putative enzyme and confirming activity in the catalysis of the dehydration of 3-buten-2-ol to 1,3-butadiene and/or in the catalysis of the conversion of 3-methyl-3-buten-2-ol into isoprene. In some embodiments, said enzyme is improved from a LDH/cdLD disclosed herein.

Other objects, features and advantages of the disclosed methods, systems and compositions will become apparent from the following detailed description. It should be understood, however, that the detailed description and the specific examples, while indicating specific embodiments, are given by way of illustration only, since various changes and modifications within the spirit and scope of the inventions provided herein will become apparent to those skilled in the art from this detailed description.

BRIEF DESCRIPTION OF DRAWINGS

Those of skill in the art will understand that the drawings, described below, are for illustrative purposes only. The drawings are not intended to limit the scope of the present teachings in any way.

The patent or application file contains at least one drawing executed in color. Copies of this patent or patent application publication with color drawing(s) will be provided by the United States Patent and Trademark Office upon request and payment of the necessary fee.

FIG. 1: Overview of cdLD structural architecture, based on the high-resolution structure obtained by X-ray crystallography. FIG. 1A: pentameric symmetry arrangement observed in the crystal structure FIG. 1 B: cdLD monomer with secondary structure highlighted. Alpha helixes are in red, beta strands in yellow and loops in green. cdLD adopts a α/α(6) barrel fold. The innermost helixes of the barrel lining are labeled.

FIG. 3: Representation of cdLD's secondary structure (SEQ ID NO: 87) as assigned by the program DSSP and represented with Polyview. Helixes (□, 310 and □) are represented in red cylinders, strands with green arrows and loop in blue wire. Helices have been numbered consecutively from the N-terminal to the C-terminal.

FIG. 12: FIG. 12A, Butadiene production from 3-buten-2-ol (10 mM); and FIG. 12B, Isoprene production from 3-methyl-3-buten-2-ol (10 mM), by certain purified mutants.

FIG. 17: FIG. 17A, electron density associated with the putative active site of cdLD. Blue mesh is the 2Fo-Fc map at 1.5 sigma and in green is the Fo-Fc map at 3.0 sigma; FIG. 17B: cutaway ribbon and surface representation of the putative active site. The modeled zinc atom is a dark gray sphere and all amino acids within 6 Å of the zinc are displayed as stick structures. A black arrow indicates the position and direction of the narrow solvent-accessible channel.

DETAILED DESCRIPTION

Figure 2:
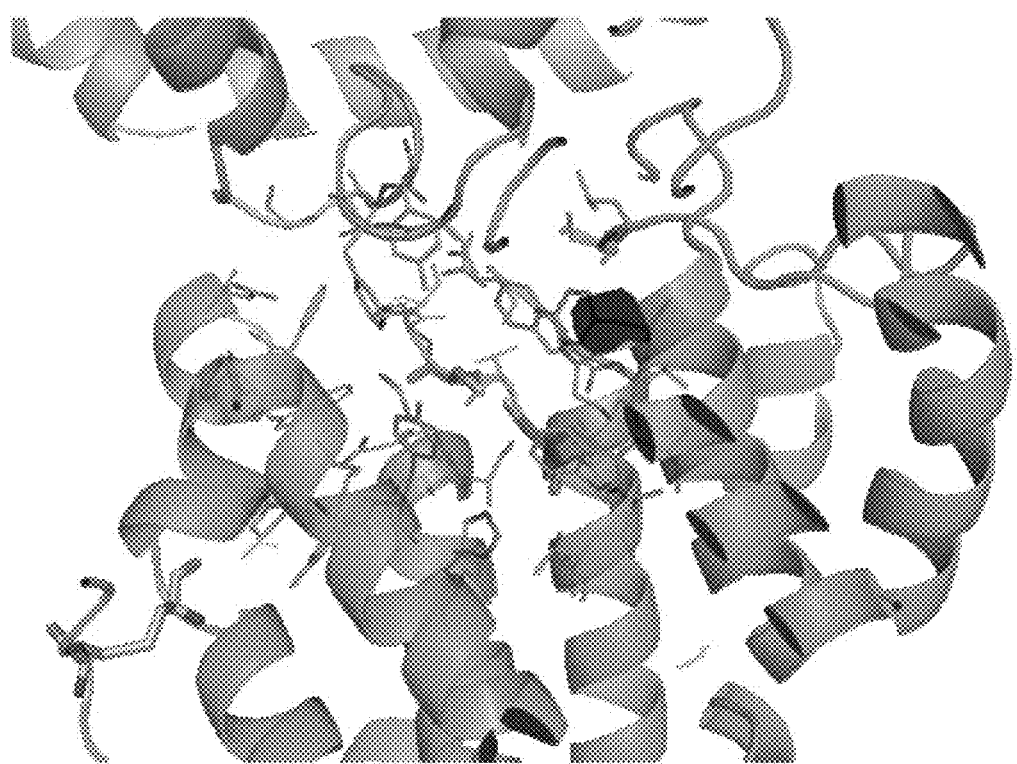
FIG. 2: Putative active site location at the interface between subunit A and subunit E. Green cartoon: chain A. Light brown: chain B. The side-chains lining the putative active site are in lined. Polar groups within the active site are colored in purple. Note the distal disulfide bridge (salmon sticks) on the left side of chain A. The view is oriented with the active site cavity entrance facing.

All references referred to are incorporated herein by reference in their entireties.

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In the present description and claims, the conventional one-letter and three-letter codes for amino acid residues are used. For ease of reference, the polypeptides described herein are described by use of the following nomenclature: Original amino acid(s):position(s):substituted amino acid(s) (e.g., A324L, where A is replaced with L at amino acid position 324). All the numbering is with reference to the numbering of wild-type polypeptide of SEQ ID NO:1

In the present description and claims, the activity of the claimed polypeptide is measured relative to that of the polypeptide of SEQ ID NO: NO:1, 4, 5, 7, or 8, unless otherwise specified. The numbering of the mutations of each disclosed polypeptide is determined relative to that of the protein of SEQ ID NO:1 (full length cdLD with two Methionines). The homology of the polypeptide to the wild-type cdLD of SEQ ID NO:1 is determined without taking into account the presence or lack of a periplasmic tag, the presence of one or two initial Methionines, and the presence or lack of a poly-His tag.

In some embodiments, numbers expressing quantities of ingredients, properties such as molecular weight, reaction conditions and results, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "butadiene," having the molecular formula $C_4H_6$ and a molecular mass of 54.09 g/mol (IUPAC name Buta-1,3-diene), is used interchangeably with 1,3-butadiene, biethylene, erythrene, divinyl, vinylethylene. Butadiene is a colorless, non-corrosive liquefied gas with a mild aromatic or gasoline-like odor. Butadiene is both explosive and flammable because of its low flash point.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present disclosure, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds, or deletes a single amino acid or a small percentage of amino acids in the encoded sequence is a "conservatively modified variant" when the alteration results in the substitution of an amino acid with a chemically similar amino acid. Thus, any number of amino acid residues can be so altered. Conservatively modified variants typically provide equivalent biological activity as the unmodified polypeptide sequence from which they are derived. Conservative substitution tables providing functionally similar amino acids, also referred herein as "equivalent amino acids" are well known in the art.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

As used herein, "consisting essentially of" means the inclusion of additional sequences to an object polynucleotide or polypeptide where the additional sequences do not materially affect the basic function of the claimed polynucleotide or polypeptide sequences.

"Codon optimization" is the process of modifying a nucleotide sequence in a manner that improves its expression, G/C content, RNA secondary structure, and translation in eukaryotic cells, without altering the amino acid sequence it encodes. Altered codon usage is often employed to alter translational efficiency and/or to optimize the coding sequence for expression in a desired host or to optimize the codon usage in a heterologous sequence for expression in a particular host. Codon usage in the coding regions of the polynucleotides of the present disclosure can be analyzed statistically using commercially available software packages such as "Codon Preference" available from the University of Wisconsin Genetics Computer Group. See, Devereaux, et al., (1984) Nucleic Acids Res. 12:387-395) or MacVector 4.1 (Eastman Kodak Co., New Haven, Conn.). Thus, the present disclosure provides a codon usage frequency characteristic of the coding region of at least one of the polynucleotides of the present disclosure. The number of polynucleotides (3 nucleotides per amino acid) that can be used to determine a codon usage frequency can be any integer from 3 to the number of polynucleotides of the present disclosure as provided herein. Optionally, the polynucleotides will be full-length sequences. An exemplary number of sequences for statistical analysis can be at least 1, 5, 10, 20, 50 or 100.

The term "crystal" means a structure (such as a three dimensional (3D) solid aggregate) in which the plane faces intersect at definite angles and in which there is a regular structure (such as internal structure) of the constituent chemical species. The term "crystal" refers in particular to a solid physical crystal form such as an experimentally-prepared crystal. Optionally, the crystal of cdLD may comprise one or more molecules which bind to cdLD's active site, or otherwise soaked into the crystal or cocrystallised with cdLD.

The term "derived" encompasses the terms "originated from", "obtained" or "obtainable from", and "isolated from".

"Equivalent amino acids" can be determined either on the basis of their structural homology with the amino acids for which they are substituted or on the results of comparative tests of biological activity between the various variants likely to be generated. As a non-limiting example, the list below summarizes possible substitutions often likely to be carried out without resulting in a significant modification of the biological activity of the corresponding variant:

1) Alanine (A), Serine (S), Threonine (T), Valine (V), Glycine (G), and Proline (P);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V) and
6) Phenylalanine (F), Tyrosine (Y), Tryptophan (W).

See also, Creighton, Proteins, W.H. Freeman and Co. (1984).

In making such changes/substitutions, the hydropathic index of amino acids may also be considered. The importance of the hydropathic amino acid index in conferring interactive biologic function on a protein is generally understood in the art (Kyte and Doolittle, (1982) J Mol Biol. 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In specific embodiments, the substitution is an alanine for the native amino acid at the recited position(s). Also encompassed are the nucleic acid sequence(s) encoding the variant protein or polypeptide.

"Endogenous" with reference to a polynucleotide or protein refers to a polynucleotide or protein that occurs naturally in the host cell.

As used herein, "expression" refers to the process by which a polypeptide is produced based on the nucleic acid sequence of a gene. The process includes both transcription and translation.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

Examples of routinely used "expression systems" include recombinant baculovirus, lentivirus, protozoa (e.g., eukaryotic parasite *Leishmania tarentolae*), microbial expression systems, including yeast-based (e.g. *Pichia pastoris, Saccharomyces cerevisiae, Yaerobia lipolytica, Hansenula polymorpha, Aspergillus* and *Trichoderma fungi*) and bacterial-based (e.g. *E. Coli, Pseudomonas fluorescens, Lactobacillus, Lactococcus, Bacillus megaterium, Bacillus Subtilis, Brevibacillus, Corynebacterium glutamicum*), Chinese hamster ovary (CHO) cells, CHOK1SVNSO (Lonza), BHK (baby hamster kidney), PerC.6 or Per.C6 (e.g., Percivia, Crucell), different lines of HEK 293, Expi293F™ cells (Life Technologies), GenScript's YeastHIGH™ Technology (GenScript), human neuronal precursor cell line AGE1.HN (Probiogen) and other mammalian cells, plants (e.g., corn, alfalfa, and tobacco), insect cells, avian eggs, algae, and transgenic animals (e.g., mice, rats, goats, sheep, pigs, cows). The advantages and disadvantages of these various systems have been reviewed in the literature and are known to one of ordinary skill in the art.

A "gene" refers to a DNA segment that is involved in producing a polypeptide and includes regions preceding and following the coding regions as well as intervening sequences (introns) between individual coding segments (exons).

"Host strain" or "host cell" means a suitable host for an expression vector or DNA construct comprising a polynucleotide encoding a polypeptide according to the disclosure. Specifically, host strains may be bacterial cells, mammalian cells, insect cells, and other cloning or "expression systems." In an embodiment of the disclosure, "host cell" means both the cells and protoplasts created from the cells of a microbial strain. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Heterologous" with reference to a polynucleotide or protein refers to a polynucleotide or protein/polypeptide that does not naturally occur in a host cell. In some embodiments, the protein is a commercially important industrial protein. It is intended that the term encompass proteins that are encoded by naturally occurring genes, mutated genes, and/or synthetic genes.

A polynucleotide or a polypeptide having a certain percent (e.g., at least 90%, 91%, 92%, 93%, 94%, 95%, 96%, 97%, 98%, or 99%) of sequence identity with another sequence means that, when aligned, that percentage of bases or amino acid residues are the same in comparing the two sequences. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA). This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al. (1988) Proc. Natl, Acad. Sci USA 85:2444-2448), and BLAST (BLAST Manual, Altschul et al., Nat'l Cent. Biotechnol. Inf., Natl Lib. Med. (NCIB NLM NIH), Bethesda, Md., and Altschul et al., (1997) NAR 25:3389-3402). Another alignment program is ALIGN Plus (Scientific and Educational Software, Pa.), using default parameters. Another sequence software program that finds use is the TFASTA Data Searching Program available in the Sequence Software Package Version 6.0 (Genetics Computer Group, University of Wisconsin, Madison, Wis.).

"Introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

The term "nucleic acid" encompasses DNA, cDNA, RNA, heteroduplexes, and synthetic molecules capable of encoding a polypeptide. RNA includes mRNA, RNA, RNAi, siRNA, cRNA and autocatalytic RNA. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. A nucleic acid comprises a nucleotide sequence which typically includes nucleotides that comprise an A, G, C, T or U base. However, nucleotide sequences may include other bases such as, without limitation inosine, methylycytosine, methylinosine, methyladenosine and/or thiouridine, although without limitation thereto.

One skilled in the art will recognize that nucleic acid sequences encompassed by the disclosure are also defined by the ability to hybridize under stringent hybridization conditions with nucleic acid sequences encoding the exemplified polypeptides. A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (Sambrook, et al. (Molecular cloning: a laboratory manual, Cold Spring Harbor Laboratory; 4th edition, 2012). Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10× Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe>100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

Stringent conditions may also be achieved with the addition of destabilizing agents such as formamide.

The term "operably linked" and its variants refer to chemical fusion or bonding or association of sufficient stability to withstand conditions encountered in the nucleotide incorporation methods utilized, between a combination of different compounds, molecules or other entities such as, but not limited to: between a mutant polymerase and a reporter moiety (e.g., fluorescent dye or nanoparticle); between a nucleotide and a reporter moiety (e.g., fluorescent dye); or between a promoter and a coding sequence, if it controls the transcription of the sequence.

A "promoter" is a regulatory sequence that is involved in binding RNA polymerase to initiate transcription of a gene. The promoter may be an inducible promoter or a constitutive promoter. An exemplary promoter used herein is a T7 promoter, which is an inducible promoter.

A "periplasmic tag" or "periplasmic leader sequence" is a sequence of amino acids which, when attached to/present at the N-terminus of a protein/peptide, directs the protein/peptide to the bacterial periplasm, where the sequence is often removed by a signal peptidase. Protein/peptide secretion into the periplasm can increase the stability of recombinantly-expressed proteins/peptides. An example of a periplasmic tag disclosed herein is provided as SEQ ID NO:3.

"Recombinant" when used in reference to a cell, nucleic acid, protein or vector, indicates that the cell, nucleic acid, protein or vector, has been modified by the introduction of a "heterologous nucleic acid" or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "signal sequence" or "signal peptide" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

"Selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

A structure that "substantially conforms" to a given set of atomic coordinates is a structure wherein at least about 50% of such structure has an RMSD of less than about 1.5 ANG for the backbone atoms in secondary structure elements in each domain, and more preferably, less than about 1.3 ANG for the backbone atoms in secondary structure elements in each domain, and, in increasing preference, less than about 1.0 ANG, less than about 0.7 ANG, less than about 0.5 ANG, and most preferably, less than about 0.3 ANG for the backbone atoms in secondary structure elements in each domain. In a more preferred embodiment, a structure that substantially conforms to a given set of atomic coordinates is a structure wherein at least about 75% of such structure has the recited RMSD value, and more preferably, at least about 90% of such structure has the recited RMSD value, and most preferably, about 100% of such structure has the recited RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein, "transformed cell" includes cells that have been transformed or transduced by use of recombinant DNA techniques. Transformation typically occurs by insertion of one or more nucleotide sequences into a cell. The inserted nucleotide sequence may be a "heterologous nucleotide sequence," i.e., is a sequence that is not natural to the cell that is to be transformed, such as a fusion protein.

As used herein, "transformed", "stably transformed", "transduced," and "transgenic" used in reference to a cell means the cell has a non-native (e.g., heterologous) nucleic acid sequence integrated into its genome or as an episomal plasmid that is maintained through multiple generations.

"Variants" refer to both polypeptides and nucleic acids. The term "variant" may be used interchangeably with the term "mutant." Variants include insertions, substitutions, transversions, truncations, and/or inversions at one or more locations in the amino acid or nucleotide sequence, respectively, of a parent sequence. Variant nucleic acids can include sequences that are complementary to sequences that are capable of hybridizing to the nucleotide sequences presented herein. For example, a variant sequence is complementary to sequences capable of hybridizing under stringent conditions (e.g., 50° C. and 0.2.×SSC (1×SSC=0.15 M NaCl, 0.015 M sodium citrate, pH 7.0)) to the nucleotide sequences presented herein. More particularly, the term variant encompasses sequences that are complementary to sequences that are capable of hybridizing under highly stringent conditions (e.g., 65° C. and 0.1×SSC) to the nucleotide sequences presented herein.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the claimed embodiments are intended to include such other forms of expression vectors, such as viral vectors (e.g., replication defective retroviruses, adenoviruses and adeno-associated viruses), which serve equivalent functions. Vectors also include cloning vectors, shuttle vectors, plasmids, phage particles, cassettes and the like.

Reference will now be made in detail to various disclosed embodiments.

Disclosed herein is the discovery that cdLD is capable of catalyzing the dehydration of 3-buten-2-ol to 1,3-butadiene. The positive results obtained for cdLD for the catalysis of this reaction along with the relatively low catalytic proficiency exhibited by this wild-type (WT) enzyme led to several attempts to improve the activity of cdLD. A crystal structure, or homology model is a significant help for enzyme optimization. However, a delta-BLAST search on the database of protein sequences from the Protein Data Bank (PDB) revealed that cdLD does not have any detectable homology to any sequence for which a structural model is available. Accordingly, this disclosure also unveils the crystal structure of apo cdLD, elucidated herein by X-ray crystallography. Crystals of purified apo cdLD were obtained, the tri-dimensional structure of this enzyme elucidated for the first time, and the results independently confirmed. An apo structure of cdLD was then successfully refined at 2.54 Å with an R value of R=21.6% and $R_{free}$=26.9%. Details of this procedure can be found in the Examples section of this disclosure.

The present disclosure has elucidated several domains within cdLD. cdLD crystallized in $P_21$ space group. cdLD adopts a pentameric arrangement with 5-fold axial symmetry in the asymmetric unit (labeled chain A through E). Each monomer adopts □/□(6) barrel fold, a relatively unusual fold that can be seen in FIG. 1. Apparent and noteworthy in the crystal structure, one disulfide bond is formed between Cys74 and Cys127 of each subunit (crystal structure numbering). A structural homology search using the DALI program yields a variety of structural homologs. Structural alignment between the cdLD monomer and some of the DALI hits reveals that the enzymes that are structurally homologous to cdLD all have their active sites in the "top" of the barrel with the catalytic residues supported by the innermost helixes that line up the inside of the barrel (helixes 4, 7, 9, 11, 13, 14) and the loops connecting these helixes to the outermost helixes from the barrel. Consistent with the other enzymes adopting a similar fold, cdLD presents a marked cleft in that same region whereas the rest of the subunit is tightly packed fully solvent exposed. Therefore, we hypothesized that the likely position of cdLD active site responsible for the observed catalytic activity is located in that region. Contrary to most of cdLD structural homologs, this putative active site is formed at the interface between subunits, for example, A and B in FIG. 1. Loop 62-77 (crystal structure numbering) from subunit B protrudes and closes the pocket formed by the top of the barrel of subunit A, see FIG. 2.

The elucidation of cdLD's crystal structure data allows for a better understanding of cdLD's enzymatic activity and the intelligent design of numerous improvements of the same, as well as the development of a variety of compounds that act either as substrates or inhibitors of cdLD or the polypeptides described herein.

In an embodiment, the disclosure has identified the catalytic residues of cdLD. Accordingly, the disclosure provides compounds that bind to the catalytic site of cdLD and which are identified using the structural data disclosed herein and/or any suitable method described herein. Candidate compounds identified using the structural data disclosed herein may be any suitable compound, including naturally occurring compounds, compounds designed de novo, library generated compounds, 3-butane-2-ol (3B2O) mimetics and analogs, and include organic compounds, new chemical entities, among others.

One skilled in the art may use one of several methods to screen entities (whether chemical or protein) for their ability to associate with cdLD or the polypeptides described herein. Specialized computer programs may also assist in the process of selecting entities. These include: GRID (Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (Miranker et al., "Functionality. Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (Kuntz et al., "A Geometric Approach to Macromolecule-Ligand Interactions", J. Mol. Biol., 161, pp. 269-288 (1982)). DOCK is available from University of California, San Francisco, Calif.

In another embodiment, the disclosure relates to a method of synthesizing or obtaining a candidate compound designed or screened for binding to cdLD or one of the polypeptides disclosed herein and then determining the ability of the candidate compound to interact with any one of those proteins.

In another embodiment, the disclosure relates to subsets of the atomic coordinates listed in Appendix I and subsets that conform substantially thereto. Preferred subsets define one or more regions of cdLD selected from those listed in Table 3 and FIG. 3.

The present invention also provides subsets of the atomic coordinates listed in Appendix I. The coordinates referred to herein include Cartesian coordinates derived from the mathematical equations related to the patterns obtained on diffraction of a monochromatic beam of X-ray by the atoms of a protein or protein complex in crystal form. The diffraction data are used to calculate an electron density map of the repeating units of the crystal. The electron density maps are then used to establish the positions of the individual atoms of the molecule or molecular complex. In an embodiment, there is provided a machine-readable data storage medium, comprising a data storage material encoded with machine readable data which, when used by a machine programmed with instructions for using said data, displays a graphical three-dimensional representation comprising cdLD or a polypeptide described herein.

It will be appreciated that a set of structure coordinates for a polypeptide is a relative set of points that define a shape in three dimensions. Thus, it is possible that an entirely different set of coordinates could define a similar or identical shape. Moreover, slight variations in the individual coordinates will have little effect on overall shape. Those sets of coordinates are also embodiments within the scope of this disclosure.

The variations in coordinates may be generated due to mathematical manipulations of the structure coordinates. For example, the structure coordinates set forth in Appendix I could be manipulated by crystallographic permutations of the structure coordinates, fractionalization of the structure coordinates, integer additions or subtractions to sets of the structure coordinates, inversion of the structure coordinates, or any combination thereof.

Alternatively, modification in the crystal structure due to mutations, additions, substitutions, and/or deletions of amino acids, or other changes in any of the components that make up the crystal could also account for variations in structure coordinates. Those variations are also embodiments within the scope of this disclosure.

In one embodiment, the structure coordinates set forth herein can also be used to aid in obtaining structural information about another crystallized molecule or molecular complex. This may be achieved by any of a number of well-known techniques, including molecular replacement. For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth herein as a molecular replacement model.

By using molecular replacement, all or part of the structure coordinates of cdLD provided by the present disclosure (and set forth in the attached figures) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure. Thus, this method involves generating a preliminary model of a molecule or molecular complex whose structure coordinates are unknown, by orienting and positioning the relevant portion of cdLD according to the enclosed figures within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in Meth. Enzymol., 115, pp. 55-77 (1985); Rossmann, ed., "The Molecular Replacement Method", Int. Sci. Rev. Ser., No. 13, Gordon & Breach, New York (1972)).

The structure coordinates of cdLD as provided by the present disclosure are useful in solving the structure of polypeptides that have amino acid substitutions, additions and/or deletions as compared to naturally occurring cdLD. These polypeptides may optionally be crystallized in co-complex with a ligand, such as an inhibitor or substrate analogue. The crystal structures of a series of such complexes may then be solved by molecular replacement and compared with that of cdLD. Potential sites for modification within the various binding sites of the enzyme may thus be identified. This information provides an additional tool for determining the most efficient binding interactions such as, for example, increased hydrophobic interactions, between cdLD and a ligand. It is noted that the ligand may be the protein's natural ligand or may be a potential substrate or inhibitor of the protein.

In the present description and claims, newly disclosed polypeptides that have improved activity in the catalysis of the dehydration of 3-buten-2-ol to 1,3-butadiene and/or in the catalysis of 3-methyl-3-buten-2-ol to isoprene are disclosed and claimed. In some embodiments, said improvement can be observed in vivo. In other embodiments, said improvement can be observed in the purified polypeptide, in which case the improvement is referred to as an improvement in specific activity. In some embodiments, it is envisioned that the improved polypeptides would show said improved activity whether or not they have a periplasmic tag and/or a C-terminal poly-His tag. In other embodiments, it is also envisioned that the improved polypeptides would show said improved activity when compared to cdLD of SEQ ID NO:1, 4, 5, 7, or 8. It is to be understood that conservatively modified variants of the polypeptides specified herein also fall within the scope of this disclosure.

The following discusses the relationship between mutations that may be present in the polypeptides provided herein, and desirable alterations in properties (relative to those of the wild-type polypeptide of SEQ ID NO:1, 4, 5, 7, or 8).

Improved in vivo Activity in the Catalysis of the Dehydration of 3-buten-2-ol to 1,3-butadiene Some embodiments provide polypeptides with improved activity in the catalysis of the dehydration of 3-buten-2-ol to 1,3-butadiene, relative to the polypeptide of SEQ ID NO:1, 4, 5, 7, or 8. Improved activity in the catalysis of the dehydration of 3-buten-2-ol to 1,3-butadiene can be measured by any method known to one of ordinary skill in the art. In one embodiment, improved activity in the catalysis of the dehydration of 3-buten-2-ol to 1,3-butadiene of a polypeptide described herein refers to an increased activity in the catalysis of the dehydration of 3-buten-2-ol to 1,3-butadiene of a bacterial cell culture expressing said polypeptide, relative to a bacterial cell extract expressing a wild-type polypeptide of SEQ ID NO: 1, 4, 5, 7, or 8.

In some embodiments, the activity in the catalysis of the dehydration of 3-buten-2-ol to 1,3-butadiene is at least 80% of that of a polypeptide consisting of SEQ ID NO:1, 4, 5, 7, or 8, increased about 1.5 fold or greater when compared to that of a polypeptide consisting of SEQ ID NO: 1, 4, 5, 7, or 8, preferably about 2 fold or greater when compared to that of a polypeptide consisting of SEQ ID NO:1, 4, 5, 7, or 8, preferably about 2.5 fold or greater when compared to that of a polypeptide consisting of SEQ ID NO:1, 4, 5, 7, or 8, preferably about 3 fold or greater when compared to that of a polypeptide consisting of SEQ ID NO:1, 4, 7, or 8, preferably about 3.5 fold or greater when compared to that of a polypeptide consisting of SEQ ID NO:1, 4, 5, 7, or 8, preferably about 4 fold or greater when compared to that of a polypeptide consisting of SEQ ID NO: SEQ ID NO:1, 4, 5, 7, or 8, preferably about 4.5 fold or greater when compared to that of a polypeptide consisting of SEQ ID NO:1, 4, 5, 7, or 8, or preferably about 5 fold or greater when compared to that of a polypeptide consisting of SEQ ID NO: 1, 4, 5, 7, or 8, and wherein said activity is observed in at least one activity assay.

In some embodiments, the increase in the catalysis of the dehydration of 3-buten-2-ol to 1,3-butadiene is observed in at least one type of non-bacterial cells expressing a polypeptide of SEQ ID NO: 1, 4, 5, 7, or 8. In some embodiments, the increased in the catalysis of the dehydration of 3-buten-2-ol to 1,3-butadiene is observed in at least one type of bacteria. In some embodiments, the increased in the catalysis of the dehydration of 3-buten-2-ol to 1,3-butadiene is observed in more than one type of bacteria. In some embodiments, the bacteria are a strain of E. Coli. In some embodiments, the bacteria are Origami2(DE3). In some embodiments, the bacteria are BL21(DE3).

Improved Specific Activity in the Catalysis of the Dehydration of 3-buten-2-ol to 1,3-butadiene Some embodiments provide polypeptides with improved specific activity in the catalysis of the dehydration of 3-buten-2-ol to 1,3-butadiene, relative to the polypeptide of SEQ ID NO:1, 4, 5, 7, or 8. Improved specific activity in the catalysis of the dehydration of 3-buten-2-ol to 1,3-butadiene can be measured by any method known to one of ordinary skill in the art. In one embodiment, improved specific activity in the catalysis of the dehydration of 3-buten-2-ol to 1,3-butadiene of a polypeptide described herein refers to an increased specific activity in the catalysis of the dehydration of 3-buten-2-ol to 1,3-butadiene of the purified polypeptide, relative to that of the purified polypeptide of SEQ ID NO:1, 4, 5, 7, or 8.

In some embodiments, the specific activity in the catalysis of the dehydration of 3-buten-2-ol to 1,3-butadiene is at least 80% of that of a polypeptide consisting of SEQ ID NO:1, 4, 5, 7, or 8, increased about 1.5 fold or greater when compared to that of a polypeptide consisting of SEQ ID NO:1, 4, 5, 7, or 8, preferably about 2 fold or greater when compared to that of a polypeptide consisting of SEQ ID NO:1, 4, 5, 7, or 8, preferably about 2.5 fold or greater when compared to that of a polypeptide consisting of SEQ ID NO:1, 4, 5, 7, or 8, preferably about 3 fold or greater when compared to that of a polypeptide consisting of SEQ ID NO:1, 4, 5, 7, or 8, preferably about 3.5 fold or greater when compared to that of a polypeptide consisting of SEQ ID NO: 1, 4, 5, 7, or 8, preferably about 4 fold or greater when compared to that of a polypeptide consisting of SEQ ID NO:1, 4, 5, 7, or 8, preferably about 4.5 fold or greater when compared to that of a polypeptide consisting of SEQ ID NO:1, 4, 5, 7, or 8, or preferably about 5 fold or greater when compared to that of a polypeptide consisting of SEQ ID NO:1, 4, 5, 7, or 8, and wherein said activity is observed in at least one specific activity assay.

In some embodiments, the increase in the catalysis of the dehydration of 3-buten-2-ol to 1,3-butadiene is observed in polypeptides purified from at least one type of non-bacterial cells expressing a polypeptide of SEQ ID NO:1, 4, 5, 7, or 8. In some embodiments, the increased in the catalysis of the dehydration of 3-buten-2-ol to 1,3-butadiene is observed in polypeptides purified from at least one type of bacteria. In some embodiments, the increased in the catalysis of the dehydration of 3-buten-2-ol to 1,3-butadiene is observed in polypeptides purified from more than one type of bacteria. In some embodiments, the bacteria are a strain of E. Coli. In some embodiments, the bacteria are Origami2(DE3). In some embodiments, the bacteria are BL21(DE3).

It will be understood that additional embodiments encompass polypeptides where it may be advantageous to introduce additional point-mutations (e.g., deletions, insertions, inversions, substitutions) in any of the polypeptides described herein.

Any of the polypeptides described herein may either contain or lack a N-terminal periplasmic tag. In some embodiments, the periplasmic tag (SEQ ID NO:3) is the sequence underlined in the protein of SEQ ID NO:1. In one embodiment, the polypeptide may contain a C-terminal tag. In some embodiments, the C-terminal tag is a poly-Histidine tag consisting of six Histidines (SEQ ID NO: 10), with or without additional amino acids, as in SEQ ID NO:4 and 5. In some embodiments, the polypeptide contains both a periplasmic tag and a C-terminal tag. In some embodiments, the polypeptide contains only a periplasmic tag. In some embodiments, the polypeptide contains a C-terminal tag. In any of these embodiments, the C-terminal tag can be a poly-Histidine tag. In some embodiments, the C-terminal tag is that of SEQ ID NO:6.

In one embodiment, the amino acid sequence of the polypeptide is that of any one of the polypeptides listed in the listing of sequences in the Examples section. In related embodiments, the polypeptide lacks the poly-His tag. In related embodiments, the polypeptide lacks the periplasmic tag. In related embodiments, the polypeptide lacks the periplasmic tag and the poly-His tag, which can be that of SEQ ID NO:6 or just HHHHHH (His6) (SEQ ID NO: 10).

Derivatives of the polypeptides disclosed herein are also provided.

In one embodiment, derivative polypeptides are polypeptides that have been altered, for example by conjugation or complexing with other chemical moieties, by post-translational modification (e.g. phosphorylation, acetylation and the like), modification of glycosylation (e.g. adding, removing or altering glycosylation), and/or inclusion/substitution of additional amino acid sequences as would be understood in the art.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. poly-histidine) fusion partners, maltose binding protein (MBP), Protein A, glutathione S-transferase (GST), fluorescent protein sequences (e.g. GFP), epitope tags such as myc, FLAG, and haemagglutinin tags.

Other derivatives contemplated by the embodiments include, but are not limited to, modification to side chains, incorporation of unnatural amino acids and/or their derivatives during peptide, or protein synthesis and the use of crosslinkers and other methods which impose conformational constraints on the disclosed polypeptides and fragments thereof.

The embodiments also encompass nucleic acid molecules encoding relatives of the disclosed polypeptides. "Relatives" of the disclosed polypeptide-encoding nucleic acid sequences include those sequences that encode the polypeptides disclosed herein but that differ conservatively because of the degeneracy of the genetic code. Allelic polypeptides that later develop through culture can be identified with the use of well-known molecular biology techniques, such as polymerase chain reaction (PCR) and hybridization techniques as outlined below. Relative nucleic acid sequences also include synthetically derived nucleic acid sequences that have been generated, for example, by using site-directed mutagenesis but which still encode the polypeptides disclosed.

The skilled artisan will further appreciate that changes can be introduced by mutation of the nucleic acid sequences thereby leading to changes in the amino acid sequence of the encoded polypeptides, without altering the biological activity of the proteins. Thus, relative nucleic acid molecules can be created by introducing one or more nucleotide substitutions, nucleotide additions and/or nucleotide deletions into the corresponding nucleic acid sequence disclosed herein, such that one or more amino acid substitutions, amino acid additions or amino acid deletions are introduced into the encoded protein. Mutations can be introduced by standard techniques, such as site-directed mutagenesis and PCR-mediated mutagenesis. Such relative nucleic acid sequences are also encompassed by the present embodiments.

Alternatively, variant nucleic acid sequences can be made by introducing mutations randomly along all or part of the coding sequence, such as by saturation mutagenesis and the resultant mutants can be screened for ability to confer improved activity or increased specific activity in the catalysis of the dehydration of 3-buten-2-ol to 1,3-butadiene to identify mutants that retain the improved activity of the polypeptides described herein. Following mutagenesis, the encoded protein can be expressed recombinantly, and the activity of the protein can be determined using standard assay techniques, including those described herein.

Nucleic Acids

With the polypeptide disclosed herein and their amino acid sequence as disclosed herein, the skilled person may determine suitable polynucleotides that encode those polypeptides. Those having ordinary skill in the art will readily appreciate that due to the degeneracy of the genetic code, a multitude of nucleotide sequences encoding the polypeptides described herein exist. The sequence of the polynucleotide gene can be deduced from a polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Furthermore, synthetic variant polynucleotide sequences encoding the polypeptides as described herein can be designed so that they will be expressed in any cell type, prokaryotic or eukaryotic.

Accordingly, some embodiments relate to polynucleotides either comprising or consisting essentially of a nucleic acid sequence encoding a polypeptide as described above and elsewhere herein. In some embodiments, the nucleic acid sequence is a DNA sequence (e.g., a cDNA sequence). In other embodiments, the nucleic acid sequence is a RNA sequence. In some embodiments, the nucleic acid is a cDNA encoding any of the polypeptides described herein. The nucleotide sequences encoding the polypeptide may be prepared by any suitable technologies well known to those skilled in the art, including, but not limited to, recombinant DNA technology and chemical synthesis. Synthetic polynucleotides may be prepared using commercially available automated polynucleotide synthesizers.

One aspect pertains to isolated or recombinant nucleic acid molecules comprising nucleic acid sequences encoding the polypeptides described herein or biologically active portions thereof, as well as nucleic acid molecules sufficient for use as hybridization probes to identify nucleic acid molecules encoding proteins with regions of sequence homology to the polypeptides described herein. Nucleic acid molecules that are fragments of these nucleic acid sequences encoding polypeptides are also encompassed by the embodiments. By "fragment" is intended a portion of the nucleic acid sequence encoding a portion of a polypeptide. In some embodiments, a fragment of a nucleic acid sequence may encode a biologically active portion of a polypeptide or it may be a fragment that can be used as a hybridization probe or PCR primer using methods well known to one of ordinary skill in the art.

In some embodiments, the nucleic acid has been codon optimized for expression of any one of the polypeptides described herein.

In other embodiments, the nucleic acid is a probe, which may be a single or double-stranded oligonucleotide or polynucleotide, suitably labeled for the purpose of detecting complementary sequences of polynucleotides encoding the polypeptides described herein, such as in arrays, Northern, or Southern blotting. Methods for detecting labeled nucleic acids hybridized to an immobilized nucleic acid are well known to practitioners in the art. Such methods include autoradiography, chemiluminescent, fluorescent and colorimetric detection.

In some embodiments, the polynucleotide comprises a sequence encoding any one of the polypeptides described herein operably linked to a promoter sequence. Constitutive or inducible promoters as known in the art are contemplated herein. The promoters may be either naturally occurring promoters, or hybrid promoters that combine elements of more than one promoter. Non-limiting examples of promoters include SV40, cytomegalovirus (CMV), and HIV-1 LTR promoters.

In some embodiments, the polynucleotide comprises a sequence encoding any one of the polypeptides described herein operably linked to a sequence encoding another protein, which can be a fusion protein or another protein separated by a linker. In some embodiments, the linker has a protease cleavage site, such as for Factor Xa or Thrombin, which allow the relevant protease to partially digest the fusion polypeptide described herein and thereby liberate the recombinant polypeptide therefrom. The liberated polypeptide can then be isolated from the fusion partner by, for example, subsequent chromatographic separation. In some embodiments, the polynucleotide comprises a sequence encoding any one of the polypeptides described herein operably linked to both a promoter and a fusion protein.

Some other embodiments provide genetic constructs in the form of, or comprising genetic components of, a plasmid, bacteriophage, a cosmid, a yeast or bacterial artificial chromosome, as are well understood in the art. Genetic constructs may be suitable for maintenance and propagation of the isolated nucleic acid in bacteria or other host cells, for manipulation by recombinant DNA technology and/or expression (expression vectors) of the nucleic acid or an encoded polypeptide as described herein.

Some other embodiments relate to recombinant expression vectors comprising a DNA sequence encoding one or more of the polypeptides described herein. In some embodiments, the expression vector comprises one or more of said DNA sequences operably linked to a promoter. Suitably, the expression vector comprises the nucleic acid encoding one of the polypeptides described herein operably linked to one or more additional sequences. In some embodiments, the expression vector may be either a self-replicating extrachromosomal vector such as a plasmid, or a vector that integrates into a host genome. Non-limiting examples of viral expression vectors include adenovirus vectors, adeno-associated virus vectors, herpes viral vectors, retroviral vectors, lentiviral vectors, and the like. For example, adenovirus vectors can be first, second, third, and/or fourth generation adenoviral vectors or gutless adenoviral vectors. Adenovirus vectors can be generated to very high titers of infectious particles, infect a great variety of cells, efficiently transfer genes to cells that are not dividing, and are seldom integrated in the host genome, which avoids the risk of cellular transformation by insertional mutagenesis. The vector may further include sequences flanking the polynucleotide giving rise to RNA which comprise sequences homologous to eukaryotic genomic sequences or viral genomic sequences. This will allow the introduction of the polynucleotides described herein into the genome of a host cell.

An integrative cloning vector may integrate at random or at a predetermined target locus in the chromosome(s) of the host cell into which it is to be integrated.

Specific embodiments of expression vectors can be found elsewhere in this disclosure (see below).

Some other embodiments relate to host cells comprising a DNA molecule encoding a polypeptide as described herein. In some embodiments, these host cells can be described as expression systems. Suitable host cells for expression may be prokaryotic or eukaryotic. Without limitation, suitable host cells may be mammalian cells (e.g. HeLa, HEK293T, Jurkat cells), yeast cells (e.g. *Saccharomyces cerevisiae*), insect cells (e.g. Sf9, *Trichoplusia ni*) utilized with or without a baculovirus expression system, or bacterial cells, such as *E. coli* (Origami2(DE3), BL21 (DE3)), or a *Vaccinia* virus host. Introduction of genetic constructs into host cells (whether prokaryotic or eukaryotic) is well known in the art, as for example described in Current Protocols in Molecular Biology Eds. Ausubel et al., (John Wiley & Sons, Inc. current update Jul. 2, 2014).

A further embodiment relates to a transformed or transduced organism, such as an organism selected from plant and insect cells, bacteria, yeast, baculovirus, protozoa, nematodes, algae, and transgenic mammals (mice, rats, pigs, etc.). The transformed organism comprises a DNA molecule of the embodiments, an expression cassette comprising the DNA molecule or a vector comprising the expression cassette, which may be stably incorporated into the genome of the transformed organism.

Methods for Preparing the Polypeptides

The polypeptides described herein (inclusive of fragments and derivatives) may be prepared by any suitable procedure known to those of skill in the art. In some embodiments, the protein is a recombinant protein.

By way of example only, a recombinant polypeptide may be produced by a method including the steps of: (i) preparing an expression construct which comprises a nucleic acid expressing one or more of the polypeptides described herein, operably linked to one or more regulatory nucleotide sequences; (ii) transfecting or transforming a suitable host cell with the expression construct; (iii) expressing a recombinant polypeptide/protein in said host cell; and (iv) isolating the recombinant polypeptide/protein from said host cell or using the resultant host cell as is or as a cell extract.

Several methods for introducing mutations into genes, cDNA, and other polynucleotides are known in the art, including the use of proprietary library generation methods that are commercially available. The DNA sequence encoding a wild-type polypeptide of SEQ ID NO:1 (with or without one of the first of the two Met) may be isolated from any cell or microorganism producing the polypeptide in question, using various methods well known in the art. In one embodiment, the cDNA encoding the wild-type polypeptide of SEQ ID NO:1 (with or without one of the first two Met) is obtained from *Castellaniella defragrans* cells, cDNA libraries, or the like.

In one embodiment, the mutations are introduced into a wild-type polypeptide of SEQ ID NO:1 (or SEQ ID NO:1 without the periplasmic tag, or SEQ ID NO:4, or 5) using Site-Directed Mutagenesis. Once a wild-type polypeptide-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the polypeptide-encoding sequence, is created in a vector carrying the gene encoding wild-type polypeptide of SEQ ID NO:1 (or SEQ ID NO:1 without the periplasmic tag, or SEQ ID NO:4, or 5). Then the synthetic nucleotide, bearing the desired mutation, is annealed to a homologous portion of the single-stranded DNA. The remaining gap is then filled in with DNA polymerase I (Klenow fragment) and the construct is ligated using T4 ligase.

Another embodiment for introducing mutations into wild-type polypeptide of SEQ ID NO:1 (or SEQ ID NO:1 without the periplasmic tag, or SEQ ID NO:4, or 5)-encoding DNA sequences involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of the Polypeptides

, In one embodiment, the polypeptides are expressed according to the methods described in the Examples section of this disclosure. According to some other embodiments, a DNA sequence encoding the polypeptide produced by methods described above, or produced by any alternative methods known in the art, can be expressed, in enzyme form, using an expression vector, which typically includes control sequences encoding a promoter, operator, ribosome binding site, translation initiation signal, and, optionally, a repressor gene or various activator genes. For each combination of a promoter and a host cell, culture conditions are available which are conducive to the expression the DNA sequence encoding the desired polypeptide. After reaching the desired cell density or titre of the polypeptide the culture is stopped and the polypeptide is recovered using known procedures. Alternatively, the host cell is used directly (e.g., pellet, suspension), i.e., without isolation of the recombinant protein.

The recombinant expression vector carrying the DNA sequence encoding a polypeptide as described herein may be any vector, which may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, minichromosome, or an artificial chromosome. Alternatively, the vector may be one which, when introduced into a host cell, is integrated into the host cell genome and replicated together with the chromosome(s) into which it has been integrated.

In the vector, the DNA sequence typically is operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding a polypeptide as described herein, especially in a bacterial host, are the promoter of the lac operon of *E. coli*, the *Streptomyces coelicolor* agarase gene dagA promoters, the promoters of the *Castellaniella defragrans*, and others. For transcription in a fungal host, examples of useful promoters are those derived from the gene encoding *A. oryzae* TAKA amylase, *Rhizomucor miehei* aspartic proteinase, *A. niger* neutral LDH, *A. niger* acid stable LDH, *A. niger* glucoamylase, *Rhizomucor miehei* lipase, *A. oryzae* alkaline protease, *A. oryzae* triose phosphate isomerase or *A. nidulans* acetamidase. The promoters can be selected based on the desired outcome. The nucleic acids can be combined with constitutive, tissue-preferred, inducible, or other promoters for expression in the host cell or organism. The above list of promoters is not meant to be limiting. Any appropriate promoter can be used in the embodiments.

In some embodiments, the expression vector described may also comprise a suitable transcription terminator and, in eukaryotes, polyadenylation sequences operably connected to the DNA sequence encoding the polypeptide as described herein. Termination and polyadenylation sequences may suitably be derived from the same sources as the promoter or not.

In some embodiments, the vector may further comprise a DNA sequence enabling the vector to replicate in the host cell in question. Examples of such sequences are the origins of replication of plasmids pUC19, pACYC177, pUB110, pE194, pAMB1 and pIJ702. The above list of origins of replication is not meant to be limiting. Any appropriate origins of replication can be used in the embodiments In some embodiments, the vector may also comprise a selectable marker. Selectable marker genes are utilized for the selection of transformed cells or tissues, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation. The above list of selectable marker genes is not meant to be limiting. Any selectable marker gene can be used in the embodiments.

Appropriate culture mediums and conditions for the above-described host cells are known in the art. While intracellular expression may be advantageous in some respects, e.g., when using certain bacteria as host cells, it is often preferred that the expression is extracellular or periplasmic. In some embodiments, the *Castellaniella defragrans* LDHs mentioned herein comprise a pre-region/signal/leader sequence permitting secretion of the expressed protease into the culture medium or periplasm. If desirable, this pre-region may be replaced by a different preregion or signal sequence, conveniently accomplished by substitution of the DNA sequences encoding the respective preregions.

The procedures used to ligate the DNA construct encoding a disclosed polypeptide, the promoter, terminator and other elements, respectively, and to insert them into suitable vectors containing the information necessary for replication, are well known to persons skilled in the art (cf., for instance, Sambrook et al., Molecular Cloning: A Laboratory Manual, supra).

In one embodiment, the cells disclosed herein, either comprising a DNA construct or an expression vector as defined above, are advantageously used as host cells in the recombinant production of a polypeptide as described herein. The cell may be transformed with the DNA construct encoding the polypeptide as described herein, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

In some embodiments, a cell as described herein may be a cell of a higher organism such as a mammal or an insect, a microbial cell, e.g., a bacterial or a fungal (including yeast) cell, or the like.

Without limitation, examples of suitable bacteria are *Castellaniella defragrans*, gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gram negative bacteria such as *E. coli*. In one embodiment, the transformation of the bacteria may, for instance, be effected by protoplast transformation or by using competent cells in a manner known per se.

In some other embodiments, a yeast organism may be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. Suitable procedure for transformation fungal host cells are well known in the art.

In yet a further set of embodiments, the present disclosure relates to a method of producing a polypeptide as described herein, which method comprises cultivating a host cell as described above under conditions conducive to the production of the polypeptide and recovering the polypeptide from the cells and/or culture medium. In some embodiments, the cells are cultured under aerobic conditions. In other embodiments, the cells are cultured under anerobic conditions.

The medium used to cultivate the cells may be any conventional medium suitable for growing the host cell in question and obtaining expression of the polypeptide as described herein. Suitable media are available from commercial suppliers or may be prepared according to published recipes (e.g., as described in catalogues of the American Type Culture Collection).

Purification of the Polypeptides

The polypeptide described herein and secreted from the host cells may conveniently be recovered from the culture medium by well-known procedures, in addition to those described in the Examples section of this disclosure, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

For example, fermentation, separation, and concentration techniques are known in the art and conventional methods can be used in order to prepare the concentrated polypeptide-containing solution. After fermentation, a fermentation broth is obtained, and the microbial cells and various suspended solids, including residual raw fermentation materials, are removed by conventional separation techniques to obtain a polypeptide solution. Filtration, centrifugation, microfiltration, rotary vacuum drum filtration, followed by ultra-filtration, extraction or chromatography, or the like are generally used.

In some instances, it is desirable to concentrate the solution containing the polypeptide to optimize recovery, since the use of unconcentrated solutions requires increased incubation time to collect precipitates containing the purified polypeptide. The solution is concentrated using conventional techniques until the desired enzyme level is obtained. Concentration of the enzyme polypeptide containing solution may be achieved by any of the techniques discussed above. In one embodiment, rotary vacuum evaporation and/or ultrafiltration is used.

In one embodiment, a "precipitation agent" for purposes of purification is meant to be a compound effective to precipitate the polypeptide from the concentrated enzyme polypeptide solution in solid form, whatever its nature may be, i.e., crystalline, amorphous, or a blend of both. Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative.

In one embodiment, a metal halide precipitation agent is used in an amount effective to precipitate the polypeptide. The selection of at least an effective amount and an optimum amount of metal halide effective to cause precipitation of the enzyme polypeptide, as well as the conditions of the precipitation for maximum recovery including incubation time, pH, temperature and concentration of polypeptide, will be readily apparent to one of ordinary skill in the art after routine testing.

In some embodiments, at least about 5% w/v (weight/volume) to about 25% w/v of metal halide is added to the concentrated enzyme polypeptide solution, and usually at least 8% w/v. In some embodiments, no more than about 25% w/v of metal halide is added to the concentrated enzyme polypeptide solution and usually no more than about 20% w/v. The optimal concentration of the metal halide precipitation agent will depend, among others, on the nature of the specific polypeptide and on its concentration in the concentrated polypeptide solution.

Another alternative embodiment to effect precipitation of the enzyme is to use of organic compounds, which can be added to the concentrated enzyme polypeptide solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

In some embodiments, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. In some embodiments, the organic compound precipitations agents can be for example linear or branched alkyl esters of 4-hydroxybenzoic acid, wherein the alkyl group contains from 1 to 10 carbon atoms, and blends of two or more of these organic compounds. In some embodiments, suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents.

In some embodiments, addition of the organic compound precipitation agent provides the advantage of high flexibility of the precipitation conditions with respect to pH, temperature, polypeptide concentration, precipitation agent concentration, and time of incubation.

In some embodiments, the organic compound precipitation agent is used in an amount effective to improve precipitation of the enzyme polypeptide by means of the metal halide precipitation agent. The selection of at least an effective amount and an optimum amount of organic compound precipitation agent, as well as the conditions of the precipitation for maximum recovery including incubation time, pH, temperature and concentration of enzyme polypeptide, will be readily apparent to one of ordinary skill in the art, in light of the present disclosure, after routine testing.

In some embodiments, at least about 0.01% w/v of organic compound precipitation agent is added to the concentrated enzyme polypeptide solution and usually at least about 0.02% w/v. In some embodiments, no more than about 0.3% w/v of organic compound precipitation agent is added to the concentrated enzyme polypeptide solution and usually no more than about 0.2% w/v.

In some embodiments, the concentrated enzyme polypeptide solution, containing the metal halide precipitation agent and, in one aspect, the organic compound precipitation agent, is adjusted to a pH that necessarily will depend on the enzyme polypeptide to be purified. In some embodiments, the pH is adjusted to a level near the isoelectric point (pI) of the polypeptide. For example, the pH can be adjusted within a range of about 2.5 pH units below the pI to about 2.5 pH units above the pI.

The incubation time necessary to obtain a purified enzyme polypeptide precipitate depends on the nature of the specific enzyme polypeptide, the concentration of enzyme, and the specific precipitation agent(s) and its (their) concentration. In some embodiments, the time effective to precipitate the enzyme polypeptide is between about 1 to about 30 hours; usually it does not exceed about 25 hours. In the presence of the organic compound precipitation agent, the time of incubation can still be reduced to less than about 10 hours, and in most cases even about 6 hours.

In some embodiments, the temperature during incubation is between about 4° C. and about 50° C. In some embodiments, the method is carried out at a temperature between about 10° C. and about 45° C., and particularly between about 20° C. and about 400° C. The optimal temperature for inducing precipitation varies according to the solution conditions and the enzyme polypeptide or precipitation agent(s) used.

In some embodiments, the overall recovery of purified enzyme polypeptide precipitate, and the efficiency with which the process is conducted, is improved by agitating the solution comprising the enzyme polypeptide, the added metal halide and the added organic compound. In some embodiments, the agitation step is done both during addition of the metal halide and the organic compound, and during the subsequent incubation period. Suitable agitation methods include mechanical stirring or shaking, vigorous aeration, or any similar technique.

In some embodiments, after the incubation period, the purified enzyme polypeptide is then separated from the impurities and collected by conventional separation techniques, such as filtration, centrifugation, microfiltration, rotary vacuum filtration, ultrafiltration, press filtration, cross membrane microfiltration, cross flow membrane microfiltration or the like. Cross membrane microfiltration can be one method used. In some embodiments, further purification of the purified enzyme polypeptide precipitate can be obtained by washing the precipitate with water. For example, the purified enzyme polypeptide precipitate is washed with water containing the metal halide precipitation agent, for example, with water containing the metal halide and the organic compound precipitation agents.

Compositions

Some embodiments relate to compositions comprising one or more disclosed polypeptides alone or in combination, including in combination with wild type polypeptide of SEQ ID NO:1 (with or without one of the first two Met, with or without periplasmic tag, and with or without an additional poly-His C-terminal tag as described herein). In some embodiments, the composition comprises one or more polypeptide with improved activity in the catalysis of the dehydration of 3-buten-2-ol to 1,3-butadiene. In some embodiments, the composition comprises one or more polypeptide with improved increased specific activity in the catalysis of the dehydration of 3-buten-2-ol to 1,3-butadiene. In other embodiments, the composition comprises one or more polypeptides with improved activity and one or more polypeptides with increased specific activity in the catalysis of the dehydration of 3-buten-2-ol to 1,3-butadiene.

In some embodiments the composition may be composed of one or more disclosed polypeptides, from (1) commercial suppliers; (2) cloned genes expressing said polypeptides; (3) complex broth (such as that resulting from growth of a microbial strain or any other host cell in media, wherein the strains/host cells secrete the disclosed polypeptides into the media; (4) cell lysates of strains/host cells grown as in (3); and/or (5) any other host cell material expressing the disclosed polypeptide. Different disclosed polypeptides in a composition may be obtained from different sources.

In some embodiments, the composition comprises 3-buten-2-ol and one or more polypeptides described herein. In other embodiments, the composition further comprises a wild-type polypeptide of SEQ ID NO:1 (with or without one of the first two Met, with or without periplasmic tag, and with or without an additional poly-His C-terminal tag as described herein).

In some embodiments, the composition comprises 1,3-butadiene and one or more polypeptides described herein. In other embodiments, the composition further comprises a wild type polypeptide of SEQ ID NO:1 (with or without one of the first two Met, with or without periplasmic tag, and with or without an additional poly-His C-terminal tag as described herein).

In some embodiments, the composition comprises a rubber product polymerized from 1,3-butadiene produced in the presence of a polypeptide as described herein.

In some embodiments, the composition comprises a copolymer polymerized from 1,3-butadiene produced in the presence of a polypeptide as described herein.

In some embodiments, the composition comprises a plastic product polymerized from 1,3-butadiene produced in the presence of a polypeptide as described herein.

Antibodies capable of binding to a polypeptide of the embodiments, or to relatives or fragments thereof that encompass at least one of the improved mutations/alterations described herein, are also encompassed. Methods for producing antibodies are well known in the art (see, for example, Harlow and Lane, (1988) Antibodies: A Laboratory Manual, Cold Spring Harbor Laboratory, Cold Spring Harbor, N.Y) and more recent art-recognized manuals of antibody production.

Methods of Use

The polypeptides, nucleic acids, and compositions described herein may be used in many different applications. Some of those applications are described in the SUMMARY and/or the claims.

One embodiment relates to a method of producing 1,3-butadiene comprising dehydrating 3-buten-2-ol to 1,3-butadiene in the presence of a polypeptide as described herein.

Another embodiment relates to the use of a polypeptide as described herein in the preparation of a product, wherein the product is polymerized from 1,3-butadiene produced in the presence of the polypeptide. In one embodiment, the product is a rubber product. In one embodiment, the product is a copolymer. In another embodiment, the product is a plastic.

Another embodiment relates to a method of constructing a disclosed polypeptide, which method comprises (a) making alterations in the amino acid sequence each of which is an insertion, a deletion or a substitution of an amino acid residue at one or more positions of SEQ ID NO:1 (or SEQ ID NO:1 without the periplasmic tag, or SEQ ID NO:4, or 5), (b) preparing the polypeptide resulting from those alterations, (c) testing the 1,3-butadiene producing activity of the polypeptide, (d) optionally repeating steps a)-c) recursively; and (e) selecting a polypeptide having an improved 1,3-butadiene producing activity as compared to that of the wild-type polypeptide of SEQ ID NO:1 (or SEQ ID NO:1 without the periplasmic tag, or SEQ ID NO:4, or 5).

All of the claims in the claim listing are herein incorporated by reference into the specification in their entireties as additional embodiments.

EXAMPLES

All of the compositions and methods disclosed and claimed herein can be made and executed without undue experimentation in light of the present disclosure and the knowledge of one of ordinary skill in the art. In some cases, the compositions and methods of this disclosure have been described in terms of embodiments; however these embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

1. Enzymes

Four enzymes were tested for product formation for step b) of the following reaction: step a) isomerization and dehydration of the natural substrate linalool and step b) the dehydration of 3-buten-2-ol to 1,3-butadiene.

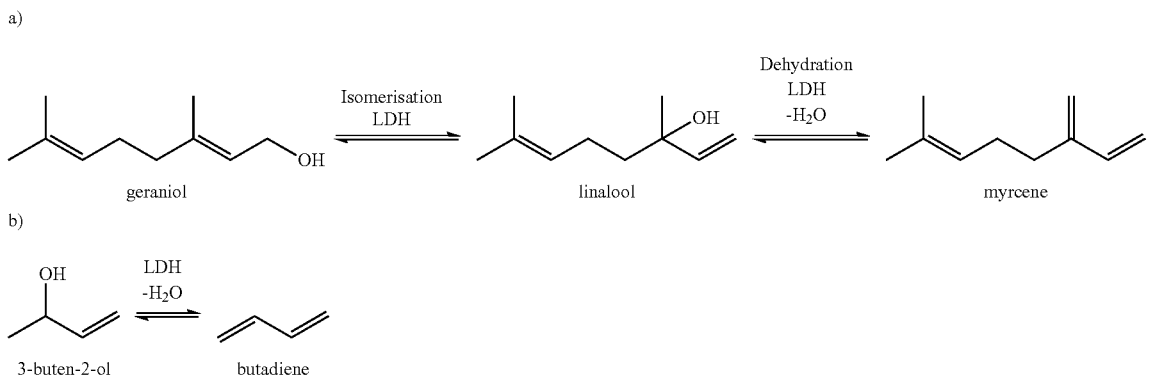

The four enzymes were: 1—Linalool dehydratase/isomerase from *Castellaniella defragrans*, EC 4.2.1.127 hereafter abbreviated cdLD, 2—Oleate hydratase from *Elizabethkingia meningoseptica* and *Streptococcus Pyogenes*, EC 4.2.1.53 hereafter abbreviated emOH and spOH, 3—Lycopene Hydratase from *Thiocapsa roseopersicina* and *Rubrivivax gelatinosus*, EC 4.2.1.131 hereafter abbreviated trLH and rgLH, and finally 4—Kievitone hydratase from *Fusarium Phaseoli*, EC 4.2.1.95 hereafter abbreviated fpKH). Only cdLD showed repeatable activity for step b).

The amino-acid sequence for *C. defragrans* linalool dehydratase (hereafter referred to as cdLD) is available in public databases (accession number gi302064203 in the protein NCBI databank) and was reported by Brodkorb et al., "Linalool dehydratase-isomerase, a bifunctional enzyme in the anaerobic degradation of monoterpenes", Journal of Biological Chemistry, Vol 285 (40), pp 30436-30442. The amino-acid sequence used herein is reproduced below. Note that, as described in Brodkorb et al., the sequence has the N-terminal signal MRFTLKTTAIVSAAALLAGFGPPPRAA (SEQ ID NO:3) which is a bacterial periplasmic routing signal. The protein used herein also has an extra Met residue relative to the cdLD described in the NCBI database as Genbank Accession E1XUJ2.1

```
>gi|302064203|emb|CBW30776.1| linalool
dehydratase-isomerase precursor
[Castellaniella defragrans] plus extra
N-terminal methionine.
MMRFTLKTTAIVSAAALLAGFGPPPRAAELPPGRLATTEDYFAQQAKQAV

TPDVMAQLAYMNYIDFISPFYSRGCSFEAWELKHTPQRVIKYSIAFYAYG

LASVALIDPKLRALAGHDLDIAVSKMKCKRVWGDWEEDGFGTDPIEKENI

MYKGHLNLMYGLYQLVTGSRRYEAEHAHLTRIIHDEIAANPFAGIVCEPD

NYFVQCNSVAYLSLWVYDRLHGTDYRAATRAWLDFIQKDLIDPERGAFYL

SYHPESGAVKPWISAYTTAWTLAMVHGMDPAFSERYYPRFKQTFVEVYDE

GRKARVRETAGTDDADGGVGLASAFTLLLAREMGDQQLFDQLLNHLEPPA

KPSIVSASLRYEHPGSLLFDELLFLAKVHAGFGALLRMPPPAAKLAGK
SEQ1: WT cdLD amino-acid sequence (SEQ ID NO: 1);
SEQ ID NO: 1 without the first of the two first
Methionines is SEQ ID NO: 7.
```

The DNA sequence below (SEQ2) codes for the amino-acid sequence of Linalool dehydratase-isomerase listed above as SEQ1. It was codon-optimized for *E. coli* and subsequently cloned into the pARZ4 vector (a modified version of the pET29 vector). A C-terminal 6-HIS tag (SEQ ID NO: 10) is added to the sequence in the pARZ4 vector, after a GS (Gly-Ser) linker and is included (in lower case) in the sequence SEQ2 below. The total His-Tag is GSLE-HHHHHH (SEQ ID NO:6).

```
>gi|302064203|emb|CBW30776.1| linalool
dehydratase-isomerase precursor
[Castellaniella defragrans]
atgATGCGTTTCACATTAAAGACCACCGCGATTGTTTCTGCCGCCGCGTT

ATTAGCGGGTTTTGGACCACCACCTCGTGCAGCAGAATTACCTCCCGGCC

GCCTTGCCACAACCGAAGATTATTTCGCACAACAAGCAAAACAAGCTGTA

ACCCCGGATGTTATGGCTCAACTCGCGTACATGAACTATATTGATTTCAT

TAGCCCCTTTTATTCACGTGGATGTTCATTCGAAGCATGGGAATTGAAAC

ACACTCCGCAGCGCGTGATTAAATACTCCATTGCATTCTATGCTTATGGC

TTGGCATCTGTAGCATTAATCGACCCTAAACTGCGCGCGCTCGCCGGCCA

CGACTTAGATATTGCAGTCTCAAAAATGAAATGTAAACGTGTATGGGGAG

ATTGGGAAGAAGATGGTTTTGGTACAGATCCGATTGAAAAAGAAAACATT

ATGTATAAAGGACATCTGAACCTTATGTATGGTCTCTATCAACTTGTTAC

TGGATCGCGCCGTTACGAAGCTGAACACGCTCACCTCACCCGTATTATCC

ACGACGAAATTGCCGCCAACCCATTCGCCGGAATCGTTTGTGAACCAGAC

AACTATTTTGTACAATGCAACTCTGTGGCCTATTTAAGCCTTTGGGTCTA

CGATCGTTTACATGGAACTGACTACCGTGCCGCAACTCGTGCCTGGCTGG

ATTTTATTCAAAAAGATCTGATTGACCCCGAACGTGGAGCTTTCTATTTG

TCCTATCATCCCGAATCTGGTGCCGTCAAACCTTGGATCAGCGCATATAC

AACCGCTTGGACGTTAGCTATGGTGCATGGAATGGATCCTGCCTTTTCAG

AACGTTATTATCCTCGTTTTAAACAAACGTTCGTCGAAGTCTATGATGAA

GGCCGTAAAGCCCGCGTACGCGAAACTGCCGGAACCGACGACGCCGATGG

TGGTGTGGGTTTAGCCTCTGCGTTCACACTTTTATTAGCCCGCGAAATGG

GAGATCAACAACTCTTTGACCAACTGCTGAATCATTTAGAACCCCCTGCC
```

```
-continued
AAACCAAGCATCGTTTCTGCTAGCCTCCGCTACGAACACCCAGGCAGCCT

CTTATTCGACGAACTGTTATTTCTTGCCAAAGTACATGCCGGATTTGGTG

CTCTGTTACGTATGCCCCCTCCTGCCGCCAAATTAGCGGGCAAAGGTTCC ctcgagcaccaccaccaccaccactga
SEQ2: optimized DNA sequence coding for SEQ1.
The sequence is optimized for E coli expression.
The start codon, GS linker and His6-tag
(SEQ ID NO: 10) are in lower case. (SEQ ID NO: 2)
```

2. Protein Expression and Purification a. Expression and Purification of Peri-cdLD in BL21 Cells in the Presence of pKJE7, pGro7 and pTf16 Chaperone Plasmids.

Plasmids expressing chaperones were purchased from TaKaRa. They were pG-KJE8 (expresses chaperons dnaK-dnaJ-grpE groES-groEL), pGro7 (groES-groEL), pKJE7 (dnaK-dnaJ-grpE), pG-Tf2 (groES-groEL-tig) and pTf16 (tig)

Periplasmic cdLD mutants were expressed in BL21 cells with pGro7 plasmid and purified by His-tag affinity resin. Chemically competent BL21 cells carrying a pGro7 plasmid were transformed with pARZ4 vector harboring the desired cdLD. On day 1 of expression, 10 ml overnight culture of LB/KAN (50 ug/ml) with chloramphenicol (20 ug/ml) at 37° C. were started in the evening. On day 2, 500 ml LB/KAN with chloramphenicol (20 ug/ml) were inoculated with 10 ml overnight culture. The culture was grown to an OD600 nm 0.6-0.8 at 37° C. The cells were induced overnight with 500 ul 1M IPTG at 25° C. The 500 ml culture was centrifuged at 9,000×g, 20° C. for 5 minutes. The cells were resuspended in 6 ml 50 mM Tris-HCl pH9/150 mM NaCl and stored at −20° C.

6 ml cdLD pellet were lysed with spatula tips of lysozyme, DNase I, and 600 ul 10× Bugbuster Protein Extraction Reagent for 25 minutes at room temperature. The lysed cells were centrifuged at 12,000×g for 25 minutes at 5° C. The supernatant was filtered with a 0.8 um/0.2 um membrane. The supernatant was loaded 3× on Ni-NTA column (bed volume 1.25 ml). The column was washed with 50 ml 50 mM Tris-HCl pH9/150 mM NaCl and 50 ml 50 mM Tris-HCl pH9/150 mM NaCl/20 mM Imidazole. The cdLD was eluted with 10 ml 50 mM Tris-HCl pH9/150 mM NaCl/250 mM Imidazole. 10 ml of cdLD elution were degassed with argon for 30 minutes and 200 ul 100 mM DTT were added to the elution. 10 ml of elution were concentrated to ~2 mL in a Sartorius Vivaspin 15R Centrifugal Concentrator. 1.5 ml of concentrated cdLD were desalted with 2 ml degassed 80 mM Tris-HCl pH9 in Hi-Trap Desalting column. The 2 ml sample was overlayed with argon and stored at 4° C. cdLD was observed on a SDS gel with a molecular weight of ~40 kDa. The concentration of 2 ml desalted cdLD was ~1 mg/ml resulting in ~2 mg per 500 ml expression culture.

b. Expression and Purification of Cyto-cdLD in Origami 2 (DE3) Strain

Cytoplasmic cdLD was expressed in the Origami 2 (DE3) strain with the following genotype: Δ(ara-leu)7697 ΔlacX74 ΔphoA PvuII phoR araD139 ahpC galE galK rpsL F′[lac+ lacI$^q$ pro](DE3) gor522::Tn10 trxB pLysS (Cam$^R$, Str$^R$, Tet$^R$).

Chemically competent Origami 2 (DE3) cells carrying a pGro7 plasmid were transformed with pARZ4 (a proprietary pET24 derivative) harboring the desired cdLD. On day 1 of expression, 10 ml overnight cultures of LB/KAN (50 ug/ml) at 37° C. were started in the evening. On day 2, 500 ml LB/KAN were inoculated with 10 ml overnight culture. The culture was grown to an OD600 nm 0.6-0.8 at 37° C. The cells were induced overnight with 500 ul 1M IPTG at 25° C. The 500 ml culture was centrifuged at 9,000×g, 20° C. for 5 minutes. The cells were resuspended in 6 ml 50 mM Tris-HCl pH9/150 mM NaCl and stored at −20° C.

6 ml of cdLD pellet were lysed with spatula tips of lysozyme, DNase I, and 600 ul 10× Bugbuster Protein Extraction Reagent for 25 minutes at room temperature. The lysed cells were entrifuge at 12,000×g for 25 minutes at 5° C. The supernatant was filtered with a 0.8 um/0.2 um membrane. The supernatant was loaded 3× on Ni-NTA column (bed volume 1.25 ml). The column was washed with 50 ml 50 mM Tris-HCl pH9/150 mM NaCl and 50 ml 50 mM Tris-HCl pH9/150 mM NaCl/20 mM Imidazole. The cdLD was eluted with 10 ml 50 mM Tris-HCl pH9/150 mM NaCl/250 mM Imidazole. 10 ml of cdLD elution were degassed with argon for 30 minutes and 200 ul 100 mM DTT were added to the elution. 10 ml of elution were concentrated to ~2 mL in a Sartorius Vivaspin 15R Centrifugal Concentrator. 1.5 ml of concentrated cdLD were desalted with 2 ml degassed 80 mM Tris-HCl pH9 in Hi-Trap Desalting column. The 2 ml sample was overlayed with argon and stored at 4° C. cdLD was observed on a SDS gel with a molecular weight of ~40 kDa. The concentration of 2 ml desalted cdLD was ~1 mg/ml resulting in ~2 mg per 500 ml expression culture.

3. The 1 ml Butadiene Assay for Linalool Dehydration Reaction

Bacterial cells transformed with the appropriate constructs were picked from LB plates into 400 ul of LB media containing 25 μg/mL kanamycin in deep-well 96-well plates and incubated overnight at 37° C. with vigorous shaking. Next morning, 20 ul of this night culture was inoculated into 1 ml of LB media containing 25 μg/mL kanamycin of deep-well 96-well plates, shaken at 37° C. for several hours. When cell density reached appropriate level (OD of 0.6 at 600 nm), 0.5 ul of 1M IPTG were added to each well (final concentration 500 uM). Plates were incubated 24 h at 25° C. with vigorous shaking. Then, 900 ul of cell culture was transferred to a crimp vial along with 9 ul of 1.1M 3-buten-2-ol (final concentration of 11 mM), sealed and incubated at room temperature for 72 h. Following incubation samples were analyzed by Shimadzu GCMS-QP2010 Ultra with Agilent column HP PLOT/Q (0.32 mm, 15 m length, 20 um diameter). The program was as follows: column was heated at 90° C. for 1 min, followed by a temperature increase at 40° C. per minute until it reached 200° C. Ion source was heated at 230° C., interface at 180° C., inlet at 250° C. 8 ul of the crimp vial headspace was injected in a split mode with split ration 2:1. Total He flow was at 9 ml/min, septum purge flow at 3 ml/min and column flow at 2 ml/min. Butadiene was detected at 2.26 min by monitoring ions with m/z 39, 50 and 54 in SIM mode. Butadiene from each sample was compared to the wild-type cdLD enzyme present on each plate. Relative activity was calculated as a ratio between the amounts of butadiene produced by a particular variant and the wild-type enzyme.

This is the assay for BL21 (DE3), which is the cell line for peri-cdLD, and for cyto-cdLD.

4. Assay for WT Linalool Dehydration Reaction (Conversion of Linalool to Myrcene)

Purified proteins were tested for their wild type linalool dehydratase activity. 100 μl of purified protein were transferred into an eppendorf tube along with 80 μl of degassed 80 mM Tris-HCl buffer (pH 9) as well as 20 μl of 100 mM linalool solution in DMSO. Negative control reactions were tubes without protein or without linalool (substrate). Tubes were shaken at room temperature for 1 h, followed by adding of 200 μl of ethylacetate. This mixture was vortexed and spinned down for 1 min in the tabletop centrifuge. The organic phase was transferred to GC vial and analysed by Shimadzu GCMS-QP2010 Ultra with Restek column Rxi-624Sil (0.32 mm, 60 m length, 1.8 um diameter). The program was as follows: column was heated at 100 C for 1 min, followed by a temperature increase at 50 C per minute until it reached 280 C. Injection temperature was 250 C. 8 ul of ethylacetate solution was injected in a splitless mode. Total He flow was at 58 ml/min and column flow at 1.86 ml/min. Myrcene was detected at 5.50 min, linalool at 6.17 and geraniol at 6.96 by monitoring ions with m/z 69, 71 and 93 in SIM mode.

5. Crystal Structure Determination

A delta-BLAST search on the database of protein sequences from the Protein Data Bank (PDB) revealed that cdLD did not have any detectable homology to any sequence for which a structural model was available. The crystal structure of cdLD was then obtained through two private contractors: Novalix, Illkirch-France and Emerald Bio, Bainbridge-WA. Both companies followed the same general approach.

The protein expressed from a construct having WT cdLD sequence (SEQ1) plus HIS-tag was crystallized. In the actual crystal structure obtained however, the periplasmic signal/tag is cleaved, the first fully resolved residue is L29 (peri-cdLD WT numbering) and the last resolved residue is P390 (i.e. the HIS-tag has no visible density. This is the sequence below (SEQ ID NO: 11):

```
LPPGRLATTEDYFAQQAKQAVTPDVMAQLAYMNYIDFISPFYSRGCSFEA

WELKHTPQRVIKYSIAFYAYGLASVALIDPKLRALAGHDLDIAVSKMKCK

RVWGDWEEDGFGTDPIEKENIMYKGHLNLMYGLYQLVTGSRRYEAEHAH

LTRIIHDEIAANPFAGIVCEPDNYFVQCNSVAYLSLWVYDRLHGTDYRAA

TRAWLDFIQKDLIDPERGAFYLSYHPESGAVKPWISAYTTAWTLAMVHGM

DPAFSERYYPRFKQTFVEVYDEGRKARVRETAGTDDADGGVGLASAFTL

LLAREMGDQQLFDQLLNHLEPPAKPSIVSASLRYEHPGSLLFDELLFLAK

VHAGFGALLRMPP
```

An additional three constructs with N-terminal and C-terminal deletions were also considered, but none yielded soluble protein in appreciable quantities: construct 1—deletion of residues Glu28-Thr36 and C-terminal cut at Arg387; construct 2—deletion of residues Glu28-Ile67; and construct 3—deletion of residues Glu28-Ile67 and C-terminal cut at Arg387 (all are with respect to the numbering of WT cdLD of SEQ1). Their sequences are as follows:

```
Del Glu28-Thr36 + C-ter cut at Arg387
(SEQ ID NO: 12)
>gi|302064203|emb|CBW30776.1| linalool
dehydratase-isomerase precursor
[Castellaniella defragrans] SIGNAL SEQ
MMRFTLKTTAIVSAAALLAGFGPPPRAATEDYFAQQAKQAVTPDVMAQL

AYMNYIDFISPFYSRGCSFEAWELKHTPQRVIKYSIAFYAYGLASVALID

PKLRALAGHDLDIAVSKMKCKRVWGDWEEDGFGTDPIEKENIMYKGHLNL

MYGLYQLVTGSRRYEAEHAHLTRIIHDEIAANPFAGIVCEPDNYFVQCNS
```

-continued
VAYLSLWVYDRLHGTDYRAATRAWLDFIQKDLIDPERGAFYLSYHPESGA

VKPWISAYTTAWTLAMVHGMDPAFSERYYPRFKQTFVEVYDEGRKARVRE

TAGTDDADGGVGLASAFTLLLAREMGDQQLFDQLLNHLEPPAKPSIVSAS

LRYEHPGSLLFDELLFLAKVHAGFGALLRGSLEHHHHHH

Del Glu28-Ileu67 (SEQ ID NO: 13)
>gi|302064203|emb|CBW30776.1| linalool
dehydratase-isomerase precursor
[Castellaniella defragrans] SIGNAL SEQ
MMRFTLKTTAIVSAAALLAGFGPPPRAASPFYSRGCSFEAWELKHTPQR

VIKYSIAFYAYGLASVALIDPKLRALAGHDLDIAVSKMKCKRVWGDWEED

GFGTDPIEKENIMYKGHLNLMYGLYQLVTGSRRYEAEHAHLTRIIHDEIA

ANPFAGIVCEPDNYFVQCNSVAYLSLWVYDRLHGTDYRAATRAWLDFIQK

DLIDPERGAFYLSYHPESGAVKPWISAYTTAWTLAMVHGMDPAFSERYY

PRFKQTFVEVYDEGRKARVRETAGTDDADGGVGLASAFTLLLAREMGD

QQLFDQLLNHLEPPAKPSIVSASLRYEHPGSLLFDELLFLAKVHAGFGAL

LRMPPPAAKLAGKGSLEHHHHHH

Del Glu28-Ileu67 + C-ter cut at Arg387
(SEQ ID NO: 14)
>gi|302064203|emb|CBW30776.1| linalool
dehydratase-isomerase precursor
[Castellaniella defragrans] SIGNAL SEQ
MMRFTLKTTAIVSAAALLAGFGPPPRAASPFYSRGCSFEAWELKHTPQR

VIKYSIAFYAYGLASVALIDPKLRALAGHDLDIAVSKMKCKRVWGDWEED

GFGTDPIEKENIMYKGHLNLMYGLYQLVTGSRRYEAEHAHLTRIIHDEIA

ANPFAGIVCEPDNYFVQCNSVAYLSLWVYDRLHGTDYRAATRAWLDFIQK

DLIDPERGAFYLSYHPESGAVKPWISAYTTAWTLAMVHGMDPAFSERYY

PRFKQTFVEVYDEGRKARVRETAGTDDADGGVGLASAFTLLLAREMGD

QQLFDQLLNHLEPPAKPSIVSASLRYEHPGSLLFDELLFLAKVHAGFGAL

LRGSLEHHHHHH

All the constructs contain the N-terminal periplasmic tag. Expression and Ni-NTA purification for the Novalix crystals were according to the following. Cultures of cdLD were done in bacteria BL21(DE3) in 1 L of Power Broth medium. Induction with IPTG was done at 18° C. overnight. After centrifugation, pellets were resuspended in 200 ml of lysis buffer (Tris pH8 20 mM, NaCl 500 mM, Glycerol 10%, Imidazole pH8 10 mM, Chaps 1%, TCEP 1 mM) for 6 L culture and treated with ultrasound. After centrifugation at 53000 g, soluble extract was incubated with around 2 ml of Talon beads overnight. Column was washed with 5-column volume of lysis buffer and elution was performed in one step with elution buffer (Tris pH8 20 mM, NaCl 500 mM, Glycerol 10%, Imidazole pH8 250 mM Chaps 1 mM TCEP 1 mM). Then, sample was applied on SEC column (Hiload 16/60 S75) pre-equilibrated with SEC buffer (Tris pH8 20 mM, NaCl 150 mM, Glycerol 5%). Average purification yield 2 mg of cdLD pure protein for 6 L culture. Protein was then concentrated up to 6 mg/ml in SEC buffer before crystallization assays. A total of 960 crystallization conditions were tested. Crystals of cdLD used for structure determination were obtained in Morpheus screen H2 condition (P8000 10%, Ethylene Glycol 20%, Na-I-glutamate 0.02M, dl-alanine 0.02M, glycine 0.02M, dl-lysine HCl 0.02M, dl-serine 0.02M) at 295° K. Crystals appears within few days and are very thin and delicate to handle. Thanks to ethylene glycol in the mother liquor, crystals can be fished and directly frozen in liquid nitrogen.

Conditions of expression and purification for the Emerald crystals were as follows. cdLD from the Arzeda-supplied plasmid was expressed as secreted protein in the periplasmic space. Fermentation conditions were: growth of *E. coli* cells harboring the pARZ_cdLD plasmid (expressing cdLD with the sequence in the table below, SEQ ID NO:9) at the 8 L scale in 1 L shake flasks of LB media, induced at OD ~0.600 with 1 mM IPTG and grown overnight at 25° C.

| Target protein | cdLD |
|---|---|
| AA sequence | MMRFTLKTTAIVSAAALLAGFGPPPRAAELPPGRLATTEDY FAQQAKQAVTPDVMAQLAYMNYIDFISPFYSRGCSFEAWEL KHTPQRVIKYSIAFYAYGLASVALIDPKLRALAGHDLDIAV SKMKCKRVWGDWEEDGFGTDPIEKENIMYKGHLNLMYGLYQ LVTGSRRYEAEHAHLTRIIHDEIAANPFAGIVCEPDNYFVQ CNSVAYLSLWVYDRLHGTDYRAATRAWLDFIQKDLIDPERG AFYLSYHPESGAVKPWISAYTTAWTLAMVHGMDPAFSERYY PRFKQTFVEVYDEGRKARVRETAGTDDADGGVGLASAFTLL LAREMGDQQLFDQLLNHLEPPAKPSIVSASLRYEHPGSLLF DELLFLAKVHAGFGALLRMPPPAAKLAGK<u>HHHHHH</u> |
| Color key | His tag in bold/<u>underline</u>, secretion signal in Bold |

*E. coli* paste was delivered on wet ice and cells were disrupted by mild osmotic shock to release periplasmic proteins. A detailed protocol for protein purification is provided below. Briefly, the protein was purified by Ni-IMAC chromatography using the C-terminal polyhistidine tag, followed by size exclusion chromatography. Purification yields were approximately 1 mg per liter of *E. coli* culture.

Starting with 8 L of *E. Coli* Paste:

| Periplasmic Release | Mild Osmotic Shock Buffer (MOSB): 200 mM Tris/HCl, pH 7.5, 2.0% (w/v), sucrose, one complete EDTA free protease inhibitor tablet (ice cold). |
|---|---|
| | 1. The sample pellets were resuspended in 800 mls (10% of the culture volume) of ice cold MOSB with 400 mgs of lysozyme added to the buffer just before use. The sample was gently shaken on ice for 20 minutes. |
| | 2. After 20 minutes, 800 mls of ice cold diH₂O was added to the sample and gently shaken for another 20 minutes. |
| | 3. Samples were pelleted via centrifugation at 5,000 rpm for 30 minutes at 4° C. |
| | 4. Supernatant was removed, filtered through an 0.2 µm bottle top filter and purified via Ni—NTA affinity chromatography. |

Protein Purification: Purification Step 1

All purification steps are carried out at 4° C. AKTA systems were flushed thoroughly with water then buffers before purification initiated.

| Chromatography Type | Ni I |
|---|---|
| Type of Column Used | HiTrap Ni Chelating |
| Quantity of Columns Used | 1 × 5 ml |
| New or Regenerated | New |
| Buffer A | 50 mM Tris pH 9, 0.15 M NaCl, 20 mM imidazole. Prepared Feb. 19, 2013. |
| Buffer B | 50 mM Tris pH 9, 0.15 M NaCl, 250 mM imidazole. Prepared Feb. 19, 2013. |

| | |
|---|---|
| Wash Buffer | 50 mM Tris pH 9, 0.15 M NaCl. Prepared Feb. 19, 2013. |
| Column Equilibration | 4 CVs A, 4 CVs B, 4 CVs A |
| AKTA System Used | BB-AKTA 2 |
| Load Volume and Flow Rate | 1.6 L, 1.5 ml/min |
| Wash Volume and Flow Rate | 50 ml, 2 ml/min |
| Elution Gradient, Flow Rate and Fraction Size | 0-60% B over 120 minutes, 1 ml/min, 5 ml fractions. |
| Comments | N/A |
| SDS-PAGE Analysis | 4-12% MOPS SDS-PAGE denatured at 95° C. for 5 minutes with 4X SDS loading dye containing 2-mercaptoetahanol. |

Protein Purification: Concentration Step 1 (Concentration Target: 15 mg/ml)

| | |
|---|---|
| Concentrator Type, MWCO, Spin Speed and Duration | Vivaspin 20 PES, 10 kDa MWCO, 5000-6500 RCF, 10-20 minutes intervals. |
| Initial Concentration (Nanodrop-1000) and Volume | 0.3 mg/ml, 45 ml |
| Final Concentration (Nanodrop-1000) and Volume | 5.05 mg/ml, 2.2 ml |

Protein Purification: Purification Step 2

| | |
|---|---|
| Chromatography Type | SEC |
| Type of Column Used | Sephacryl S-100 16/60 |
| Quantity of Columns Used | 1 × 120 ml |
| SEC Buffer | 10 mM Tris pH 9.0, 350 mM NaCl, 2 mM DTT. Prepared Feb 20, 2013. |
| Column Equilibration | 100% SEC Buffer, 240 Minutes at 0.5 mL/min |
| AKTA System Used | BB-AKTA 2 |
| Injection Volume and Flow Rate | 2.2 ml, 0.5 ml/min |
| Number of Iniections | 1 × 2.2 ml |
| Fraction Size | 3 ml |
| Comments | N/A |
| SDS-PAGE Anaiysis | 4-12% MOPS SDS-PAGE denatured at 95° C. for 5 minutes with 4X SDS loading dye containing 2-mercaptoethanol. |
| SDS-PAGE Analysis Conditions | Reduced |
| Aliquot Number, Volume, Concentration | 8 × 100 µl, 1 × 50 µl, at 10.28 mg/ml |
| Final Yield of Protein | 8.74 mgs |
| Final Buffer | 10 mM Tris pH 9.0, 350 mM NaCl, 2 mM DTT. |

3) Crystal Growth and Handling:

Crystals for structure determination of cdLD were obtained by using the sitting drop vapor diffusion method with 400 nL of protein solution (cdLD at 9.06 mg/mL in 10 mM Tris pH 9.0, 350 mM NaCl, 2 mM DTT) mixed with 400 nL of crystallization solution above a reservoir of ~40 µL of crystallization solution. Suitable crystallization conditions for growth of crystals were found by testing 576 random sparse matrix conditions from a variety of commercially available crystallization screens. Small crystals were obtained from the commercial screen Morpheus (Molecular Dimensions, Newmarket UK). The Morpheus screen utilizes complex mixtures of precipitants, buffers and additives. A description of the screen can be found at: www.moleculardimensions.com/applications/upload/MD1-47%20Morpheus%C2%AE.pdf. Based on these initial crystallization hits, an optimization screen was created that utilized varying concentrations of the Morpheus buffers. The crystal from which data were obtained was grown from the following components:

39.55% (v/v) Morpheus "EDO_P8K", a mixture of ethylene glycol and PEG 8000

10% (v/v) Morpheus Amino Acids, a mixture of L-Na-Glutamate; Alanine (racemic); Glycine; Lysine HCl (racemic); Serine (racemic)

6.12% (v/v) 1.0 M MES and 3.88% (v/v) 1.0 M imidazole; pH 6.5

In addition, the crystallization drop that yielded the crystal used for data collection also contained 0.05% (v/v) of 3-buten-2-ol.

The crystallization solution was a "direct cryo", i.e., a solution that would undergo a glass-like transition to solid when rapidly cooled in liquid nitrogen, and thus no additional cryoprotectant was required in order to freeze the crystal for data collection. The crystal was transferred to a crystal mounting loop and flash-cooled by being plunged into liquid nitrogen. All crystal growth took place in a temperature-controlled room at 16° C.

X-ray diffraction data collection: Data were collected via remote access at the Advanced Photon Source in Argonne, Ill. on beamline 21-ID-D on Apr. 18, 2013 using a MarMosaic 300 CCD detector. Data were processed and scaled using XDS/XSCALE. Data collection, scaling and refinement statistics are summarized in the following table:

| Parameter | Overall (Highest shell) |
|---|---|
| Radiation source | APS 21-ID-D |
| Collection date | 18 Apr. 2013 |
| $\Delta\phi$ | 1.0° |
| Frames | 250 |
| Distance | 300 mm |
| wavelength | 0.9300.5 Å |
| Crystal ID | 244270a7, puck ID lab8-4 |
| Space Group | $P2_1$ |
| Unit Cell | a = 88.70, b, = 111.22, c =120.42; $\alpha$ = 90.0, $\beta$ = 102.72, $\gamma$ = 90.0 |
| Resoluton | 2.60 Å (2.67 Å-2.60 Å) |
| I/$\sigma$ | 16.17 (2.71) |
| Completeness | 99.8% (99.9%) |
| $R_{merge}$ | 7.4% (51.4%) |
| Reflections (unique) | 284619 (70173) |
| Multiplicity | 4.06 |
| Refinement statistics | |
| $R_{cryst}$ | 17.20% |
| $R_{free}$ | 22.20% |
| rmsd bonds | 0.011 |
| rmsd angles | 1.430 |
| Mean B-Factor | 28.64 |

Structure Determination of the Emerald crystals: The structure cdLD was solved by molecular replacement using the program Phaser as implemented in the CCP4 suite of programs with a protein model representing a preliminary structure of the same target created by Novalix as a search model. The initial MR solution was refined using Refmac5. The model of cdLD was then refined using alternating rounds of manual re-building in Coot with restrained refinement with Refmac5. The final R/Rfree for the model was 17.20%/22.20%.

Because no structural homolog is known for cdLD, phasing cannot be solved using molecular replacement; instead, either isomorphous replacement or MAD/SAD need to be used. For the Novalix crystals, isomorphous replacement was not successful, therefore Sel-met MAD was chosen for the Novalix crystals. In order to obtain Se-met labeled cdLD, cultures were performed in M9 medium supplemented with Se-met 80 mg/ml in B834 bacteria strain. A starter culture was done in LB medium and was used to inoculate M9 culture. Then induction with IPTG was done at 18° C. overnight. A protocol of purification similar to native cdLD was performed for Se-met labeled protein. Average purification yield around 2 mg of labeled cdLD for 12 L of M9 culture. Crystals used for MAD diffraction were obtained in the same condition of the native protein. Crystals of native and Se-met labeled protein belong to the same $P2_1$ space group but with 2 different cells. Se-met cdLD crystals diffract only to 3.7 Å resolution compared to 2.5 Å resolution for a crystal of native cdLD. After identification and refinement of Se atom positions, a first model of cdLD was built at 3.7 Å resolution with CCP4 suite software and ShelX. Phases were then expanded at 2.5 Å resolution by molecular replacement in a native dataset.

TABLE 1

| Synchrotron data CV32 Native protein | |
| --- | --- |
| Protein | cdLD native |
| Dataset | CV32 |
| X-ray source | Proxima 1 (SOLEIL) |
| Wavelength (Å) | 0.98011 |
| Detector distance | 439.7 mm |
| Oscillation | 0.2° |
| Exposure time | 0.2 second |

TABLE 2

| Crystallographic data | |
| --- | --- |
| Dataset | CV32 |
| Resolution | 48.16-2.54 |
| (last shell) (Å) | (2.69-2.54) |
| Space group | P2(1) |
| Unit cell | a = 133.18 Å |
|  | b = 110.83 Å |
|  | c = 162.20 Å |
|  | α = 90.00° |
|  | β = 107.157° |
|  | γ = 90.00° |
| Unique reflections | 154892 |
| Completeness (last shell) (%) | 99.0% (96.10%) |
| Redundancy | 3.4 |
| I/□ (I) (last shell) | 13.84 (2.08) |
| $R_{sym}$ (I) (last shell) (%) | 7.71% (58.60%) |
| B from << Wilson plot >> | 48.08 Å$^2$ |

The crystal coordinates are provided in Appendix 1 for Novalix's crystal and Appendix 2 for Emerald's.

The statistics for the solved structure of the Novalix crystals are available in Tables 1 and 2.

6. General Features of the High-Resolution 3D Model of Apo-cdLD

Part I: Novalix: cdLD adopts a pentameric arrangement with 5-fold axial symmetry in the asymmetric unit (labeled chain A through E). Each monomer adopts □/□(6) barrel fold, a relatively unusual fold that can be seen in FIG. 1. In the crystal structure, one disulfide bond is formed between Cys74 and Cys127 of each subunit (crystal structure numbering). A structural homology search using the DALI program yielded a variety of structural homologs. Structural alignment between the cdLD monomer and some of the DALI hits revealed that the enzymes that are structurally homologous to cdLD all have their active sites in the "top" of the barrel with the catalytic residues supported by the innermost helixes that line up the inside of the barrel (helixes 4, 7, 9, 11, 13, 14) and the loops connecting these helixes to the outermost helixes from the barrel. Consistent with the other enzymes adopting a similar fold, cdLD presents a marked cleft in that same region whereas the rest of the subunit is tightly packed fully solvent exposed. Therefore, it is hypothesized that the likely position of cdLD active site responsible for the observed catalytic activity is located in that region. Contrary to most of cdLD structural homologs, this putative active site is formed at the interface between subunits, for example, A and B in FIG. 1. Loop 62-77 (crystal structure numbering) from subunit B protrudes and closes the pocket formed by the top of the barrel of subunit A, see FIG. 2.

Below is the mapping in amino-acid residues (in WT peri-cdLD numbering) for each secondary structure elements. Secondary structure assignment was made using the DSSP software (note that 'helixes' here include α, $3_{10}$ and π). Loop are not included because they are effectively all the remaining positions. See also FIG. 3.

TABLE 3

| Helix | Start-End Residues (peri-cdLD [SEQ1] numbering) |
| --- | --- |
| H1 | 37-41 |
| H2 | 43-46 |
| H3 | 51-61 |
| H4 | 77-82 |
| H5 | 86-106 |
| H6 | 108-125 |
| H7 | 128-131 |
| H8 | 133-136 |
| H9 | 149-165 |
| H10 | 172-188 |
| H11 | 203-220 |
| H12 | 228-236 |
| H13 | 264-274 |
| H14 | 279-293 |
| S1 | 294-296 |
| H15 | 298-300 |
| S2 | 303-305 |
| H16 | 321-331 |
| H17 | 335-345 |
| S3 | 351-353 |
| S4 | 358-360 |
| H18 | 368-377 |
| H19 | 381-385 |

Residue number for each of the secondary structure elements (helixes H and strand S) of cdLD, based on the high-resolution crystal structure. Secondary structure assignments have been obtained with DSSP 2.2.1. Helix annotations include □, 310 and □ helixes. Strands correspond to residue in the extended conformation, irrespective of whether they actually form □-stands.

Part II: Emerald Crystals

The asymmetric unit of the cdLD crystal is a pentamer with 5-fold axial symmetry.

Figure 16:
FIG. 16: Pentameric arrangement of cdLD protein monomers in the crystal asymmetric unit. Each polypeptide chain has a unique color.

Each individual subunit forms a head-to-tail interaction with a neighboring subunit where a loop around Tyr70 protrudes into a cavity at the center of the 6-alpha helix barrel of the cdLD monomer (top figure). At this interface is a narrow, >10 Å deep pocket that comprises the putative active site (FIG. 16).

During refinement of the Emerald crystal structure, a significant electron density feature was observed in all five subunits between residues Cys196 (wild-type cdLD; but Cys197 for wild-type cdLD with extra N-terminal amino acid) and Cys205 (wild-type cdLD; but Cys206 for wild-type cdLD with extra N-terminal amino acid). The shape of the electron density feature and the chemical coordination around the site were consistent with metal ion binding. The metal ion was presumed to be zinc, but the actual identity is unknown. No zinc or other divalent metals were present in the crystallization solution, however, a metal ion could have carried over during purification or been present as a trace contaminant from glassware. Additional weak electron density features (green mesh in FIG. 17) were observed but not modeled. The observed electron density features were not consistent with 3-buten-2-ol or individual water molecules. One explanation is that 3-buten-2-ol and/or other crystallization components could have been present at low occupancy and/or in multiple conformations in the putative active site cleft, preventing clear electron density from appearing.

7. cdLD Active Site Mutants Based on Novalix Crystal Data

Based on visual analysis of the putative active site, a list of polar groups lining the active site pocket were selected for further mutagenesis to assess their impact on catalytic activity for WT reaction natively catalyzed by cdLD. The list of candidate active site residues, and the proposed mutations that are predicted to affect catalytic activity, can be found in Table 4 below.

TABLE 4

Putative catalytic residues, catalytic activity proposed knock-out mutations, and impact on protein expression (peri-cdLD or cyto-cdLD) and catalytic activity for the dehydration of linalool to myrcene.

| Mutant | Priplasmic cdLD in BL21 with PGro7 | | Cytoplasmic cdLD in Origami2(DE3) | |
|---|---|---|---|---|
| | Protein on PAGE | Activity with linalool | Protein on PAGE | Activity with linalool |
| Y99F | | | faint | |
| Y99A | + | | faint | some |
| Y92F | + | | + | YES |
| Y92A | faint | | + | some |
| Y71F | + | | + | |
| Y71A | + | | | |
| Y266F | faint | | + | some |
| Y266A | | | | |
| Q205L | | | | |
| Q205A | faint | | + | some |
| M151L | faint | some | + | YES |
| M151K | + | | + | |
| M151A | + | | + | some |
| H115D | | | | |
| H115A | + | | faint | some |
| E198Q | + | | + | |
| E198A | faint | | + | |
| D65N | | | + | |
| D65A | + | | + | |
| C206S | + | | + | |
| C206A | | | ND | |
| C197S | + | | + | |
| C197A | + | | + | |
| WT peri | + | YES | + | YES |
| WT cyto | 5+ | YES | + | YES |

Each mutant was expressed and tested for its wild-type linalool dehydratase activity (Example 4). From these results, it was predicted that the following residues are candidates as catalytic residues: CYS197, CYS206, ASP65 and GLU198. They are the only residues for which cdLD was expressed and no catalytic activity towards the dehydration of linalool was observed.

8. cdLD Mutants with Improved Butadiene Production
   a. Activity in Cell Cultures (i.e., In Vivo Activity)

Approximately 400 cdLD mutants and sequence homologs were screened for activity with 3B2O as a substrate. See Appendix 3 for sequences. All constructs were constructed in pARZ-cdLD plasmid. This plasmid is derived from PET-29a vector, where cdLD gene was cloned between restriction sites NdeI and XhoI. The expression vector contains T7 promoter, lac operator and N-terminal His tag.

cdLD variants described herein were constructed at Gene9 Inc. (Cambridge, Mass.) with their proprietary methods. All genes were synthesized with the following overhangs: CTCTTCTTAACTTTAAGAAGGAGATATACAT (upstream) and CTCGAGCATCATCATCATCATCACTGAGATCCGGCTGCTAACAAAGCCCGGAAGA G (downstream) (SEQ ID NOS 15-16, respectively). Ten microliters of each cdLD variant was cut by Earl restriction enzyme (New England Biolabs) and purified by Qiagen QiaQuik PCR purification kit according to manufacturer's protocol. Next, all constructs were cloned in pARZ-4, which identical to pARZ-cdLD plasmid except that cdLD gene is replaced with a staffer fragment. pARZ-4 backbone was amplified with the following primers: GibsV4Rev (GTATATCTCCTTCTTAAAGTTA) and GibsV3for (TGAGATCCGGCTGCTAACAAAGC) (SEQ ID NOS 17-18, respectively). Each PCR amplification reaction contained 30 pmol of each primer and 100 ng of DNA template. Amplifications were carried out using Pfu Ultra II Hotstart DNA polymerase (Agilent, cat#600850-51). The PCR reaction (20 µL) was initially heated at 95° C. for 2.5 min followed by 30 cycles of denaturation at 94° C. for 15 sec., annealing at 55° C. for 15 sec. and extension at 72° C. for 5 min. Following amplification, PCR fragment was gel-purified by the QIAGEN® gel-band purification kit according to manufacturer's protocol. 1 ul of the amplified vector (approximately 0.05 pmoles) was mixed with 4 µl (appr. 0.3 pmoles) of cdLD variant and 5 µl of 2× Gibson Assembly mix (New England Biolabs, cat#M5510AA) and incubated 1 h at 50° C. Following incubation, each mix was diluted with sterile water (4-fold) and transformed in XL1Blue competent cells (Agilent) according to manufacturer's protocol. Transformed cells were plated on LB plates containing 25 µg/mL kanamycin and incubated overnight at 37° C. Next morning colonies were tested for the presence of the insert by colony PCR. Colonies were picked and resuspended in 20 ul of sterile 0.9% sodium chloride solution. One ul of this solution was transferred to the PCR tube and amplified with Taq polymerase (New England Biolabs, cat#M0482S) and 30 pmoles of primers P1 (ATAGGCGCCAGCAACCGCAC) and P2 (GCAGCAGCCAACTCAGCTTC) (SEQ ID NOS 19-20, respectively). Each PCR reaction (20 µL) was initially heated at 95° C. for 2.5 min followed by 30 cycles of denaturation at 94° C. for 15 sec., annealing at 55° C. for 15 sec. and extension at 72° C. for 1 min. Amplification products were visualized by agarose electrophoresis. Clones with the correct inserts were inoculated into the culture tubes containing 5 ml of LB and 25 µg/mL kanamycin and incubated overnight at 37° C. Next morning constructs were purified by Qiagen miniprep kit and transformed into BL21(DE3) competent cells (purchased from Invitrogen). These cells were plated on LB plates containing 25 µg/mL kanamycin and incubated overnight at 37° C.

Figure 4:
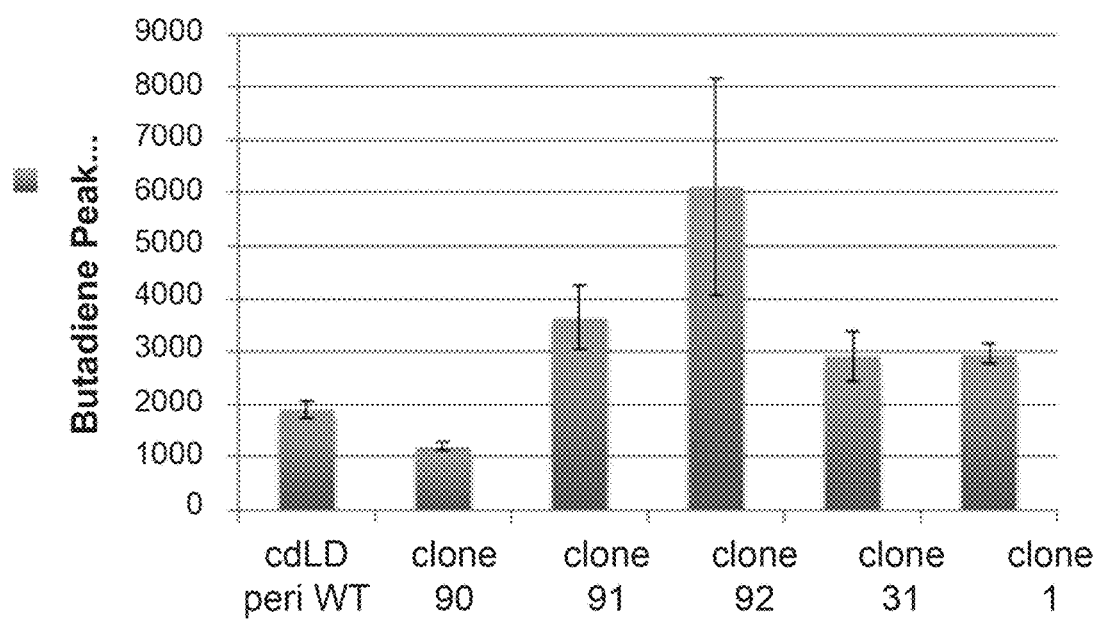
FIG. 4: Butadiene produced by selected periplasmic cdLD mutants obtained from stabilization design.

Each mutant was tested with the 1 ml butadiene assay (Example 3). Clones that produced butadiene at the levels comparable or higher than the wild type enzyme were regrown in several replicas and retested using the same 1 ml butadiene assay. The most interesting variants were retransformed into BL21(DE3) cell to avoid potential influence of host somatic mutations and also retested in 1 ml butadiene assay. Some of the results are shown in FIG. 4. First, four clones showed a marked improvement in in vivo butadiene production over the WT peri-cdLD enzyme. These were clones 91 (V123I, V204I, M274F, V275I), 92 (V123I, V204I, M274F, V275I, F382W), clone 1 (A324L) and clone 31 (R360Y). Clone 90 (V123I, V204I, V275I) differed from clone 91 by only one mutation (M274F), yet did not show butadiene production improvement.

Figure 5:
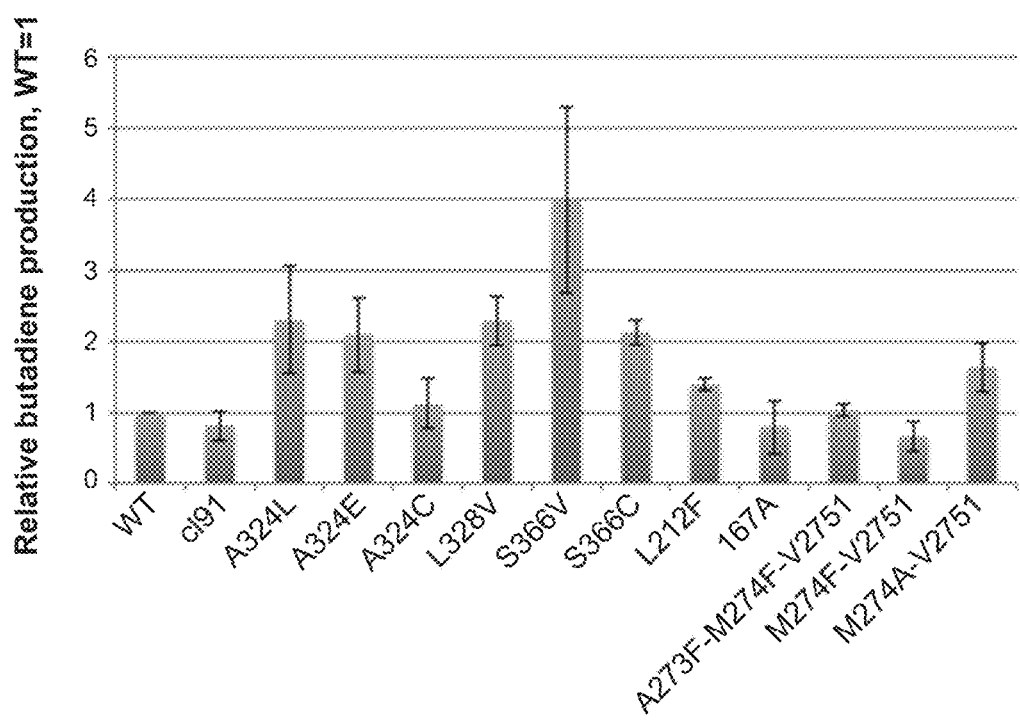
FIG. 5: Butadiene production by some mutants from the second set of site-saturation libraries.

An additional set of mutants was tested in the same assay. The results are show in FIG. 5. Mutant A324L, which was part of the above clone 1, is found again to have improved catalytic activity in this 1 mL butadiene assay. It was also found that the A324E mutation has similar activity. On the other hand, mutation A324C turned out to have no effect on butadiene production. Other mutants that had improved activity were: L328V, S366V, S366C and L212F. The highest improvement was achieved by mutant S366V.

Figure 6:
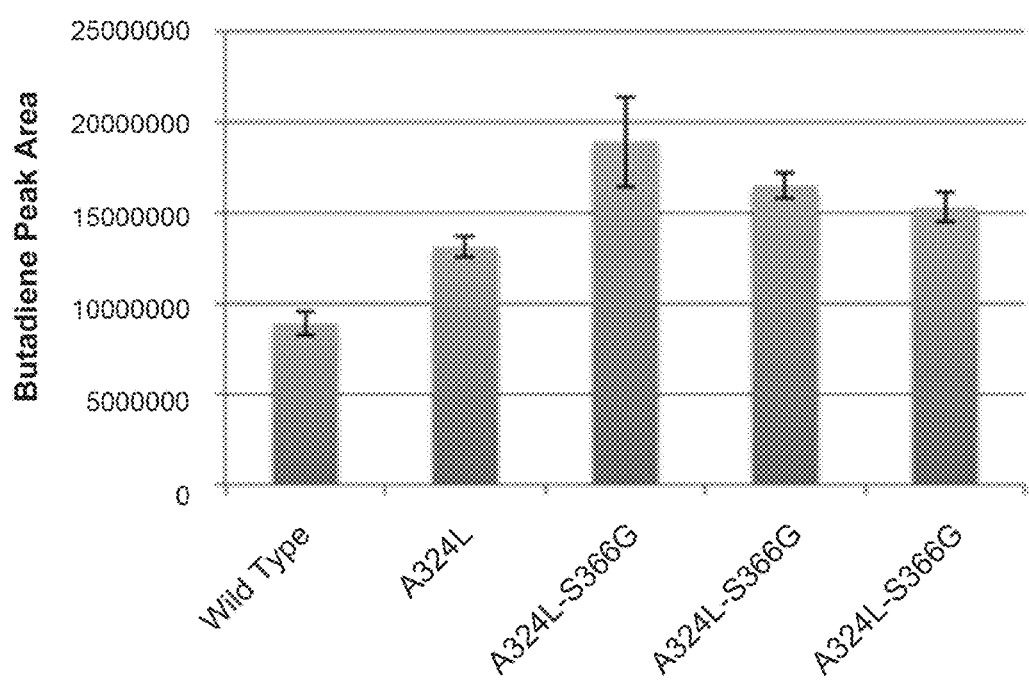
FIG. 6: Butadiene production by mutants built on top of A324L.
Figure 7:
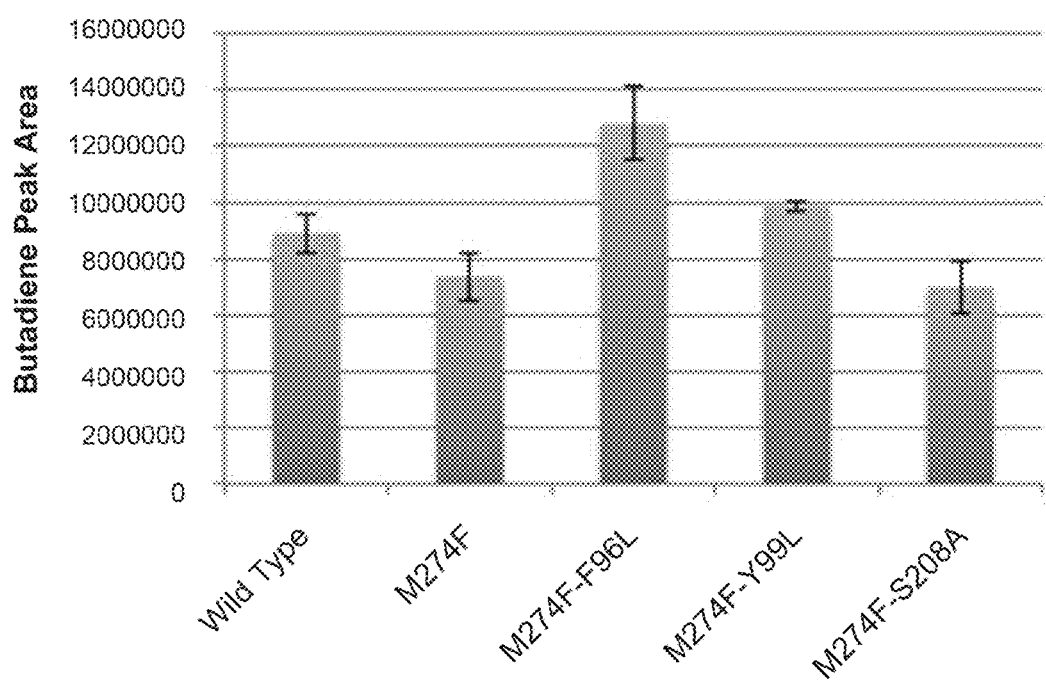
FIG. 7: Butadiene production by mutants built on top of M274F.
Figure 8:
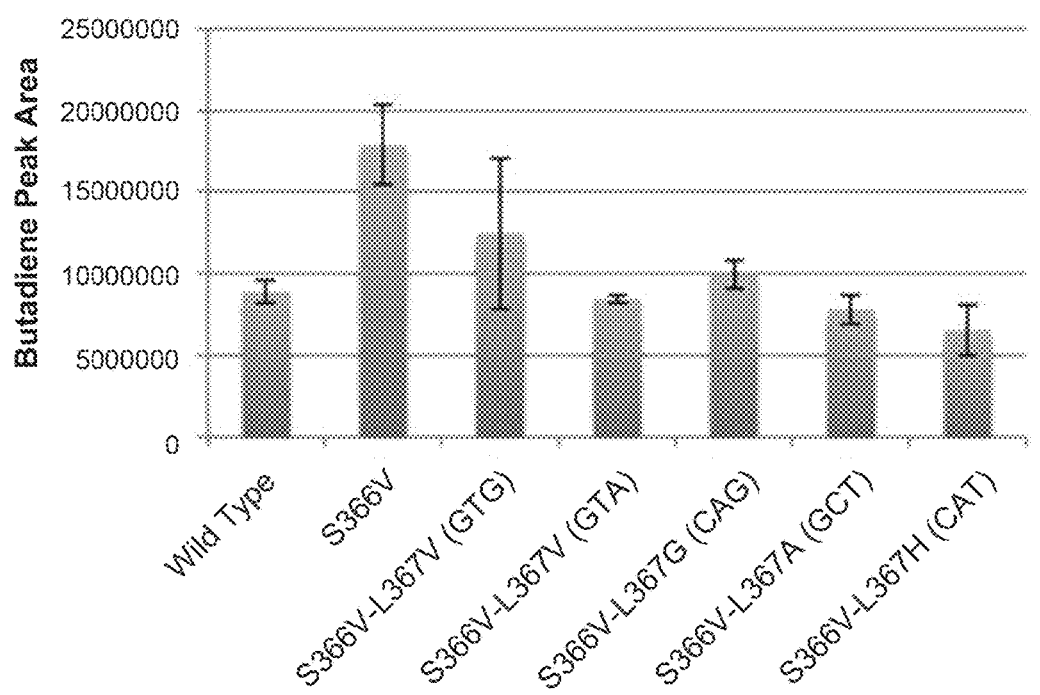
FIG. 8: Butadiene production by mutants built on top of S366V.
Figure 9:
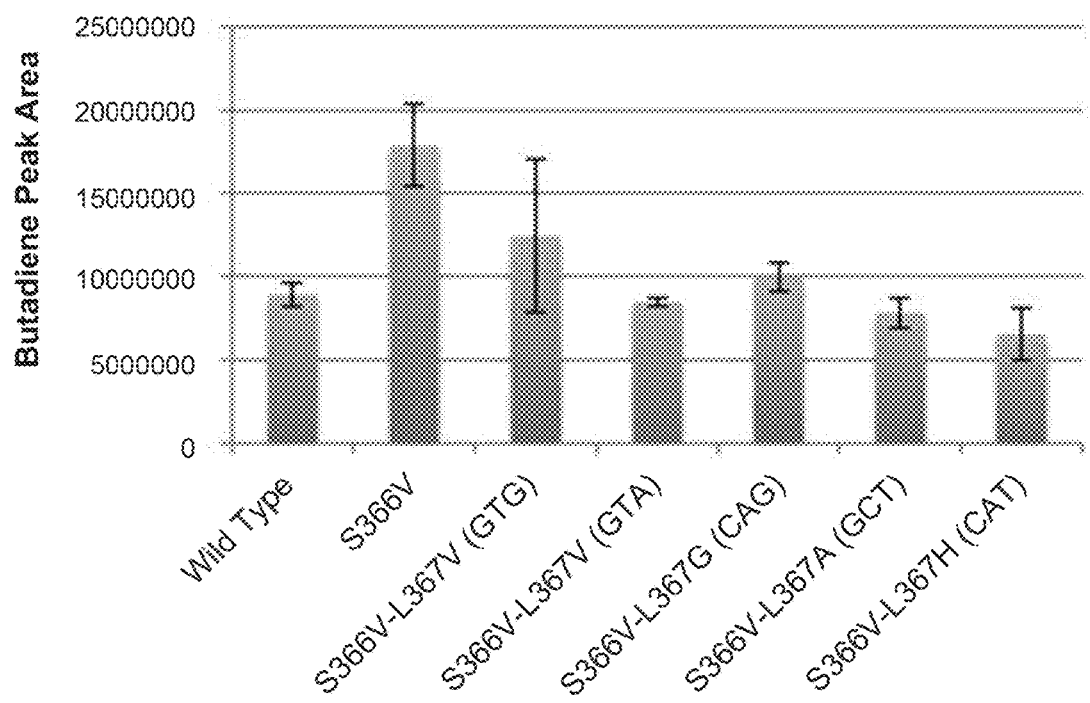
FIG. 9: Butadiene production by mutants built on top of V275I.
Figure 10:
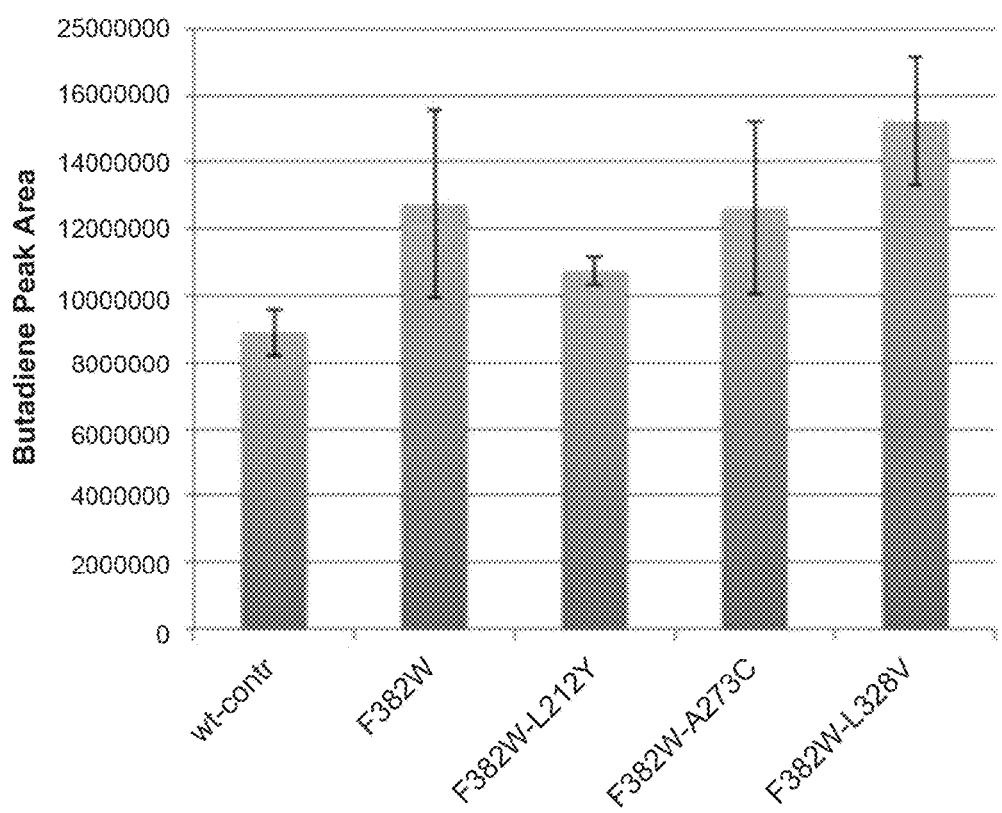
FIG. 10: Butadiene production by mutants built on top of F382W.

A number of additional mutations were introduced into each of these improved mutants to attempt to further augment their activity. The results are show in FIGS. 6-8. As can be seen in FIG. 6, three different clones with identical double mutations A324L and S366G showed improved butadiene production relative to their parent (A324L) and the wild type. The M274F mutant was a less efficient butadiene producer then the wild type. Addition of F96L (double mutant M274F and F96L) increased butadiene production (FIG. 7). Adding mutations to S366V (FIG. 8) and V275I (FIG. 9) did not improve butadiene production over the wild type level. Adding mutation L328V on top of F328W (double mutant F382W-L328V) seemed to improve butadiene production (FIG. 10).

b. Activity in Purified Samples

Figure 11:
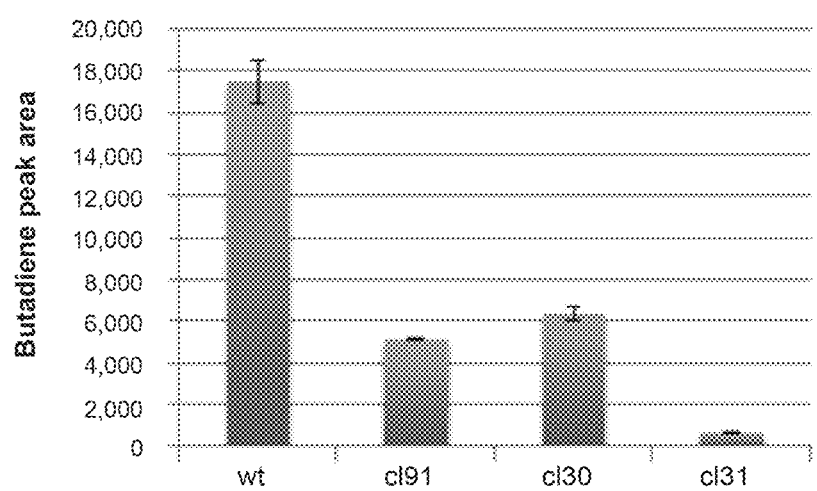
FIG. 11: Butadiene produced by certain purified periplasmic cdLD mutants.

Four variants of cdLD were purified with the standard His-tag purification procedure described in Example 2: WT, clone91, clone30 and clone31. Proteins were diluted to the same concentration. 250 μl of purified protein solution was transferred to a crimp vial along with 2.5 ul of 1.1M 3-buten-2-ol (final concentration of 11 mM), sealed and incubated at room temperature for 72 h. Following incubation samples were analyzed by Shimadzu GCMS-QP2010 Ultra with Agilent column HP PLOT/Q (0.32 mm, 15 m length, 20 um diameter) as described above for the 1 ml butadiene assay. Results are presented in FIG. 11. None of the variants showed an improvement in butadiene production when tested in this assay.

An alternative purification protocol was also used. From a fairly fresh LB plate containing the desired clone transformant, one colony (or small scratch) was picked to inoculate 10 to 50 mL of LB supplemented with the relevant antibiotic and the preculture was incubated overnight at 37° C., 230 rpm.

The following morning, prepare the TB auto-induce medium (Merck/Code product: 71491-5) by mixing 60 g TB/L supplemented with 10 mL Glycerol/L of TB and microwaved during 3+2 minutes at full power. Let the TB cool down under the hood before using it and splitting it in sterile flasks. Then, Spin down the preculture incubated overnight and discard the supernatant. Resuspend the preculture in 1 to 5 mL of freshly prepared TB medium and use it to inoculate 100 to 500 mL of TB dispensed in the sterile flasks, supplemented with the appropriate antibiotic. Incubate the flasks of inoculated flasks at 28-30° C. for at least 20 h, 230 rpm.

The main culture was centrifugated at least at 3000 g/20 min/4° C. and the pellets used immediately. The pellets were resuspended in 10 to 20 mL of Buffer A (=50 mM Tris+150 mM NaCl+40 mM Imidazole+5% Glycerol–pH 8.5).

The resuspended cells were then sonicated in ice for ≈5 min at 35-40% Amplitude with 5" ON and 15" OFF sonication pulse. The sonicated cells were centrifugated at least at 15500 g, 20 min at 4° C. The supernatant containing the soluble fraction of proteins was recovered and used for His-trap protein purification. The filtered soluble fraction of proteins obtained after extraction of proteins by sonication was used for His-tag protein purification. A 1 mL His-trap (GE Healthcare/Code product: 17-5319-01) column was equilibrated with 5-10 volumes column (VC) using Buffer A*. The soluble fraction of proteins was loaded onto the His-trap column manually using a syringe and 5-10 VC of Buffer A were used to wash the His-trap column. 5-10 VC of Buffer B were used to elute the His-tag protein directly to a 4 or 20 mL centrifugal filtration unit (VWR/Code product: 512-2850) with a relevant cut-off (5 kD). The centrifugal unit was spinned at 3500 g/5° C. to a volume lower than 400 uL concentrate. Around 3 mL of Buffer C* was added to the concentrate and the centrifugal unit was again spinned at 3500 g/5° C. to a volume lower than 400 uL. This step was made to remove most of the imidazole used in Buffer B to elute the His-tag.

The concentrate was recovered and according to the working concentration (≈2 mg/mL), Buffer C was used to top-up to the desired volume. The concentration was checked using a Nanodrop spectrophotometer.

*Buffer A=50 mM Tris+150 mM NaCl+40 mM Imidazole+5% (v/v) Glycerol–pH 8.5
**Buffer B=Buffer A+400 mM Imidazole–pH8.5
***Buffer C=Buffer A without Imidazole–pH8.5

The purified proteins were used for butadiene assay. A 1 mL reaction made of 2 mg/mL of each purified enzyme with 10 mM of 3-buten-2-ol or 3-methyl-3-buten-2-ol for the biosynthesis of 1,3-butadiene or isoprene respectively, was prepared in a 1.7 mL crimped glass vial. The vials were incubated at least 48 h at 30° C., 170 rpm. The butadiene and isoprene were analysed by head-space GC-MS using an authentic standard to set up a standard curve for quantification The results are shown in FIG. 12A. Mutants F382W/L328V; F382W/L328V/I187M; and A324L/S366G all showed improved activity in dehydration of 3-buten-2-ol to butadiene, relative to WT cdLD.

The same three mutants, purified the same way, were also tested for their ability to produce isoprene from 3-methyl-3-buten-2-ol.

A 1 mL reaction made of 2 mg/mL of each purified enzyme with 10 mM of 3-methyl-3-buten-2-ol for the biosynthesis of isoprene was prepared in a 1.7 mL crimped glass vial.

The vials were incubated at least 48 h at 30° C., 170 rpm. The isoprene was analyzed by head-space GC-MS using an authentic standard to set up a standard curve for quantification. The results are shown in FIG. 12B. Again, all mutants F382W/L328V; F382W/L328V/I187M; and A324L/S366G showed increase isoprene-production activity, relative to WT cdLD.

9. Further Characterization of the Activity of Clone 91 a. Study of the Effect of Individual Mutations in Clone 91

To analyze which of the mutations in clone 91 contribute to the increase in butadiene productions, each of the mutations was created individually in wild-type cdLD. Also, each mutation was individually removed from clone 91. The choice to focus on clone 91 was based on the fact that it was one of the clones that previously showed the highest level of activity. Mutagenesis was done by extension PCR. Mutations and corresponding primers are listed in Table 5 and FIG. 6. To create each mutant, two fragments were amplified. Left fragment was amplified by primers P1 (ATAG-GCGCCAGCAACCGCAC) (SEQ ID NO: 21) and the reverse primer shown in Table 5. The right fragment was amplified by the forward primer show in Table 6 and primer P2 (GCAGCAGCCAACTCAGCTTC) (SEQ ID NO: 22).

Each PCR amplification reaction contained 30 pmol of each primer and 100 ng of DNA template. Amplifications were carried out using Pfu Ultra II Hotstart DNA polymerase (Agilent, cat#600850-51). The PCR reaction (20 μL) was initially heated at 95° C. for 2.5 min followed by 30 cycles of denaturation at 94° C. for 15 sec., annealing at 55° C. for 15 sec. and extension at 72° C. for 1 min. Following amplification, PCR fragment was gel-purified by the QIAGEN® gel-band purification kit and mixed (50 ng of each fragment). These mixtures served as templates for the extension PCR by primers GibsV4ins-for (TTGTTTAACTTTAAGAAGGAGATTAC) and GibsV3ins-rev (GGCTTTGTTAGCAGCCGGATCT) (SEQ ID NOS 23-24, respectively) to generate the full-length gene fragment. The PCR conditions were same as described above. The full-length DNA fragment was gel-purified by the QIAGEN® gel-band purification kit. Next 4 μl (appr. 0.3 pmoles) of the PCR fragment was mixed with 1 ul of the amplified cloning vector (approximately 0.05 pmoles) and 5 μl of 2× Gibson Assembly mix (New England Biolabs, cat#M5510AA) and incubated 1 h at 50° C. Following incubation, each mix was diluted with sterile water (4-fold) and transformed in XL1Blue competent cells (Agilent) according to manufacturer's protocol. Transformed cells were plated on LB plates containing 50 μg/mL kanamycin and incubated overnight at 37° C. Next morning colonies were scraped from plate plasmid DNA was isolated using Qiagen Miniprep kit and transformed into BL21(DE3) competent cells (Invitrogen). Transformations were plated on LB plates containing 25 μg/mL kanamycin and incubated overnight at 37° C. Resulting colonies were picked into 400 ul of LB media containing 50 μg/mL kanamycin in deep-well 96-well plates and used further in the 1 ml butadiene screen (see above). Clones that produced butadiene at the levels comparable or higher than the wild type enzyme were regrown in several replicas and retested using the same 1 ml butadiene assay (secondary screen).

TABLE 5

Sequences of the reverse primers (SEQ ID NOS 25-36, respectively, in order of appearance) used to create mutations to deconvolute clone 91

| Variant | Reverse primer | Reverse primer sequence |
|---|---|---|
| Removal of V123I from clone 91 | 123V-R | ACATTTCATTTTTGAGACTGCAATATCTAAGTCGTGG |
| Removal of V204I from clone 91 | 204V-R | AGAGTTGCATTGTACAAAATAGTTGTCTGGTTCACAAAC |
| Removal of M274F from clone 91 | 274M-R | ATCCATTCCATGAATCATAGCTAACGTCCAAGCGGTTGT |
| Removal of V275I from clone 91 | 275I-R | GATCCATTCCATGCACGAAAGCTAACGTCCAAGCGGTTGT |
| M274F, V275I | 274F-275I-R | ATCCATTCCATGAATGAAAGCTAACGTCCAAGCGGTTGT |
| M274F | M274F-R | ATCCATTCCATGCACGAAAGCTAACGTCCAAGCGGTTGTA |
| V275I | V275I-R | GATCCATTCCATGAATCATAGCTAACGTCCAAGCGGTTGT |
| A324L | A324L-R | TAATAAAAGTGTGAATAAAGAGGCTAAACCCACACCACC |
| R360Y | R360Y-R | GCCTGGGTGTTCGTAnGTAnGAGGCTAGCAGAAACGATGCTT |
| F382W | F382W-R | GTAACAGAGCACCCCATCCGGCATGTACTTTGGCAAG |
| V123I | V123I-R | ACATTTCATTTTTGAAATTGCAATATCTAAGTCGTGG |
| V204I | V204I-R | CAGAGTTGCATTGAATAAAATAGTTGTCTGGTTCACAAAC |

TABLE 6

Sequences of the forward primers (SEQ ID NOS 37-48, respectively, in order of appearance) used to create mutations to deconvolute clone 9.

| Variant | Forward primer | Forward primer sequence |
|---|---|---|
| Removal of V123I from clone 91 | 123V-F | TTAGATATTGCAGTCTCAAAAATGAAATGTAAACGTGTATG |
| Removal of V204I from clone 91 | 204V-F | GACAACTATTTTGTACAATGCAACTCTGTGGCCTATTT |
| Removal of M274F from clone 91 | 274M-F | TGGACGTTAGCTATGATTCATGGAATGGATCCTGCCTTTTC |
| Removal of V275I from clone 91 | 275I-F | TGGACGTTAGCTTTCGTGCATGGAATGGATCCTGCCTTTTC |
| M274F, V275I | 274F-275I-F | TGGACGTTAGCTTTCATTCATGGAATGGATCCTGCCTTTTC |
| M274F | M274F-F | GCTTGGACGTTAGCTTTCGTGCATGGAATGGATCCTGCCTT |

TABLE 6-continued

Sequences of the forward primers (SEQ ID NOS 37-48, respectively, in order of appearance) used to create mutations to deconvolute clone 9.

| Variant | Forward primer | Forward primer sequence |
|---|---|---|
| V275I | V275I-F | ACGTTAGCTATGATTCATGGAATGGATCCTGCCT TTTC |
| A324L | A324L-F | GTGGGTTTAGCCTCTTTATTCACACTTTTATTAG CCCGCGAAA |
| R360Y | R360Y-F | GTTTCTGCTAGCCTCTACTACGAACACCCAGGCA GCCT |
| F382W | F382W-F | CAAAGTACATGCCGGATGGGGTGCTCTGTTACGT ATGC |
| V123I | V123I-F | TTAGATATTGCAATTTCAAAAATGAAATGTAAAC GTGTATG |
| V204I | V204I-F | GACAACTATTTTATTCAATGCAACTCTGTGGCCT ATTT |

A summary of the screening results are shown in Table 7. Several variants showed improved butadiene production. They had following combination of mutations: V123I/V204I/M274F; M274F/V275I/F382W; V275I/A324L; V275I; V123I; and V204I.

TABLE 7

Relative butadiene production by periplasmic variants of cdLD.

| Variant | Mutants | Relative Butadiene production (WT = 1) | Standard Deviation |
|---|---|---|---|
| 1 | V204I, M274F, V275I | 1.08 | 0.03 |
| 2 | V123I, M274F, V275I | 0.74 | |
| 3 | V123I, V204I, V275I | 0.89 | 0.17 |
| 4 | V123I, V204I, M274F | 1.265 | 0.01 |
| 5 | M274F, V275I | 0.45 | 0.11 |
| 6 | M274F, A324L | 0.55 | |
| 7 | M274F, R360Y | 0.67 | |
| 9 | M274F, V275I, A324L | 0.815 | 0.3 |
| 11 | M274F, V275I, F382W | 1.705 | 0.64 |
| 13 | M274F, A324L, F382W | 0.725 | 0.5 |
| 17 | M274F, V275I, R360Y, F382W | 0.905 | 0.42 |
| 21 | V275I, A324L | 1.66 | 0.34 |
| 23 | V275I, F382W | 0.84 | 0.07 |
| 24 | V275I, A324L, R360Y | 0.65 | 0.06 |
| 25 | V275I, A324L, F382W | 0.635 | 0.25 |
| 31 | R360Y, F382W | 1.235 | 0.47 |
| 32 | M274F | 0.675 | 0.01 |
| 33 | V275I | 2.135 | 0.33 |
| 34 | A324L | 1.64 | 0.04 |

TABLE 7-continued

Relative butadiene production by periplasmic variants of cdLD.

| Variant | Mutants | Relative Butadiene production (WT = 1) | Standard Deviation |
|---|---|---|---|
| 35 | R360Y | 1.925 | 0.02 |
| 36 | F382W | 0.72 | 0.1 |
| 37 | V123I | 1.925 | 0.6 |
| 38 | V204I | 1.55 | 0.07 |
| WT | WT cdLD | 1 | 0 |
| clone 91 | clone 91 | 1.425 | 0.15 | b. Combinatorial Mutagenesis

A number of mutants were created combining two or more of the improving mutations set forth in the previous sections. More specifically, several mutations were imposed on top of the following background mutants: A324L, S366V, A324L-S366G, M274-F96L, and F382W-L328V.

Figure 13:
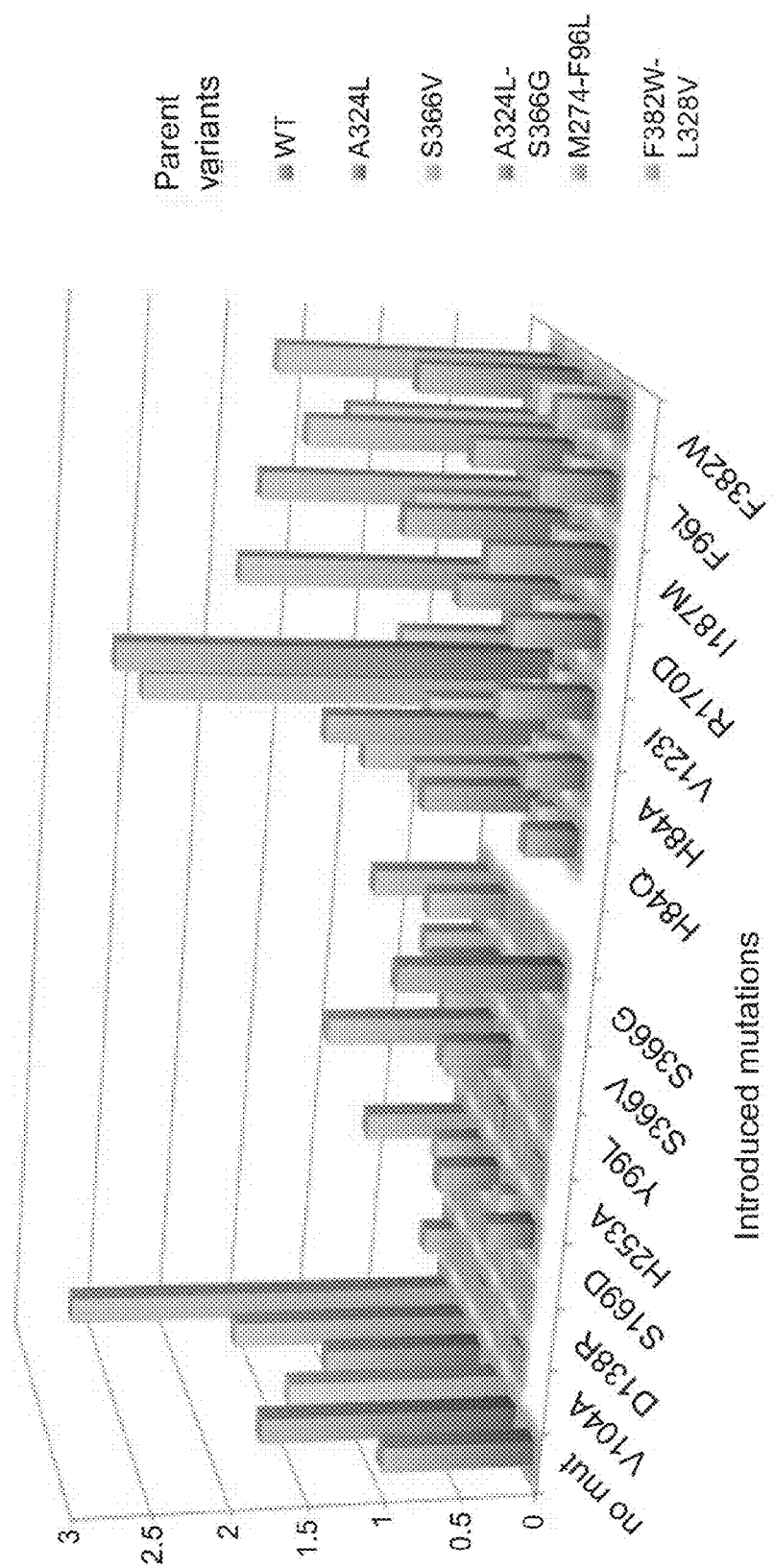
FIG. 13: Relative butadiene production by combinatorial mutants (1 ml assay).
Figure 14:
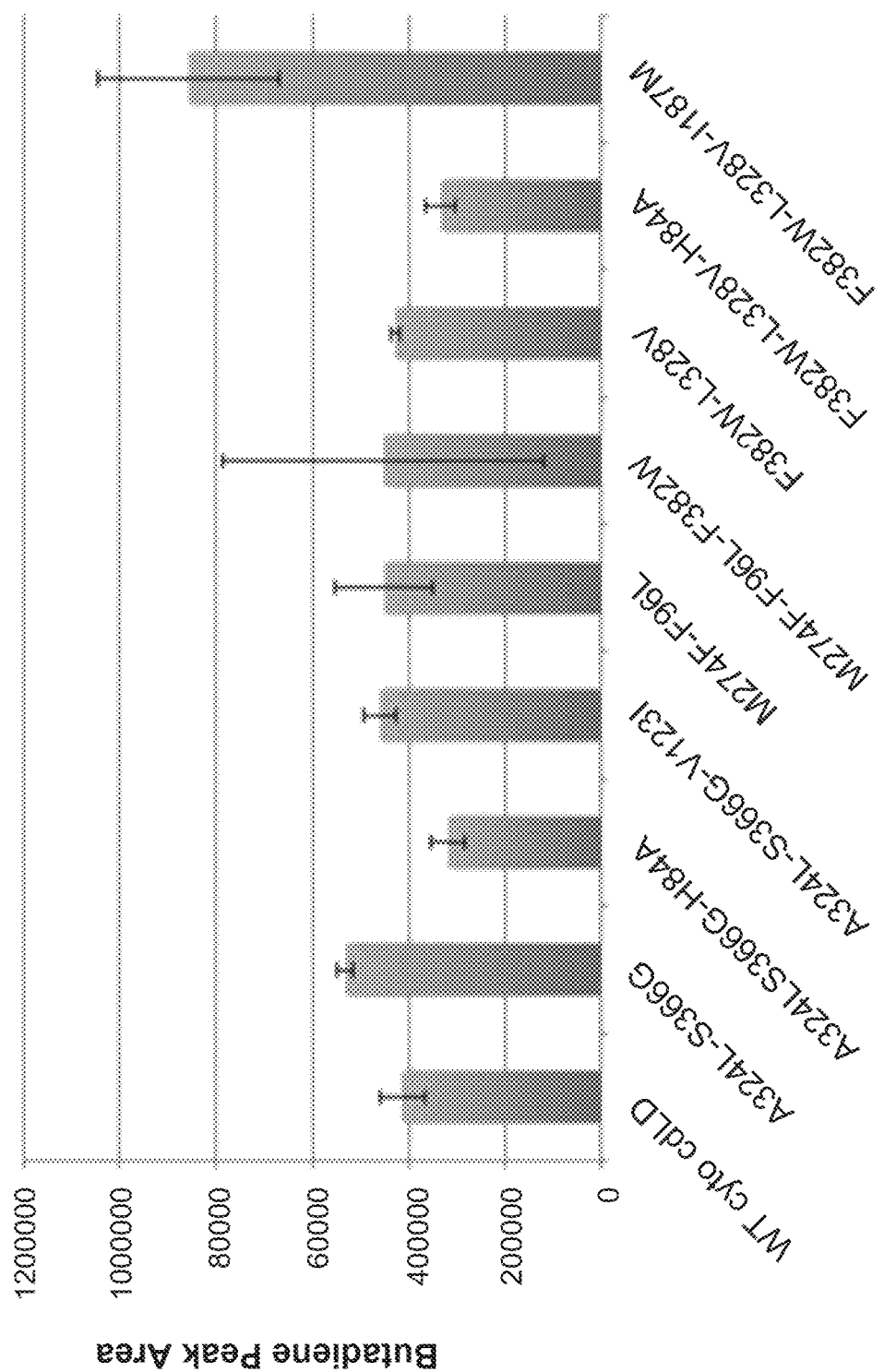
FIG. 14: Relative butadiene production by combinatorial mutants (1 ml assay).

Clones that produced butadiene at the levels comparable or higher than the wild type enzyme were regrown in several replicas and retested using the same 1 ml butadiene assay (secondary screen). Results of the assay of these clones are shown in FIG. 13. Addition of most tested mutations to A324L or S366V were not found to improve cdLD activity. Many of the variants showed no butadiene production. Therefore, it was assumed that these mutations have low combinatorial potential. Combining mutations together (A324L and S366V) generated a variant with no activity. At the same time adding mutations on top of combination of A324L and S366G generated several combinations that showed signs of improvement (addition of H84A and V123I). Adding mutations R170D F96L and F382W on top of combination of M274-F96L and mutation I187M on top of combination F382W-L328V also seemed to improve butadiene production in the 1 mL assay. These variants were retested in the secondary screen (FIG. 14) and only two variants appeared to exhibit higher butadiene production than wild type cdLD: combination of A324L, S366G and of F382W, L328V, I187M.

Figure 15:
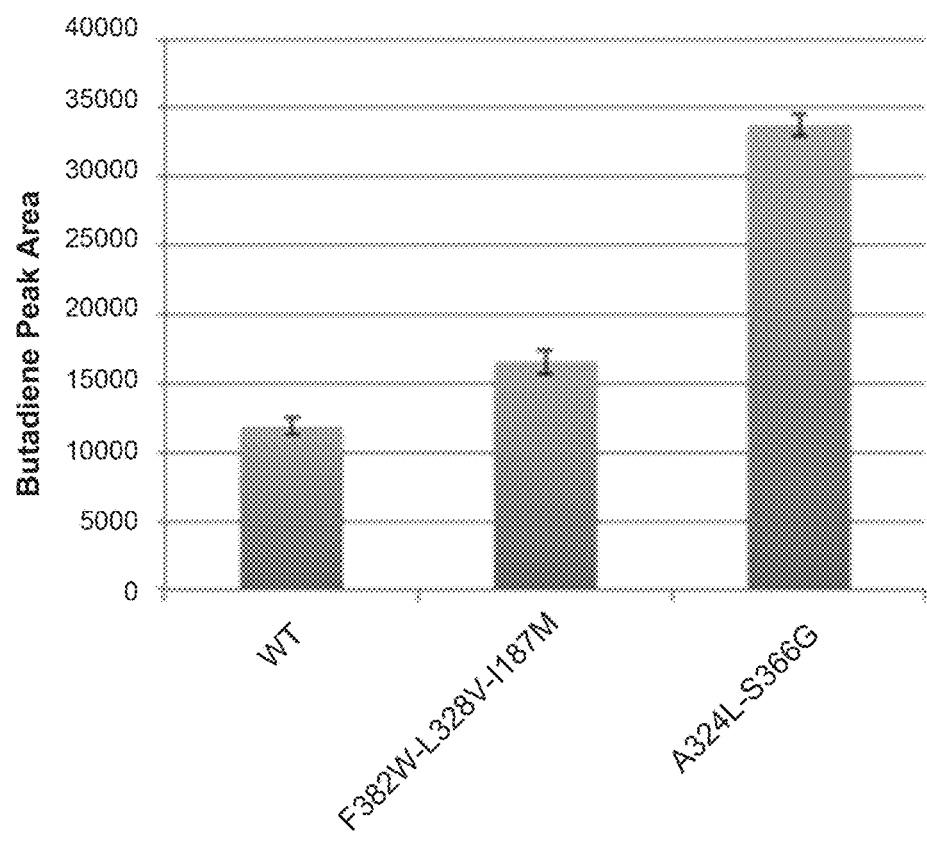
FIG. 15: Butadiene assay with purified cyto-cdLD mutants. Only two clones that showed significant improvement in specific activity over WT cdLD are shown.

Some of these mutants were purified as described in Example 2 and re-tested to establish whether their specific activity was higher than that of cdLD. Purified proteins were diluted to the same concentration. 250 ul of purified protein solution was transferred to a crimp vial along with 2.5 ul of 1.1M 3-buten-2-ol (final concentration of 11 mM), sealed and incubated at room temperature for 72 h. Following incubation samples were analyzed by Shimadzu GCMS-QP2010 Ultra with Agilent column HP PLOT/Q (0.32 mm, 15 m length, 20 um diameter) as before for the 1 ml butadiene assay. Results are presented in FIG. 15. Both variants (combination of A324L, S366G and of F382W, L328V, I187M) produce more butadiene then WT cdLD, with up to 3x the amount of butadiene produced for the A324L, S366G variant.

10. Sequences of the Polypeptides Described Herein.

Nucleotide and Amino-Acid Sequences of the cdLD Variants Constructed

TABLE 8

Nucleotide sequences of the cdLD variants constructed and described in the text (SEQ ID NOS 49-86, respectively, in order of appearance).

| Mutations | Nucleotide Sequence |
|---|---|
| Periplasmic cdLD | |
| Wild Type | atgATGCGTTTCACATTAAAGACCACCGCGATTGTTTCTGCCGCCGCGTTATTAGCGGG TTTTGGACCACCACCTCGTGCAGCAGAATTACCTCCCGGCCGCCTTGCCACAACCGA AGATTATTTCGCACAACAAGCAAAACAAGCTGTAACCCCGGATGTTATGGCTCAACTC |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| V123I,<br>V204I,<br>V275I, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATTTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGATTCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGCAGCCTCGAGCATCATCATCATCAT<br>CACTGA |
| V123I,<br>V204I,<br>M274F,<br>V275I, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATTTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTTTCATTCATGGAATGGATCCTGCCTTTTCAGAACGTTATTATCCTCGTTTTAAACA<br>AACGTTCGTCGAAGTCTATGATGAAGGCCGTAAAGCCCGCGTACGCGAAACTGCCGG<br>AACCGACGACGCCGATGGTGGTGTGGGTTTAGCCTCTGCGTTCACACTTTTATTAGCC<br>CGCGAAATGGGAGATCAACAACTCTTTGACCAACTGCTGAATCATTTAGAACCCCCTG<br>CCAAACCAAGCATCGTTTCTGCTAGCCTCCGCTACGAACACCCAGGCAGCCTCTTATT<br>CGACGAACTGTTATTTCTTGCCAAAGTACATGCCGGATTTGGTGCTCTGTTACGTATG<br>CCCCCTCCTGCCGCCAAATTAGCGGGCAAAGGCAGCCTCGAGCATCATCATCATCAT<br>CACTGA |
| V123I,<br>V204I,<br>M274F,<br>V275I,<br>A324L,<br>F382W | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATCTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTTTTATTCATGGAATGGATCCTGCCTTTTCAGAACGTTATTATCCTCGTTTTAAACA<br>AACGTTCGTCGAAGTCTATGATGAAGGCCGTAAAGCCCGCGTACGCGAAACTGCCGG<br>AACCGACGACGCCGATGGTGGTGTGGGTTTAGCCTCTTTGTTCACACTTTTATTAGCC<br>CGCGAAATGGGAGATCAACAACTCTTTGACCAACTGCTGAATCATTTAGAACCCCCTG<br>CCAAACCAAGCATCGTTTCTGCTAGCCTCCGCTACGAACACCCAGGCAGCCTCTTATT<br>CGACGAACTGTTATTTCTTGCCAAAGTACATGCCGGATGGGGTGCTCTGTTACGTATG<br>CCCCCTCCTGCCGCCAAATTAGCGGGCAAAGGCAGCCTCGAGCATCATCATCATCAT<br>CACTGA |
| A324L | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTTTATTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTGGTGCTCTGTTACGTATG<br>CCCCCTCCTGCCGCCAAATTAGCGGGCAAAGGTTCCctcgagcaccaccaccaccactga |
| R360Y | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCTACTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| V204I,<br>M274F,<br>V275I, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAGTCTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTTTCATTCATGGAATGGATCCTGCCTTTTCAGAACGTTATTATCCTCGTTTTAAACA<br>AACGTTCGTCGAAGTCTATGATGAAGGCCGTAAAGCCCGCGTACGCGAAACTGCCGG |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | AACCGACGACGCCGATGGTGGTGTGGGTTTAGCCTCTGCGTTCACACTTTTATTAGCC<br>CGCGAAATGGGAGATCAACAACTCTTTGACCAACTGCTGAATCATTTAGAACCCCCTG<br>CCAAACCAAGCATCGTTTCTGCTAGCCTCCGCTACGAACACCCAGGCAGCCTCTTATT<br>CGACGAACTGTTATTTCTTGCCAAAGTACATGCCGGATTTGGTGCTCTGTTACGTATG<br>CCCCCTCCTGCCGCCAAATTAGCGGGCAAAGGCAGCCTCGAGCATCATCATCATCAT<br>CACTGA |
| V123I,<br>M274F,<br>V275I, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATTTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTTTCATTCATGGAATGGATCCTGCCTTTTCAGAACGTTATTATCCTCGTTTTAAACA<br>AACGTTCGTCGAAGTCTATGATGAAGGCCGTAAAGCCCGCGTACGCGAAACTGCCGG<br>AACCGACGACGCCGATGGTGGTGTGGGTTTAGCCTCTGCGTTCACACTTTTATTAGCC<br>CGCGAAATGGGAGATCAACAACTCTTTGACCAACTGCTGAATCATTTAGAACCCCCTG<br>CCAAACCAAGCATCGTTTCTGCTAGCCTCCGCTACGAACACCCAGGCAGCCTCTTATT<br>CGACGAACTGTTATTTCTTGCCAAAGTACATGCCGGATTTGGTGCTCTGTTACGTATG<br>CCCCCTCCTGCCGCCAAATTAGCGGGCAAAGGCAGCCTCGAGCATCATCATCATCAT<br>CACTGA |
| V123I,<br>V204I,<br>V275I, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATTTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGATTCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGCAGCCTCGAGCATCATCATCATCAT<br>CACTGA |
| V123I,<br>V204I,<br>M274F, | ATGATGCGTTTCACATTAAAGACCACCGCGATTGTTTCTGCCGCCGCGTTATTAGCGG<br>GTTTTGGACCACCACCTCGTGCAGCAGAATTACCTCCCGGCCGCCTTGCCACAACCG<br>AAGATTATTTCGCACAACAAGCAAAACAAGCTGTAACCCCGGATGTTATGGCTCAACT<br>CGCGTACATGAACTATATTGATTTCATTAGCCCCTTTTATTCACGTGGATGTTCATTCG<br>AAGCATGGGAATTGAAACACACTCCGCAGCGCGTGATTAAATACTCCATTGCATTCTA<br>TGCTTATGGCTTGGCATCTGTAGCATTAATCGACCCTAAACTGCGCGCGCTCGCCGG<br>CCACGACTTAGATATTGCAATTTCAAAAATGAAATGTAAACGTGTATGGGGAGATTGG<br>GAAGAAGATGGTTTTGGTACAGATCCGATTGAAAAAGAAAACATTATGTATAAAGGACA<br>TCTGAACCTTATGTATGGTCTTTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTTTCGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG |

TABLE 8-continued

Nucleotide sequences of the cdLD variants constructed and
described in the text (SEQ ID NOS 49-86, respectively, in
order of appearance).

| Mutations | Nucleotide Sequence |
|---|---|
| | CCCCCTCCTGCCGCCAAATTAGCGGGCAAAGGCAGCCTCGAGCATCATCATCATCAT CACTGA |
| M274F, V275I, F382W | ATGATGCGTTTCACATTAAAGACCACCGCGATTGTTTCTGCCGCCGCGTTATTAGCGG GTTTTGGACCACCACCTCGTGCAGCAGAATTACCTCCCGGCCGCCTTGCCACAACCG AAGATTATTTCGCACAACAAGCAAAACAAGCTGTAACCCCGGATGTTATGGCTCAACT CGCGTACATGAACTATATTGATTTCATTAGCCCCTTTTATTCACGTGGATGTTCATTCG AAGCATGGGAATTGAAACACACTCCGCAGCGCGTGATTAAATACTCCATTGCATTCTA TGCTTATGGCTTGGCATCTGTAGCATTAATCGACCCTAAACTGCGCGCGCTCGCCGG CCACGACTTAGATATTGCAGTCTCAAAAATGAAATGTAAACGTGTATGGGGAGATTGG GAAGAAGATGGTTTTGGTACAGATCCGATTGAAAAAGAAAACATTATGTATAAGGACA TCTGAACCTTATGTATGGTCTTTATCAACTTGTTACTGGATCGCGCCGTTACGAAGCTG AACACGCTCACCTCACCCGTATTATCCACGACGAAATTGCCGCCAACCCATTCGCCGG AATCGTTTGTGAACCAGACAACTATTTTGTACAATGCAACTCTGTGGCCTATTTAAGCC TTTGGGTCTACGATCGTTTACATGGAACTGACTACCGTGCCGCAACTCGTGCCTGGCT GGATTTTATTCAAAAAGATCTGATTGACCCCGAACGTGGAGCTTTCTATTTGTCCTATC ATCCCGAATCTGGTGCCGTCAAACCTTGGATCAGCGCATATACAACCGCTTGGACGTT AGCTTTCATTCATGGAATGGATCCTGCCTTTTCAGAACGTTATTATCCTCGTTTTAAACA AACGTTCGTCGAAGTCTATGATGAAGGCCGTAAAGCCCGCGTACGCGAAACTGCCGG AACCGACGACGCCGATGGTGGTGTGGGTTTAGCCTCTGCGTTCACACTTTTATTAGCC CGCGAAATGGGAGATCAACAACTCTTTGACCAACTGCTGAATCATTTAGAACCCCCTG CCAAACCAAGCATCGTTTCTGCTAGCCTCCGCTACGAACACCCAGGCAGCCTCTTATT CGACGAACTGTTATTTCTTGCCAAAGTACATGCCGGATGGGGTGCTCTGTTACGTATG CCCCCTCCTGCCGCCAAATTAGCGGGCAAAGGCAGCCTCGAGCATCATCATCATCAT CACTGA |
| V275I, A324L | atgATGCGTTTCACATTAAAGACCACCGCGATTGTTTCTGCCGCCGCGTTATTAGCGGG TTTTGGACCACCACCTCGTGCAGCAGAATTACCTCCCGGCCGCCTTGCCACAACCGA AGATTATTTCGCACAACAAGCAAAACAAGCTGTAACCCCGGATGTTATGGCTCAACTC GCGTACATGAACTATATTGATTTCATTAGCCCCTTTTATTCACGTGGATGTTCATTCGA AGCATGGGAATTGAAACACACTCCGCAGCGCGTGATTAAATACTCCATTGCATTCTAT GCTTATGGCTTGGCATCTGTAGCATTAATCGACCCTAAACTGCGCGCGCTCGCCGGC CACGACTTAGATATTGCAGTCTCAAAAATGAAATGTAAACGTGTATGGGGAGATTGGG AAGAAGATGGTTTTGGTACAGATCCGATTGAAAAAGAAAACATTATGTATAAAGGACAT CTGAACCTTATGTATGGTCTCTATCAACTTGTTACTGGATCGCGCCGTTACGAAGCTG AACACGCTCACCTCACCCGTATTATCCACGACGAAATTGCCGCCAACCCATTCGCCGG AATCGTTTGTGAACCAGACAACTATTTTGTACAATGCAACTCTGTGGCCTATTTAAGCC TTTGGGTCTACGATCGTTTACATGGAACTGACTACCGTGCCGCAACTCGTGCCTGGCT GGATTTTATTCAAAAAGATCTGATTGACCCCGAACGTGGAGCTTTCTATTTGTCCTATC ATCCCGAATCTGGTGCCGTCAAACCTTGGATCAGCGCATATACAACCGCTTGGACGTT AGCTATGATTCATGGAATGGATCCTGCCTTTTCAGAACGTTATTATCCTCGTTTTAAAC AAACGTTCGTCGAAGTCTATGATGAAGGCCGTAAAGCCCGCGTACGCGAAACTGCCG GAACCGACGACGCCGATGGTGGTGTGGGTTTAGCCTCTTTATTCACACTTTTATTAGC CCGCGAAATGGGAGATCAACAACTCTTTGACCAACTGCTGAATCATTTAGAACCCCCT GCCAAACCAAGCATCGTTTCTGCTAGCCTCCGCTACGAACACCCAGGCAGCCTCTTAT TCGACGAACTGTTATTTCTTGCCAAAGTACATGCCGGATTTGGTGCTCTGTTACGTATG CCCCCTCCTGCCGCCAAATTAGCGGGCAAAGGTTCCctcgagcaccaccaccaccactga |
| M274F | atgATGCGTTTCACATTAAAGACCACCGCGATTGTTTCTGCCGCCGCGTTATTAGCGGG TTTTGGACCACCACCTCGTGCAGCAGAATTACCTCCCGGCCGCCTTGCCACAACCGA AGATTATTTCGCACAACAAGCAAAACAAGCTGTAACCCCGGATGTTATGGCTCAACTC GCGTACATGAACTATATTGATTTCATTAGCCCCTTTTATTCACGTGGATGTTCATTCGA AGCATGGGAATTGAAACACACTCCGCAGCGCGTGATTAAATACTCCATTGCATTCTAT GCTTATGGCTTGGCATCTGTAGCATTAATCGACCCTAAACTGCGCGCGCTCGCCGGC CACGACTTAGATATTGCAGTCTCAAAAATGAAATGTAAACGTGTATGGGGAGATTGGG AAGAAGATGGTTTTGGTACAGATCCGATTGAAAAAGAAAACATTATGTATAAAGGACAT CTGAACCTTATGTATGGTCTCTATCAACTTGTTACTGGATCGCGCCGTTACGAAGCTG AACACGCTCACCTCACCCGTATTATCCACGACGAAATTGCCGCCAACCCATTCGCCGG AATCGTTTGTGAACCAGACAACTATTTTGTACAATGCAACTCTGTGGCCTATTTAAGCC TTTGGGTCTACGATCGTTTACATGGAACTGACTACCGTGCCGCAACTCGTGCCTGGCT GGATTTTATTCAAAAAGATCTGATTGACCCCGAACGTGGAGCTTTCTATTTGTCCTATC ATCCCGAATCTGGTGCCGTCAAACCTTGGATCAGCGCATATACAACCGCTTGGACGTT AGCTTTCGTGCATGGAATGGATCCTGCCTTTTCAGAACGTTATTATCCTCGTTTTAAAC AAACGTTCGTCGAAGTCTATGATGAAGGCCGTAAAGCCCGCGTACGCGAAACTGCCG GAACCGACGACGCCGATGGTGGTGTGGGTTTAGCCTCTGCGTTCACACTTTTATTAGC CCGCGAAATGGGAGATCAACAACTCTTTGACCAACTGCTGAATCATTTAGAACCCCCT GCCAAACCAAGCATCGTTTCTGCTAGCCTCCGCTACGAACACCCAGGCAGCCTCTTAT TCGACGAACTGTTATTTCTTGCCAAAGTACATGCCGGATTTGGTGCTCTGTTACGTATG CCCCCTCCTGCCGCCAAATTAGCGGGCAAAGGTTCCctcgagcaccaccaccaccactga |
| V275I | atgATGCGTTTCACATTAAAGACCACCGCGATTGTTTCTGCCGCCGCGTTATTAGCGGG TTTTGGACCACCACCTCGTGCAGCAGAATTACCTCCCGGCCGCCTTGCCACAACCGA AGATTATTTCGCACAACAAGCAAAACAAGCTGTAACCCCGGATGTTATGGCTCAACTC GCGTACATGAACTATATTGATTTCATTAGCCCCTTTTATTCACGTGGATGTTCATTCGA |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGATTCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| A324L | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTCTTATTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| R360Y | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCTACTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| F382W | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTGTACAATGCAACTCTGTGGCCTATTTAAGCC<br>TTTGGGTCTACGATCGTTTACATGGAACTGACTACCGTGCCGCAACTCGTGCCTGGCT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATGGGGTGCTCTGTTACGTAT<br>GCCCCCTCCTGCCGCAAATTAGCGGGCAAAGGTTCCctcgagcaccaccaccaccactga |
| V123I | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAATTTCAAAAATGAAATGTAAACGTGTATGGGGAGATTGGGA<br>AGAAGATGGTTTTGGTACAGATCCGATTGAAAAGAAAACATTATGTATAAAGGACATC<br>TGAACCTTATGTATGGTCTCTATCAACTTGTTACTGGATCGCGCCGTTACGAAGCTGAA<br>CACGCTCACCTCACCCGTATTATCCACGACGAAATTGCCGCCAACCCATTCGCCGGAA<br>TCGTTTGTGAACCAGACAACTATTTTGTACAATGCAACTCTGTGGCCTATTTAAGCCTT<br>TGGGTCTACGATCGTTTACATGGAACTGACTACCGTGCCGCAACTCGTGCCTGGCTG<br>GATTTTATTCAAAAAGATCTGATTGACCCCGAACGTGGAGCTTTCTATTTGTCCTATCA<br>TCCCGAATCTGGTGCCGTCAAACCTTGGATCAGCGCATATACAACCGCTTGGACGTTA<br>GCTATGGTGCATGGAATGGATCCTGCCTTTTCAGAACGTTATTATCCTCGTTTTAAACA<br>AACGTTCGTCGAAGTCTATGATGAAGGCCGTAAAGCCCGCGTACGCGAAACTGCCGG<br>AACCGACGACGCCGATGGTGGTGTGGGTTTAGCCTCTGCGTTCACACTTTTATTAGCC<br>CGCGAAATGGGAGATCAACAACTCTTTGACCAACTGCTGAATCATTTAGAACCCCCTG<br>CCAAACCAAGCATCGTTTCTGCTAGCCTCCGCTACGAACACCCAGGCAGCCTCTTATT<br>CGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| V204I | atgATGCGTTTCACATTAAAGACCACCGCGATTGTTTCTGCCGCCGCGTTATTAGCGGG<br>TTTTGGACCACCACCTCGTGCAGCAGAATTACCTCCCGGCCGCCTTGCCACAACCGA<br>AGATTATTTCGCACAACAAGCAAAACAAGCTGTAACCCCGGATGTTATGGCTCAACTC<br>GCGTACATGAACTATATTGATTTCATTAGCCCCTTTTATTCACGTGGATGTTCATTCGA<br>AGCATGGGAATTGAAACACACTCCGCAGCGCGTGATTAAATACTCCATTGCATTCTAT<br>GCTTATGGCTTGGCATCTGTAGCATTAATCGACCCTAAACTGCGCGCGCTCGCCGGC<br>CACGACTTAGATATTGCAGTCTCAAAAATGAAATGTAAACGTGTATGGGGAGATTGGG<br>AAGAAGATGGTTTTGGTACAGATCCGATTGAAAAGAAAACATTATGTATAAAGGACAT<br>CTGAACCTTATGTATGGTCTCTATCAACTTGTTACTGGATCGCGCCGTTACGAAGCTG<br>AACACGCTCACCTCACCCGTATTATCCACGACGAAATTGCCGCCAACCCATTCGCCGG<br>AATCGTTTGTGAACCAGACAACTATTTTATTCAATGCAACTCTGTGGCCTATTTAAGCC<br>TTTGGGTCTACGATCGTTTACATGGAACTGACTACCGTGCCGCAACTCGTGCCTGGCT<br>GGATTTTATTCAAAAAGATCTGATTGACCCCGAACGTGGAGCTTTCTATTTGTCCTATC<br>ATCCCGAATCTGGTGCCGTCAAACCTTGGATCAGCGCATATACAACCGCTTGGACGTT<br>AGCTATGGTGCATGGAATGGATCCTGCCTTTTCAGAACGTTATTATCCTCGTTTTAAAC<br>AAACGTTCGTCGAAGTCTATGATGAAGGCCGTAAAGCCCGCGTACGCGAAACTGCCG<br>GAACCGACGACGCCGATGGTGGTGTGGGTTTAGCCTCTGCGTTCACACTTTTATTAGC<br>CCGCGAAATGGGAGATCAACAACTCTTTGACCAACTGCTGAATCATTTAGAACCCCCT<br>GCCAAACCAAGCATCGTTTCTGCTAGCCTCCGCTACGAACACCCAGGCAGCCTCTTAT<br>TCGACGAACTGTTATTTCTTGCCAAAGTACATGCCGGATTTGGTGCTCTGTTACGTATG<br>CCCCCTCCTGCCGCCAAATTAGCGGGCAAAGGTTCCctcgagcaccaccaccaccactga |
| Cytolpasmic cdLD | |
| WT | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| A324L | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTCTGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| V204I | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTATTCAATGCAACTCTGTGGCCTATTTAAGCCTTTGGGTCTACGATCGTTTACAT<br>GGAACTGACTACCGTGCCGCAACTCGTGCCTGGCTGGATTTTATTCAAAAAGATCTG<br>TTGACCCCGAACGTGGAGCTTTCTATTTGTCCTATCATCCCGAATCTGGTGCCGTCAA<br>ACCTTGGATCAGCGCATATACAACCGCTTGGACGTTAGCTATGGTGCATGGAATGGAT<br>CCTGCCTTTTCAGAACGTTATTATCCTCGTTTTAAACAAACGTTCGTCGAAGTCTATGA<br>TGAAGGCCGTAAAGCCCGCGTACGCGAAACTGCCGGAACCGACGACGCCGATGGTG<br>GTGTGGGTTTAGCCTCTGCGTTCACACTTTTATTAGCCCGCGAAATGGGAGATCAACA<br>ACTCTTTGACCAACTGCTGAATCATTTAGAACCCCCTGCCAAACCAAGCATCGTTTCTG<br>CTAGCCTCCGCTACGAACACCCAGGCAGCCTCTTATTCGACGAACTGTTATTTCTTGC<br>CAAAGTACATGCCGGATTTGGTGCTCTGTTACGTATGCCCCCTCCTGCCGCCAAATTA<br>GCGGGCAAAGGTTCCctcgagCACCACCACCACCACCACTGA |
| M274F | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTTTCGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| V275I | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGATTCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| F382W | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATGGGGTGCTCTGTTACGTATGCCCCCTCCTGCCGCCAAAT<br>TAGCGGGCAAAGGTTCCctcgagCACCACCACCACCACCACTGA |
| S366V | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCGTGCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| A324L-<br>S366G | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTCTGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCGGGCTCTTATTCGACGAACTGTTATTTCTTG |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| M274F-<br>F96L | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCACTTTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTTTCGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| M274F-<br>Y99L<br>(CTC) | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTCTTGGCTTGGCATCTGTA<br>GCATTAATCGACCCTAAACTGCGCGCGCTCGCCGGCCACGACTTAGATATTGCAGTCT<br>CAAAAATGAAATGTAAACGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTTTCGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| M274F-<br>Y99L<br>(CTG) | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTCTGGGCTTGGCATCTGT<br>AGCATTAATCGACCCTAAACTGCGCGCGCTCGCCGGCCACGACTTAGATATTGCAGT<br>CTCAAAAATGAAATGTAAACGTATGGGGAGATTGGGAAGAAGATGGTTTTGGTACA<br>GATCCGATTGAAAAAGAAAACATTATGTATAAAGGACATCTGAACCTTATGTATGGTCT<br>CTATCAACTTGTTACTGGATCGCGCCGTTACGAAGCTGAACACGCTCACCTCACCCGT<br>ATTATCCACGACGAAATTGCCGCCAACCCATTCGCCGGAATCGTTTGTGAACCAGACA<br>ACTATTTTGTACAATGCAACTCTGTGGCCTATTTAAGCCTTTGGGTCTACGATCGTTTA<br>CATGGAACTGACTACCGTGCCGCAACTCGTGCCTGGCTGGATTTTATTCAAAAAGATC<br>TGATTGACCCCGAACGTGGAGCTTTCTATTTGTCCTATCATCCCGAATCTGGTGCCGT<br>CAAACCTTGGATCAGCGCATATACAACCGCTTGGACGTTAGCTTTCGTGCATGGAATG<br>GATCCTGCCTTTTCAGAACGTTATTATCCTCGTTTTAAACAAACGTTCGTCGAAGTCTA<br>TGATGAAGGCCGTAAAGCCCGCGTACGCGAAACTGCCGGAACCGACGACGCCGATG<br>GTGGTGTGGGTTTAGCCTCTGCGTTCACACTTTTATTAGCCCGCGAAATGGGAGATCA<br>ACAACTCTTTGACCAACTGCTGAATCATTTAGAACCCCCTGCCAAACCAAGCATCGTTT<br>CTGCTAGCCTCCGCTACGAACACCCAGGCAGCCTCTTATTCGACGAACTGTTATTTCT<br>TGCCAAAGTACATGCCGGATTTGGTGCTCTGTTACGTATGCCCCCTCCTGCCGCCAAA<br>TTAGCGGGCAAAGGTTCCctcgagCACCACCACCACCACCACTGA |
| M274F-<br>Y99L<br>(TTG) | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTTGGGCTTGGCATCTGT<br>AGCATTAATCGACCCTAAACTGCGCGCGCTCGCCGGCCACGACTTAGATATTGCAGT<br>CTCAAAAATGAAATGTAAACGTATGGGGAGATTGGGAAGAAGATGGTTTTGGTACA<br>GATCCGATTGAAAAAGAAAACATTATGTATAAAGGACATCTGAACCTTATGTATGGTCT<br>CTATCAACTTGTTACTGGATCGCGCCGTTACGAAGCTGAACACGCTCACCTCACCCGT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | ATTATCCACGACGAAATTGCCGCCAACCCATTCGCCGGAATCGTTTGTGAACCAGACA<br>ACTATTTTGTACAATGCAACTCTGTGGCCTATTTAAGCCTTTGGGTCTACGATCGTTTA<br>CATGGAACTGACTACCGTGCCGCAACTCGTGCCTGGCTGGATTTTATTCAAAAAGATC<br>TGATTGACCCCGAACGTGGAGCTTTCTATTTGTCCTATCATCCCGAATCTGGTGCCGT<br>CAAACCTTGGATCAGCGCATATACAACCGCTTGGACGTTAGCTTTCGTGCATGGAATG<br>GATCCTGCCTTTTCAGAACGTTATTATCCTCGTTTTAAACAAACGTTCGTCGAAGTCTA<br>TGATGAAGGCCGTAAAGCCCGCGTACGCGAAACTGCCGGAACCGACGACGCCGATG<br>GTGGTGTGGGTTTAGCCTCTGCGTTCACACTTTTATTAGCCCGCGAAATGGGAGATCA<br>ACAACTCTTTGACCAACTGCTGAATCATTTAGAACCCCTGCCAAACCAAGCATCGTTT<br>CTGCTAGCCTCCGCTACGAACACCCAGGCAGCCTCTTATTCGACGAACTGTTATTTCT<br>TGCCAAAGTACATGCCGGATTTGGTGCTCTGTTACGTATGCCCCCTCCTGCCGCCAAA<br>TTAGCGGGCAAAGGTTCCctcgagCACCACCACCACCACCACTGA |
| S366V-<br>L367V<br>(GTG) | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCTGCCAAACCAAGCATCGTTTCT<br>GCTAGCCTCCGCTACGAACACCCAGGCGTGGTGTTATTCGACGAACTGTTATTTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |
| F382W-<br>L212Y | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTATAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATGGGGTGCTCTGTTACGTATGCCCCCTCCTGCCGCCAAAT<br>TAGCGGGCAAAGGTTCCctcgagCACCACCACCACCACCACTGA |
| F382W<br>only | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATCTGAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCTGCCAAACCAAGCATCGTTTCT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | GCTAGCCTCCGCTACGAACACCCAGGCAGCCTCTTATTCGACGAACTGTTATTTCTTG<br>CCAAAGTACATGCCGGATGGGGTGCTCTGTTACGTATGCCCCCTCCTGCCGCCAAAT<br>TAGCGGGCAAAGGTTCCctcgagCACCACCACCACCACCACTGA |
| F382W-<br>L328V | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTGTGTTAGCCCGCGAAATGGGAGATCAA<br>CAACTCTTTGACCAACTGCTGAATCATTTAGAACCCCCTGCCAAACCAAGCATCGTTTC<br>TGCTAGCCTCCGCTACGAACACCCAGGCAGCCTCTTATTCGACGAACTGTTATTTCTT<br>GCCAAAGTACATGCCGGATGGGGTGCTCTGTTACGTATGCCCCCTCCTGCCGCCAAA<br>TTAGCGGGCAAAGGTTCCctcgagCACCACCACCACCACCACTGA |
| F382W-<br>L328V-<br>I187M | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATGGCCGCCAACCCATTCGCCGGAATCGTTTGTGAACCAGACAA<br>CTATTTTGTACAATGCAACTCTGTGGCCTATTTAAGCCTTTGGGTCTACGATCGTTTAC<br>ATGGAACTGACTACCGTGCCGCAACTCGTGCCTGGCTGGATTTTATTCAAAAAGATCT<br>GATTGACCCCGAACGTGGAGCTTTCTATTTGTCCTATCATCCCGAATCTGGTGCCGTC<br>AAACCTTGGATCAGCGCATATACAACCGCTTGGACGTTAGCTATGGTGCATGGAATGG<br>ATCCTGCCTTTTCAGAACGTTATTATCCTCGTTTTAAACAAACGTTCGTCGAAGTCTAT<br>GATGAAGGCCGTAAAGCCCGCGTACGCGAAACTGCCGGAACCGACGACGCCGATGG<br>TGGTGTGGGTTTAGCCTCTGCGTTCACACTTGTGTTAGCCCGCGAAATGGGAGATCAA<br>CAACTCTTTGACCAACTGCTGAATCATTTAGAACCCCCTGCCAAACCAAGCATCGTTTC<br>TGCTAGCCTCCGCTACGAACACCCAGGCAGCCTCTTATTCGACGAACTGTTATTTCTT<br>GCCAAAGTACATGCCGGATGGGGTGCTCTGTTACGTATGCCCCCTCCTGCCGCCAAA<br>TTAGCGGGCAAAGGTTCCctcgagCACCACCACCACCACCACTGA |
| M274F-<br>F96L-<br>F382W | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCACTTTATGCTTATGGCTTGGCATCTGTA<br>GCATTAATCGACCCTAAACTGCGCGCGCTCGCCGGCCACGACTTAGATATTGCAGTCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT<br>ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTTTCGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTGCGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCAGCCTCTTATTCGACGAACTGTTATTTCTTG<br>CCAAAGTACATGCCGGATGGGGTGCTCTGTTACGTATGCCCCCTCCTGCCGCCAAAT<br>TAGCGGGCAAAGGTTCCctcgagCACCACCACCACCACCACTGA |
| A324L-<br>S366G-<br>V123I | ATGGCAGAATTACCTCCCGGCCGCCTTGCCACAACCGAAGATTATTTCGCACAACAAG<br>CAAAACAAGCTGTAACCCCGGATGTTATGGCTCAACTCGCGTACATGAACTATATTGA<br>TTTCATTAGCCCCTTTTATTCACGTGGATGTTCATTCGAAGCATGGGAATTGAAACACA<br>CTCCGCAGCGCGTGATTAAATACTCCATTGCATTCTATGCTTATGGCTTGGCATCTGTA<br>GCATTAATCGACCCTAAACTGCGCGCGCTCGCCGGCCACGACTTAGATATTGCAATCT<br>CAAAAATGAAATGTAAACGTGTATGGGGAGATTGGGAAGAAGATGGTTTTGGTACAGA<br>TCCGATTGAAAAAGAAAACATTATGTATAAAGGACATCTGAACCTTATGTATGGTCTCT |

TABLE 8-continued

Nucleotide sequences of the cdLD variants constructed and described in the text (SEQ ID NOS 49-86, respectively, in order of appearance).

| Mutations | Nucleotide Sequence |
|---|---|
| | ATCAACTTGTTACTGGATCGCGCCGTTACGAAGCTGAACACGCTCACCTCACCCGTAT<br>TATCCACGACGAAATTGCCGCCAACCCATTCGCCGGAATCGTTTGTGAACCAGACAAC<br>TATTTTGTACAATGCAACTCTGTGGCCTATTTAAGCCTTTGGGTCTACGATCGTTTACA<br>TGGAACTGACTACCGTGCCGCAACTCGTGCCTGGCTGGATTTTATTCAAAAAGATCTG<br>ATTGACCCCGAACGTGGAGCTTTCTATTTGTCCTATCATCCCGAATCTGGTGCCGTCA<br>AACCTTGGATCAGCGCATATACAACCGCTTGGACGTTAGCTATGGTGCATGGAATGGA<br>TCCTGCCTTTTCAGAACGTTATTATCCTCGTTTTAAACAAACGTTCGTCGAAGTCTATG<br>ATGAAGGCCGTAAAGCCCGCGTACGCGAAACTGCCGGAACCGACGACGCCGATGGT<br>GGTGTGGGTTTAGCCTCTCTGTTCACACTTTTATTAGCCCGCGAAATGGGAGATCAAC<br>AACTCTTTGACCAACTGCTGAATCATTTAGAACCCCCTGCCAAACCAAGCATCGTTTCT<br>GCTAGCCTCCGCTACGAACACCCAGGCGGTCTCTTATTCGACGAACTGTTATTCTTG<br>CCAAAGTACATGCCGGATTTGGTGCTCTGTTACGTATGCCCCCTCCTGCCGCCAAATT<br>AGCGGGCAAAGGTTCCctcgagCACCACCACCACCACCACTGA |

TABLE 9

Amino-acid sequences of the cdLD variants constructed and described in the text (SEQ ID NOS 4 and 88-123, respectively, in order of appearance)

| Mutations | Protein Sequence |
|---|---|
| Periplasmic cdLD | |
| Wild Type SEQ ID NO: 4 | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGFGALLRMPPPAAKLAGKGSLEHHHHHH |
| V123I,<br>V204I,<br>V275I, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAMIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| V123I,<br>V204I,<br>M274F,<br>V275I, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAFIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| V123I,<br>V204I,<br>M274F,<br>V275I,<br>A324L,<br>F382W | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAFIHGMDPAFSERYYPRFKQTFVEVYDEGRKA<br>RVRETAGTDDADGGVGLASLFTLLLAREMGDQQLFDQLLNHLEPPAKPSIVSASLRYEHP<br>GSLLFDELLFLAKVHAGWGALLRMPPPAAKLAGKGSLEHHHHHH |
| A324L | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASLFTLLLAREMGDQQLFDQLLNHLEPPAKPSIVSASLRYEH<br>PGSLLFDELLFLAKVHAGFGALLRMPPPAAKLAGKGSLEHHHHHH |
| R360Y | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK |

TABLE 9-continued

Amino-acid sequences of the cdLD variants constructed and described in the text (SEQ ID NOS 4 and 88-123, respectively, in order of appearance)

| Mutations | Protein Sequence |
|---|---|
| | ARVRETAGTDDADGGVGLASAFTLLLAREMGDQQLFDQLLNHLEPPAKPSIVSASLYYEH<br>PGSLLFDELLFLAKVHAGFGALLRMPPPAAKLAGKGSLEHHHHHH |
| V204I,<br>M274F,<br>V275I, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAFIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| V123I,<br>M274F,<br>V275I, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAFIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| V123I,<br>V204I,<br>V275I, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAMIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| V123I,<br>V204I,<br>M274F, | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAFVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGFGALLRMPPPAAKLAGKGSLEHHHHHH |
| M274F,<br>V275I,<br>F382W | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAFIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGWGALLRMPPPAAKLAGKGSLEHHHHHH |
| V275I,<br>A324L | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMIHGMDPAFSERYYPRFKQTFVEVYDEGRKA<br>RVRETAGTDDADGGVGLASLFTLLLAREMGDQQLFDQLLNHLEPPAKPSIVSASLRYEHP<br>GSLLFDELLFLAKVHAGFGALLRMPPPAAKLAGKGSLEHHHHHH |
| M274F | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAFVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGFGALLRMPPPAAKLAGKGSLEHHHHHH |
| V275I | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMIHGMDPAFSERYYPRFKQTFVEVYDEGRKA<br>RVRETAGTDDADGGVGLASAFTLLLAREMGDQQLFDQLLNHLEPPAKPSIVSASLRYEHP<br>GSLLFDELLFLAKVHAGFGALLRMPPPAAKLAGKGSLEHHHHHH |
| A324L | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASLFTLLLAREMGDQQLFDQLLNHLEPPAKPSIVSASLRYEH<br>PGSLLFDELLFLAKVHAGFGALLRMPPPAAKLAGKGSLEHHHHHH |

TABLE 9-continued

Amino-acid sequences of the cdLD variants constructed and described in the text (SEQ ID NOS 4 and 88-123, respectively, in order of appearance)

| Mutations | Protein Sequence |
|---|---|
| R360Y | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASAFTLLLAREMGDQQLFDQLLNHLEPPAKPSIVSASLYYEH<br>PGSLLFDELLFLAKVHAGFGALLRMPPPAAKLAGKGSLEHHHHHH |
| F382W | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGWGALLRMPPPAAKLAGKGSLEHHHHHH |
| V123I | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAI<br>SKMKCKRVWGDWEEDGFGTDPIEKENIMYKGHLNLMYGLYQLVTGSRRYEAEHAHLTRII<br>HDEIAANPFAGIVCEPDNYFVQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGFGALLRMPPPAAKLAGKGSLEHHHHHH |
| V204I | MMRFTLKTTAIVSAAALLAGFGPPPRAAELPPGRLATTEDYFAQQAKQAVTPDVMAQLAY<br>MNYIDFISPFYSRGCSFEAWELKHTPQRVIKYSIAFYAYGLASVALIDPKLRALAGHDLDIAV<br>SKMKCKRVWGDWEEDGFGTDPIEKENIMYKGHLNLMYGLYQLVTGSRRYEAEHAHLTRII<br>HDEIAANPFAGIVCEPDNYFIQCNSVAYLSLWVYDRLHGTDYRAATRAWLDFIQKDLIDPE<br>RGAFYLSYHPESGAVKPWISAYTTAWTLAMVHGMDPAFSERYYPRFKQTFVEVYDEGRK<br>ARVRETAGTDDADGGVGLASAFTLLLAREMGDQQLFDQLLNHLEPPAKPSIVSASLRYEH<br>PGSLLFDELLFLAKVHAGFGALLRMPPPAAKLAGKGSLEHHHHHH |
| Cytoplasmic<br>cdLD<br>SEQ ID<br>NO: 5 | |
| WT | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| A324L | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASLFTLL<br>LAREMGDQQLFDQLLNHLEPPAKPSIVSASLRYEHPGSLLFDELLFLAKVHAGFGALLRMP<br>PPAAKLAGKGSLEHHHHHH |
| V204I | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFIQCNSV<br>AYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| M274F | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| V275I | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA |

TABLE 9-continued

Amino-acid sequences of the cdLD variants constructed and described in the text (SEQ ID NOS 4 and 88-123, respectively, in order of appearance)

| Mutations | Protein Sequence |
|---|---|
| | WTLAMIHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| F382W | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGWGALLRM<br>PPPAAKLAGKGSLEHHHHHH |
| S366V | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGVLLFDELLFLAKVHAGFGALLRMP<br>PPAAKLAGKGSLEHHHHHH |
| A324L-<br>S366G | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASLFTLL<br>LAREMGDQQLFDQLLNHLEPPAKPSIVSASLRYEHPGGLLFDELLFLAKVHAGFGALLRMP<br>PPAAKLAGKGSLEHHHHHH |
| M274F-<br>F96L | MAELPPGRLATTEDYFAQQAKQAVTPDVMAQLAYMNYIDFISPFYSRGCSFEAWELKHTP<br>QRVIKYSIALYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| M274F-<br>Y99L<br>(CTC) | MAELPPGRLATTEDYFAQQAKQAVTPDVMAQLAYMNYIDFISPFYSRGCSFEAWELKHTP<br>QRVIKYSIAFYALGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| M274F-<br>Y99L<br>(CTG) | MAELPPGRLATTEDYFAQQAKQAVTPDVMAQLAYMNYIDFISPFYSRGCSFEAWELKHTP<br>QRVIKYSIAFYALGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| M274F-<br>Y99L<br>(TTG) | MAELPPGRLATTEDYFAQQAKQAVTPDVMAQLAYMNYIDFISPFYSRGCSFEAWELKHTP<br>QRVIKYSIAFYALGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGFGALLRMP<br>PPAAKLAGKGSLEHHHHHH |
| S366V-<br>L367V<br>(GTG) | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGVVLFDELLFLAKVHAGFGALLRMP<br>PPAAKLAGKGSLEHHHHHH |
| F382W-<br>L212Y | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYYSLWVYDRLHGTDYRAATRAWLDFIQKDLIDPERGAFYLSYHPESGAVKPWISAYTT |

TABLE 9-continued

Amino-acid sequences of the cdLD variants constructed and
described in the text (SEQ ID NOS 4 and 88-123, respectively, in
order of appearance)

| Mutations | Protein Sequence |
|---|---|
|  | AWTLAMVHGMDPAFSERYYPRFKQTFVEVYDEGRKARVRETAGTDDADGGVGLASAFT<br>LLLAREMGDQQLFDQLLNHLEPPAKPSIVSASLRYEHPGSLLFDELLFLAKVHAGWGALLR<br>MPPPAAKLAGKGSLEHHHHHH |
| F382W only | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGWGALLRM<br>PPPAAKLAGKGSLEHHHHHH |
| F382W-<br>L328V | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTL<br>VLAREMGDQQLFDQLLNHLEPPAKPSIVSASLRYEHPGSLLFDELLFLAKVHAGWGALLR<br>MPPPAAKLAGKGSLEHHHHHH |
| F382W-<br>L328V-<br>I187M | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEMAANPFAGIVCEPDNYFVQCNS<br>VAYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASAFTL<br>VLAREMGDQQLFDQLLNHLEPPAKPSIVSASLRYEHPGSLLFDELLFLAKVHAGWGALLR<br>MPPPAAKLAGKGSLEHHHHHH |
| M274F-<br>F96L-<br>F382W | MAELPPGRLATTEDYFAQQAKQAVTPDVMAQLAYMNYIDFISPFYSRGCSFEAWELKHTP<br>QRVIKYSIALYAYGLASVALIDPKLRALAGHDLDIAVSKMKCKRVWGDWEEDGFGTDPIEK<br>ENIMYKGHLNLMYGLYQLVTGSRRYEAEHAHLTRIIHDEIAANPFAGIVCEPDNYFVQCNS<br>VAYLSLWVYDRLHGTDYRAATRAWLDFIQKDLIDPERGAFYLSYHPESGAVKPWISAYTTA<br>WTLAFVHGMDPAFSERYYPRFKQTFVEVYDEGRKARVRETAGTDDADGGVGLASAFTLL<br>LAREMGDQQLFDQLLNHLEPPAKPSIVSASLRYEHPGSLLFDELLFLAKVHAGWGALLRM<br>PPPAAKLAGKGSLEHHHHHH |
| A324L-<br>S366G-<br>V123I | MAELPPGRLATTEDYFAQQAKQAVTPDVMAQLAYMNYIDFISPFYSRGCSFEAWELKHTP<br>QRVIKYSIAFYAYGLASVALIDPKLRALAGHDLDIAISKMKCKRVWGDWEEDGFGTDPIEKE<br>NIMYKGHLNLMYGLYQLVTGSRRYEAEHAHLTRIIHDEIAANPFAGIVCEPDNYFVQCNSV<br>AYLSLWVYDRLHGTDYRAATRAWLDFIQKDLIDPERGAFYLSYHPESGAVKPWISAYTTA<br>WTLAMVHGMDPAFSERYYPRFKQTFVEVYDEGRKARVRETAGTDDADGGVGLASLFTLL<br>LAREMGDQQLFDQLLNHLEPPAKPSIVSASLRYEHPGGLLFDELLFLAKVHAGFGALLRMP<br>PPAAKLAGKGSLEHHHHHH |

Appendix 1 (Novalix coordinates; filed as txt a separate txt file and incorporated by reference)

Appendix 2 (Emerald coordinates; filed as txt a separate txt file and incorporated by reference)

Appendix 3 (FASTA SEQUENCES OF MUTANTS TESTED) (SEQ ID NOS 124-458, respectively, in order of appearance; filed as txt a separate txt file and incorporated by reference)

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10519433B2). An electronic copy of the "Sequence Listing" will also be available from the USPTO upon request and payment of the fee set forth in 37 CFR 1.19(b)(3).

The invention claimed is:

1. A polypeptide comprising an amino acid sequence with at least 95% amino acid sequence identity to SEQ ID NO:1, wherein said amino acid sequence comprises one to five mutations at the following X positions of SEQ ID NO:1: $R_{1-95}X_{96}R_{97-98}X_{99}R_{100-122}X_{123}R_{124-186}X_{187}$ $R_{188-203}X_{204}R_{205-211}X_{212}R_{213-272}X_{273}X_{274}X_{275}$ $R_{276-323}X_{324}R_{325-327}X_{328}R_{329-359}X_{360}R_{361-365}X_{366}$ $R_{367-381}X_{382}R_{383-398}$, wherein:

X382 is mutated to a different amino acid selected from Y and W;

X328 is mutated to a different amino acid selected from I, M, A, G, and V;
X187 is mutated to a different amino acid selected from L, M, A, G, and V;
X96 is mutated to a different amino acid selected from L, I, M, A, G, and V;
X99 is mutated to a different amino acid selected from L, I, M, A, G, and V;
X123 is mutated to a different amino acid selected from L, I, M, A, and G;
X204 is mutated to a different amino acid selected from L, I, M, A, and G;
X212 is mutated to a different amino acid selected from F, Y, and W;
X273 is mutated to a different amino acid selected from C, M, S, and T;
X274 is mutated to a different amino acid selected from F, Y, and W;
X275 is mutated to a different amino acid selected from L, I, M, A, and G;
X324 is mutated to a different amino acid selected from L, I, M, G, V, E, D, N, and Q;
X360 is mutated to a different amino acid selected from F, Y, and W;
X366 is mutated to a different amino acid selected from L, I, M, A, G, V, C, and T; and each R is the same as the corresponding amino acid in SEQ ID NO:1;
wherein the amino acid sequence comprises at least one mutation selected from F382W, L328V, and I187M, optionally all three, optionally comprising the amino acid sequence of SEQ ID NO:462 or SEQ ID NO:462 without the periplasmic tag;
wherein the polypeptide is capable of converting 3-buten-2-ol to 1,3-butadiene and/or converting 3-methyl-3-buten-2-ol to isoprene,
and provided that the mutations chosen from one or more of positions X96, X99, X123, and X187 are not the only mutations in SEQ ID NO:1.

2. The polypeptide according to claim 1, wherein $X_{187}$ is mutated to a different amino acid selected from M and equivalent amino acids.

3. The polypeptide according to claim 1, wherein $X_{328}$ is mutated to a different amino acid selected from V and equivalent amino acids.

4. The polypeptide according to claim 1, wherein $X_{382}$ is mutated to a different amino acid selected from W and equivalent amino acids.

5. The polypeptide according to claim 1, comprising the following two mutations: F382W and L328V; optionally comprising only those two mutations.

6. The polypeptide according to claim 1, comprising the following three mutations: F382W, L328V, and I187M; optionally comprising only those three mutations.

7. The polypeptide according to claim 1, wherein said amino acid sequence further comprises a C-terminal His-Tag (His6 or SEQ ID NO:6).

8. The polypeptide according to any one of claim 1, wherein said amino acid sequence lacks a periplasmic tag (SEQ ID NO:3).

9. The polypeptide according to claim 1, wherein the polypeptide has an activity in the catalysis of the dehydration of 3-buten-2-ol to 1,3-butadiene that is at least 80% of that of a polypeptide consisting of SEQ ID NO:1, 4, 5, 7, or 8, increased about 1.5 fold or greater when compared to that of a polypeptide consisting of SEQ ID NO:1, 4, 5, 7, or 8, optionally about 2 fold or greater when compared to that of a polypeptide consisting of SEQ ID NO:1, 4, 5, 7, or 8, optionally about 2.5 fold or greater when compared to that of a polypeptide consisting of SEQ ID NO:1, 4, 5, 7, or 8, optionally about 3 fold or greater when compared to that of a polypeptide consisting of SEQ ID NO:1, 4, 5, 7, or 8, optionally about 3.5 fold or greater when compared to that of a polypeptide consisting of SEQ ID NO:1, 4, 5, 7, or 8, optionally about 4 fold or greater when compared to that of a polypeptide consisting of SEQ ID NO:1, 4, 5, 7, or 8, optionally about 4.5 fold or greater when compared to that of a polypeptide consisting of SEQ ID NO:1, 4, 5, 7, or 8, or optionally about 5 fold or greater when compared to that of a polypeptide consisting of SEQ ID NO:1, 4, 5, 7, or 8, and wherein said activity is observed in at least one activity assay.

10. The polypeptide according to claim 9, wherein said activity in the catalysis of the dehydration of 3-buten-2-ol to 1,3-butadiene is observed in at least one type of non-bacterial cells or at least one type of bacteria.

11. The polypeptide according to claim 1, wherein the polypeptide has an activity in the catalysis of the dehydration of 3-methyl-3-buten-2-ol to isoprene that is at least 80% of that of a polypeptide consisting of SEQ ID NO: 1, 4, 5, 7, or 8, increased about 1.5 fold or greater when compared to that of a polypeptide consisting of SEQ ID NO: 1, 4, 5, 7, or 8, optionally about 2 fold or greater when compared to that of a polypeptide consisting of SEQ ID NO: 1, 4, 5, 7, or 8, optionally about 2.5 fold or greater when compared to that of a polypeptide consisting of SEQ ID NO: 1, 4, 5, 7, or 8, optionally about 3 fold or greater when compared to that of a polypeptide consisting of SEQ ID NO: 1, 4, 5, 7, or 8, optionally about 3.5 fold or greater when compared to that of a polypeptide consisting of SEQ ID NO: 1, 4, 5, 7, or 8, optionally about 4 fold or greater when compared to that of a polypeptide consisting of SEQ ID NO: 1, 4, 5, 7, or 8, optionally about 4.5 fold or greater when compared to that of a polypeptide consisting of SEQ ID NO: 1, 4, 5, 7, or 8, optionally about 5 fold or greater when compared to that of a polypeptide consisting of SEQ ID NO: 1, 4, 5, 7, or 8, optionally about 15 fold or greater when compared to that of a polypeptide consisting of SEQ ID NO: 1, 4, 5, 7, or 8, optionally about 55 fold or greater when compared to that of a polypeptide consisting of SEQ ID NO: 1, 4, 5, 7, or 8, or optionally about 30 fold or greater when compared to that of a polypeptide consisting of SEQ ID NO: 1, 4, 5, 7, or 8, and wherein said activity is observed in at least one activity assay.

12. The polypeptide according to claim 11, wherein said activity in the catalysis of the dehydration of 3-methyl-3-buten-2-ol to isoprene is observed in at least one type of non-bacterial cells or at least one type of bacteria.

13. A composition comprising one or more polypeptides according to.

14. The composition of claim 13, further comprising the polypeptide of SEQ ID NO:1 with or without the N-terminal periplasmic tag, and with or without the first Met.

15. The composition of claim 13, further comprising 3-buten-2-ol and/or 3-methyl-3-buten-2-ol.

16. The composition of claim 13, further comprising 1,3-butadiene and/or isoprene.

17. A composition comprising a rubber product polymerized from 1,3-butadiene or isoprene produced in the presence of the polypeptide according to claim 1.

18. A composition comprising a copolymer polymerized from 1,3-butadiene or isoprene produced in the presence of the polypeptide according to claim 1.

19. A composition comprising a plastic product polymerized from 1,3-butadiene or isoprene produced in the presence of the polypeptide according to claim 1.

20. A fusion protein comprising the polypeptide according to claim 1.

21. A complex comprising the polypeptide according to claim 1, said complex optionally further comprising 3-methyl-3-buten-2-ol.

22. A complex comprising the polypeptide according to claim 1, said complex optionally further comprising 3-buten-2-ol.

* * * * *

UNITED STATES PATENT AND TRADEMARK OFFICE
CERTIFICATE OF CORRECTION

PATENT NO. : 10,519,433 B2
APPLICATION NO. : 15/056026
DATED : December 31, 2019
INVENTOR(S) : Nadia Kadi et al.

Page 1 of 1

It is certified that error appears in the above-identified patent and that said Letters Patent is hereby corrected as shown below:

In the Claims

Claim 2, Column 97, Lines 40-41, "M and equivalent amino acids" should read --L, M, A, G and V--.

Claim 3, Column 97, Lines 43-44, "V and equivalent amino acids" should read --I, M, A, G and V--.

Claim 4, Column 97, Lines 46-47, "W and equivalent amino acids" should read --Y and W--.

Claim 8, Column 97, Line 57, "any one of claim 1," should read --claim 1,--.

Claim 13, Column 98, Line 54, "according to." should read --according to claim 1.--.

Signed and Sealed this
Tenth Day of March, 2020

Andrei Iancu
*Director of the United States Patent and Trademark Office*